(12) United States Patent
Stürmer et al.

(10) Patent No.: US 7,498,448 B2
(45) Date of Patent: Mar. 3, 2009

US007498448B2

(54) METHODS FOR THE PRODUCTION OF 3-METHYLAMINO-1-(THIENE-2-YL)-PROPANE-1-OL

(75) Inventors: Rainer Stürmer, Rödersheim-Gronau (DE); Maria Keβeler, Mannheim (DE); Bernhard Hauer, Fuβgönheim (DE); Thomas Friedrich, Darmstadt (DE); Michael Breuer, Limburgerhof (DE)

(73) Assignee: BASF Aktiengesellschaft (DE)

( * ) Notice: Subject to any disclaimer, the term of this patent is extended or adjusted under 35 U.S.C. 154(b) by 0 days.

(21) Appl. No.: 10/573,130

(22) PCT Filed: Sep. 30, 2004

(86) PCT No.: PCT/EP2004/010939

§ 371 (c)(1),
(2), (4) Date: May 17, 2006

(87) PCT Pub. No.: WO2005/033094

PCT Pub. Date: Apr. 14, 2005

(65) Prior Publication Data

US 2007/0083055 A1    Apr. 12, 2007

(30) Foreign Application Priority Data

Oct. 1, 2003    (DE) ................ 103 45 772

(51) Int. Cl.
  *C07D 333/12*    (2006.01)
(52) U.S. Cl. ........................................ 549/75
(58) Field of Classification Search ............... 549/75
  See application file for complete search history.

(56) References Cited

U.S. PATENT DOCUMENTS

| 5,362,886 A | 11/1994 | Berglund |
| 6,596,520 B1 | 7/2003 | Friedrich et al. |
| 6,645,746 B1 | 11/2003 | Kizaki et al. |

FOREIGN PATENT DOCUMENTS

| DE | 102 48 479 A1 | 5/2004 |
| DE | 102 48 480 A1 | 5/2004 |
| EP | 0273658 B1 | 10/1990 |
| EP | 0457559 A2 | 11/1991 |
| EP | 1149849 B1 | 10/2001 |
| JP | 2003-192681 A | 7/2003 |

OTHER PUBLICATIONS

Wheeler, William J., et al., "An Asymmetric Synthesis of Duloxetine Hydrochloride, a Mixed Uptake Inhibitor of Serotonin and Norepinephrine, and its C-14 Labeled Isotopomers", Journal of Labelled Compounds and Radiopharmaceuticals (1995), vol. 36, No. 3, pp. 213-223.

Kamal, Ahmed, et al., "Chemoenzymatic Synthesis of Duloxetine and its Enantiomer: Lipase-Catalyzed Resolution of 3-Hydroxy-3-(2-thienyl) Propanenitrile", Tetrahedron Letters (2003), vol. 44, No. 25, pp. 4783-4787.
Liu, Huiling, et al., "Chemo-Enzymatic Synthesis of the Antidepressant Duloxetine and Its Enantiomer", Chirality (2000), vol. 12, No. 1, pp. 26-29.
Hummel, Werner, "New Alcohol Dehydrogenases for the Synthesis of Chiral Compounds", Advances in Biochemical Engineering (1997), vol. 58, pp. 145-184.
Riebel-Bommarius, B.R., "Lactobacillus brevis radh Gene for R-specific Alcohol Dehydrogenase", Feb. 14, 2003, Accession No. AJ544275.
Hummel, W., et al., "Sequence 7 from Patent US 6225099", Aug. 9, 2001, Accession No. AR148418.
Kizaki, N., et al., "DNA Encoding Candida magnoliae Carbonyl Reductase", Aug. 31, 2001, Accession No. AAH27641.
Breuer, Michael, et al., "Industrial Methods for the Production of Optically Active Intermediates", Angew. Chem. Int. Ed. (2004), vol. 43, No. 7, pp. 788-824.
Meth-Cohn, Otto, et al., "Thiophene Analogues of Indenes—I. The Synthesis of Indanone Analogues", Acta Chem. Scand. (1966), vol. 820, No. 6, pp. 1577-1587.
Noyori, R., et al., "Asymmetric Catalysis by Architectural and Functional Molecular Engineering: Practical Chemo- and Stereoselective Hydrogenation of Ketones", Angew. Chem. Int. Ed. (2001), vol. 40, pp. 41-73.
Corey, E.J., "New Enantioselective Routes to Biologically Interesting Compounds", Pure & Appl. Chem (1990), vol. 62, vol. 7, pp. 1209-1216.
Corey, E.J., "A General, Catalytic, and Enantioselective Synthesis of α-Amino Acids", J. Am. Chem. Soc. (1992), vol. 114, pp. 1906-1908.
Hummel, Werner, et al., "Towards a Large-Scale Asymmetric Reduction Process with Isolated Enzymes: Expression of an (S)-Alcohol Dehydrogenase in *E. coli* and Studies on the Synthetic Potential of this Biocatalyst", Adv. Synth. Catal. (2003), vol. 345, No. 1+2, pp. 153-159.
Pearson, William R., et al., "Improved Tools for Biological Sequence Comparison", Proc. Natl. Acad. Sci. USA (1988), vol. 85, pp. 2444-2448.
Narang, Saran A., "DNA Synthesis", Tetrahedron (1983), vol. 39, No. 1, pp. 3-22.
Itakura, Keiichi, et al., "Synthesis and Use of Synthetic Oligonucleotides", Ann. Rev. Biochem. (1984), vol. 53, pp. 323-356.
Itakura, Keiichi, et al., "Expression in Escherichia coli of a Chemically Synthesized Gene for the Hormone Somatostatin", Science (1977), vol. 198, pp. 1056-1063.
Ike, Yoshimasa, et al., "Solid Phase Synthesis of Polynucleotides. VIII. Synthesis of Mixed Oligodeoxyribonucleotides by the Phosphotriester Solid Phase Method", Nucleic Acids Research (1983), vol. 11, No. 2, pp. 477-488.

(Continued)

*Primary Examiner*—Taofiq A Solola
(74) *Attorney, Agent, or Firm*—Connolly Bove Lodge & Hutz LLP

(57) ABSTRACT

The present invention relates to enzymic and nonenzymic processes for preparing 3-methylamino-1-(thien-2-yl)propan-1-ol; as well as to enzymes for implementing these processes; and to nucleic acid sequences encoding these enzymes, to expression cassettes containing these nucleic acid sequences, to vectors and to recombinant hosts.

10 Claims, 8 Drawing Sheets

OTHER PUBLICATIONS

Arkin, Adam P., et al., "An Algorithm for Protein Engineering: Simulations of Recursive Ensemble Mutagenesis", Proc. Natl. Acad. Sci. USA (1992), vol. 89, pp. 7811-7815.

Delagrave, Simon, et al., "Recursive Ensemble Mutagenesis", Protein Engineering (1993), vol. 6, No. 3, pp. 327-331.

Thomas, Kirk R., et al., "Site-Directed Mutagenesis by Gene Targeting in Mouse Embryo-Derived Stem Cells", Cell (1987), vol. 51, pp. 503-512.

Takeshita, Sunao, et al., "High-copy-number and Low-copy-number Plasmid Vectors for *lacZ* α-Complementation and Chloramphenicol- or Kanamycin-Resistance Selection", Gene (1987), vol. 61, pp. 63-74.

Tomoyasu, Toshifumi, et al., "Genetic Dissection of the Roles of Chaperones and Proteases in Protein Folding and Degradation in the *Escherichia coli* Cytosol", Molecular Microbiology (2001), vol. 40, No. 2, pp. 397-413.

Étienne, André, et al., "Acide Benzoyl-2 Éthanesulfinique, Acide (Thénoyl-2)-2 Éthanesulfinique et Queiques Uns de Leurs Dérivés", C. R. Acad. Sc. Paris (1979), vol. 288, No. 1, pp. 49-52.

Corey, Elias J., et al., "Reduktion von Carbonylverbindungen mit Chiralen Oxazaborolidin-Katalysatoren: Eine Neue Enantioselektive Katalyse und Leistungsfähige Synthesemethode", Angew. Chem. (1998), vol. 110, pp. 2092-2118.

31278/165 blot band 1 - Lu10288 (N terminus) (SEQ ID NO: 15)

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|
| S | N | R | L | D | G | K | V | A | I | V | T | G | G | T | L | G | I | G | L | A | I | A | T | K |

| 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 |
|---|---|---|---|---|---|---|---|---|---|---|---|---|---|---|---|---|---|---|---|---|---|---|---|---|
| F | V | E | E | G | A | K | V | M | I | T | G | R | H | S | D | V | G | E | K | A | A | (K) | S | V |
|  |  |  |  |  |  |  |  |  |  |  |  |  |  |  |  |  |  |  |  |  | K | (A) |  |  |

| 51 | 52 | 53 | 54 | 55 | 56 | 57 | 58 | 59 | 60 |
|---|---|---|---|---|---|---|---|---|---|
| G | T | P | D | Q | I | Q | F | F | / |
|  |  | T |  |  |  |  |  | V | / |
|  |  |  |  |  |  |  |  | G | / |
|  |  |  |  |  |  |  |  | N | / |

Fig. 3B

1. Tryptic liquid digestion Fr. 34 UP Mono P 31279/170

<u>Tr-Sp-RPFr. 4</u>  (SEQ ID NO: 16)

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
| T | P | L | V | D | D | L | P | G | A  | E  | E  | A  | M  | S  | Q  | R  | (R)| /  | /  |
| S | V | G | T | P | E | Q | I | Q | F  | F  | Q  | H  | D  | R  |    |    |    |    |    |
| F | A | T |   | S | I | F | V | K |    |    |    |    | Y  | T  |    |    |    |    |    |
|   |   |   |   |   |   |   | A | P |    |    |    |    |    |    |    |    |    |    |    |

<u>Tr.-Sp.-RP Fr. 6</u>  (SEQ ID NO: 17)

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
|   | S | V | E | E | T | T | T | A | E  | (W)| R  | /  | /  | /  |

<u>Tr.-Sp.-RP Fr. 18</u>  (SEQ ID NO: 18)

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
| S | V | G | T | P | D | Q | J | Q | F  | F  | Q  | H  | D  | S  | S  | D  | E  | D  | G  |

<u>Tr.-Sp.-RP Fr. 4 (3/4 of filter)</u>  (SEQ ID NO: 19)

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
| <u>V</u> | <u>N</u> | <u>T</u> | <u>V</u> | <u>H</u> | <u>P</u> | <u>G</u> | <u>Y</u> | <u>J</u> | <u>K</u> | / | / | / | / | / |
| L | F | D | A | T | E | K | / | / | / | / | / | / | / | / |

<u>Tr.-Sp.-RP Fr. 4 (1/4 of filter)</u>  (SEQ ID NO: 20)

| 1 | 2 | 3 | 4 |
|---|---|---|---|
| <u>V</u> | <u>N</u> | <u>T</u> | <u>V</u> |
| L | F | D | A |

<u>Tr.-RP Fr. 3</u>  (SEQ ID NO: 21)

| 1 | 2 | 3 | 4 | 5 | 6 | 7 |
|---|---|---|---|---|---|---|
| <u>A</u> | <u>E</u> | <u>I</u> | <u>P</u> | <u>G</u> | <u>K</u> | <u>R</u> |
| V | M |   | Q | Y |   | N |
| I |   |   |   |   |   |   |
| L,S |   |   |   |   |   |   |

Fig. 3B (Continued)

Tr.-Sp.-RP Fr. 8 (SEQ ID NO: 22)

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
| (S) | A | A | L | D | / | A | L | K | / | / | / | / | / | / |

Tr.-Sp.-RP Fr. 23 (SEQ ID NO: 23)

| 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|----|----|----|----|----|----|----|----|----|
| <u>S</u> | <u>A</u> | <u>A</u> | <u>L</u> | <u>D</u> | / | <u>A</u> | <u>L</u> | <u>K</u> | <u>D</u> | <u>Y</u> | / | <u>V</u> | <u>R</u> | / | / | / | / |
| F | (A) | T | G | S | E | F | V | V | (D) | G | G | Y | T | A | Q | / | / |

Tr.-Sp.-RP Fr. 14 (SEQ ID NO: 24)

| 1 | 2 | 3 | 4 | 5 | 6 | 7 | 8 | 9 | 10 | 11 | 12 | 13 | 14 | 15 | 16 | 17 |
|---|---|---|---|---|---|---|---|---|----|----|----|----|----|----|----|----|
| <u>S</u> | <u>A</u> | <u>A</u> | <u>L</u> | <u>D</u> | / | <u>A</u> | <u>L</u> | <u>K</u> | / | / | / | / | / | / | / | / |

Tr.-Sp.-RP Fr. 31 (SEQ ID NO: 25)

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
| K | L | L | A | V | N | L | D | G | V | F | F | G | T | R | / | / | / | / | / |

Tr.-Sp.-RP Fr. 2 (SEQ ID NO: 26)

| 1 | 2 | 3 | 4 | 5 | 6 |
|---|---|---|---|---|---|
| / | M | / | T | G | R |

Tr.-Sp.-RP Fr. 27 (SEQ ID NO:27)

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
| <u>T</u> | <u>K</u> | <u>I</u> | <u>P</u> | <u>M</u> | <u>G</u> | <u>H</u> | <u>I</u> | / | <u>E</u> | <u>P</u> | <u>N</u> | / | <u>I</u> | <u>A</u> |
| S | A | A | L | D | G | A | L | K | D | Y | D | V | R | / |
| F | A | T | G | S | E | F | V | V | D | G | G | Y | T | A |

Tr.-Sp.-RP Fr. 28 (SEQ ID NO: 28)

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
| <u>I</u> | <u>K</u> | <u>I</u> | <u>P</u> | <u>M</u> | <u>G</u> | ? | <u>I</u> | (A) | <u>E</u> | (P) | (N) | (D) | <u>I</u> | <u>A</u> | Y | / | / | / | / |
| F | A | T | G | S | E | F | V | V | D | G | G | Y | T | A | Q | | | | |
| S | A | A | L | D | (C) | A | L | K | D | Y | D | V | R | / | | | | | |

Fig. 3B (Continued)

2. V8 liquid digestion Fr.34 UP Mono P 31279/170

V8-RPFr. 30 (SEQ ID NO: 29)

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|
| K | A | A | K | S | V | G | T | P | D | Q | I | Q | F | F | Q | H | D | S | S | P | E | (V) | (V) | (Q) |
| T | G | L | F | L |   | V | L | R | V | A | T | V |   | P | G | Y | I | K | A | T |   | A | N |   |
| Q |   |   |   | R |   |   | V |   | N | E |   |   |   |   |   |   |   | D |   |   |   |   |   |   |

V8-RPFr. 19 (SEQ ID NO: 30)

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|
| / | <u>V</u> | <u>K</u> | <u>L</u> | <u>L</u> | <u>A</u> | <u>V</u> | <u>N</u> | <u>L</u> | / | / | / | / | / | / | / | / | / | / | / |
|   | K |   |   | A |   |   |   |   | I |   |   |   |   |   |   |   |   |   |   |
|   | R |   |   |   |   |   |   |   | D |   |   |   |   |   |   |   |   |   |   |

V8-RPFr. 18 (SEQ ID NO: 31)

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|
| <u>T/G</u> | <u>V</u> | <u>F</u> | <u>F</u> | <u>(G)</u> | <u>L</u> | <u>K</u> | <u>Q</u> | <u>N</u> | <u>I</u> | <u>E</u> | <u>N</u> | <u>I</u> | <u>N</u> | <u>I/N</u> | <u>A</u> | <u>A</u> | <u>V</u> | <u>R</u> | <u>(P)</u> |
| V |   | V | N | T | V | H | P | G | Y | I | K | T | P | L | M | D | D | D |   |
|   |   |   |   |   |   |   |   |   |   |   |   |   |   |   |   | G |   |   | L |
|   |   |   |   |   |   |   |   |   |   |   |   |   |   |   |   | V |   |   |   |

V8-RPFr. 22 (SEQ ID NO: 32)

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|
| <u>G</u> | <u>F</u> | <u>V</u> | <u>G</u> | <u>D</u> | <u>P</u> | <u>S</u> | <u>L</u> | <u>G</u> | <u>A</u> | <u>Y</u> | <u>N</u> | <u>A</u> | <u>G</u> | <u>K</u> | <u>G</u> | <u>A</u> | <u>V</u> | <u>R</u> | <u>I</u> |
| Q | V | L |   | A | Q | N | M | K | N | G | G | L | S | A | M | I | K | N | M |
| T | S |   |   |   | I | Y | R | A |   | K | K | A | V | R | I | S |   |   | A |
| P |   |   |   |   |   | K |   |   |   |   |   |   |   |   |   |   |   |   |   |

| 21 | 22 | 23 | 24 | 25 | 26 | 27 | 28 | 29 | 30 |
|---|---|---|---|---|---|---|---|---|---|
| <u>M</u> | <u>S</u> | <u>K</u> | <u>S</u> | <u>A</u> | <u>A</u> | <u>L</u> | <u>(D)</u> | / | / |

V8-RP Fr. 4 (SEQ ID NO: 33)

| 1 | 2 | 3 | 4 | 5 | 6 | 7 | 8 | 9 | 10 |
|---|---|---|---|---|---|---|---|---|---|
| F | V | V | D | / | / | / | / | / | / |

Fig. 3B (Continued)

V8-RPFr. 26 (SEQ ID NO: 34)

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
| D | G | / | T | K | L | F | D | A | I  | E  | (E)| /  | /  | /  | /  | /  | /  | /  | /  |
| R | K | (L)| K | D | A |   | E | D |    |    |    |    |    |    |    |    |    |    |    |
|   | Y | (F)|   | P |   |   |   |   |    |    |    |    |    |    |    |    |    |    |    |    |

V8-RP Fr. 7 (C terminus) (SEQ ID NO: 35)

| 1 | 2 | 3 | 4 | 5 | 6 | 7 | 8 | 9 | 10 | 11 | 12 | 13 | 14 |
|---|---|---|---|---|---|---|---|---|----|----|----|----|----|
| F | V | V | D | G | G | Y | T | A | Q  | /  | /  | /  | /  |

V8-RP Fr. 28 (SEQ ID NO: 36)

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
| / | A | L | K | D | Y | D | V | R | V  | N  | I  | V  | H  | P  | G  | Y  | I  | K  | T  |
|   | S |   |   |   |   |   |   |   |    |    |    |    |    |    |    |    |    |    |    |

| 21 | 22 | 23 | 24 | 25 | 26 | 27 | 28 | 29 | 30 |
|----|----|----|----|----|----|----|----|----|----|
| P  | L  | V  | (V)| D  | L  | P  | G  | A  | E  |
|    |    |    | D  |    |    |    |    |    | (G)|

V8-RP Fr. 9 (SEQ ID NO: 37)

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
| K | A | A | K | S | V | G | T | P | D  | Q  | I  | Q  | F  | F  |

V8-RP Fr. 2 (SEQ ID NO: 38)

| 1 | 2 | 3 | 4 | 5 | 6 | 7 | 8 | 9 | 10 | 11 | 12 | 13 |
|---|---|---|---|---|---|---|---|---|----|----|----|----|
| G | A | K | V | M | I | T | G | R | H  | S  | D  | V  |

V8-RP Fr. 12 (SEQ ID NO: 39)

| 1 | 2 | 3 | 4 | 5 | 6 | 7 | 8 | 9 | 10 |
|---|---|---|---|---|---|---|---|---|----|
| S | K | F | A | T | G | S | E | F | V  |
| A |   | G |   | F | V | Y | L |   |    |
|   |   | I |   |   |   |   |   |   |    |

Fig. 3B (Continued)

V8-RP Fr. 21 (SEQ ID NO: 40)

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
| / | D | V | R | V | N | I | V | H | P | G | Y | I | K | I | P | L | V | D | D |
|   | V | F | K | I |   |   |   |   |   |   |   |   | G | A |   |   |   | N | M |
|   | S | L | G | A |   |   |   |   |   |   |   |   |   |   |   |   |   |   |   |
|   | L |   | G |   |   |   |   |   |   |   |   |   |   |   |   |   |   |   |   |

| 21 | 22 | 23 | 24 | 25 |
|----|----|----|----|----|
| L | P | G | A | E |
| L |   |   |   |   |

V8-RP Fr. 41 (SEQ ID NO: 41)

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
| W | I | K | L | L | A | V | N | L | D | G | V | F | F | G | T | R | L | G | I |

| 21 | 22 | 23 | 24 | 25 | 26 | 27 | 28 | 29 | 30 | 31 | 32 | 33 | 34 | 35 | 36 | 37 | 38 | 39 | 40 |
|----|----|----|----|----|----|----|----|----|----|----|----|----|----|----|----|----|----|----|----|
| Q | R | M | K | N | K | G | L | G | A | S | I | I | N | M | (S) | (S) | (I) | / | / |

V8-RP Fr. 43 (SEQ ID NO: 42)

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
| (A) | M | S | Q | R | I | K | I | P | M | G | H | I | (G) | E | P | N | D | I | A |
|   |   | K | L | L | A | V | N | L | D | G | V | F | F | G | T | R | L | G | I |
|   |   | A | K | S | V | G |   | A | Q | I | A |   |   |   |   |   |   |   |   |
|   |   | E |   |   |   |   |   | Y | N | Q |   |   |   |   |   |   |   |   |   |

| 21 | 22 | 23 | 24 | 25 | 26 | 27 | 28 | 29 | 30 | 31 | 32 | 33 | 34 | 35 | 36 | 37 | 38 | 39 | 40 |
|----|----|----|----|----|----|----|----|----|----|----|----|----|----|----|----|----|----|----|----|
| Y |   |   |   | Y |   | A |   |   |   |   |   |   |   |   |   |   |   |   |   |
| Q | R | M | K | N | K | G | L | G | A | S | I | I | N | M | S |   |   |   | G |

V8-RP Fr. 11 (SEQ ID NO: 43)

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
| S | K | F | A | T | G | S | E | F | V | V | / | / | / | / |

V8-RP Fr. 15 (SEQ ID NO: 44)

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
| S | K | F | A | T | G | S | E | F | V | V | D | / | / | / |
| A |   |   |   | T | I | L | Q | I | Q |   | L | Q |   |   |
| F |   |   |   |   | P | D |   |   |   |   | S | K |   |   |
| V |   |   |   |   |   |   |   |   |   |   |   |   |   |   |

SEQUENCE LISTING

<160> NUMBER OF SEQ ID NOS: 44

<210> SEQ ID NO 1
<211> LENGTH: 47
<212> TYPE: PRT
<213> ORGANISM: Lactobacillus brevis

<400> SEQUENCE: 1

Met Ser Asn Arg Leu Asp Gly Lys Val Ala Ile Val Thr Gly Gly Thr
1               5                   10                  15

Leu Gly Ile Gly Leu Ala Ile Ala Thr Lys Phe Val Glu Glu Gly Ala
            20                  25                  30

Lys Val Met Ile Thr Gly Arg His Ser Asp Val Gly Glu Lys Ala
        35                  40                  45

<210> SEQ ID NO 2
<211> LENGTH: 18
<212> TYPE: PRT
<213> ORGANISM: Candida magnoliae

<400> SEQUENCE: 2

Ser Asn Ala Leu Val Thr Gly Gly Ser Arg Val Ile Gly Ala Gly Gly
1               5                   10                  15

Phe Ile

<210> SEQ ID NO 3
<211> LENGTH: 756
<212> TYPE: DNA
<213> ORGANISM: Lactobacillus brevis
<220> FEATURE:
<221> NAME/KEY: CDS
<222> LOCATION: (1)..(756)

<400> SEQUENCE: 3 atg tct aac cgt ttg gat gga aaa gta gca atc gtt aca ggt ggt acg      48
Met Ser Asn Arg Leu Asp Gly Lys Val Ala Ile Val Thr Gly Gly Thr
1               5                   10                  15 ttg ggt atc ggt tta gct atc gcc acg aag ttc gtt gaa gaa ggg gct      96
Leu Gly Ile Gly Leu Ala Ile Ala Thr Lys Phe Val Glu Glu Gly Ala
            20                  25                  30 aag gtc atg att acc ggc cgg cac agc gat gtt ggt gaa aaa gca gct     144

```
Lys Val Met Ile Thr Gly Arg His Ser Asp Val Gly Glu Lys Ala Ala
             35                  40                  45 aag agt gtc ggc act cct gat cag att caa ttt ttc caa cat gat tct       192
Lys Ser Val Gly Thr Pro Asp Gln Ile Gln Phe Phe Gln His Asp Ser
 50                  55                  60 tcc gat gaa gac ggc tgg acg aaa tta ttc gat gca acg gaa aaa gcc       240
Ser Asp Glu Asp Gly Trp Thr Lys Leu Phe Asp Ala Thr Glu Lys Ala
 65                  70                  75                  80 ttt ggc cca gtt tct aca tta gtt aat aac gct ggg atc gcg gtt aac       288
Phe Gly Pro Val Ser Thr Leu Val Asn Asn Ala Gly Ile Ala Val Asn
                 85                  90                  95 aag agt gtc gaa gaa acc acg act gct gaa tgg cgt aaa cta tta gcc       336
Lys Ser Val Glu Glu Thr Thr Thr Ala Glu Trp Arg Lys Leu Leu Ala
            100                 105                 110 gtc aac ctt gat ggt gtc ttc ttc ggt acc cga tta ggg att caa cgg       384
Val Asn Leu Asp Gly Val Phe Phe Gly Thr Arg Leu Gly Ile Gln Arg
            115                 120                 125 atg aag aac aaa ggc tta ggg gct tcc atc atc aac atg tct tcg atc       432
Met Lys Asn Lys Gly Leu Gly Ala Ser Ile Ile Asn Met Ser Ser Ile
130                 135                 140 gaa ggc ttt gtg ggt gat cct agc tta ggg gct tac aac gca tct aaa       480
Glu Gly Phe Val Gly Asp Pro Ser Leu Gly Ala Tyr Asn Ala Ser Lys
145                 150                 155                 160 ggg gcc gta cgg att atg tcc aag tca gct gcc tta gat tgt gcc cta       528
Gly Ala Val Arg Ile Met Ser Lys Ser Ala Ala Leu Asp Cys Ala Leu
                165                 170                 175 aag gac tac gat gtt cgg gta aac act gtt cac cct ggc tac atc aag       576
Lys Asp Tyr Asp Val Arg Val Asn Thr Val His Pro Gly Tyr Ile Lys
            180                 185                 190 aca cca ttg gtt gat gac cta cca ggg gcc gaa gaa gcg atg tca caa       624
Thr Pro Leu Val Asp Asp Leu Pro Gly Ala Glu Glu Ala Met Ser Gln
            195                 200                 205 cgg acc aag acg cca atg ggc cat atc ggt gaa cct aac gat att gcc       672
Arg Thr Lys Thr Pro Met Gly His Ile Gly Glu Pro Asn Asp Ile Ala
        210                 215                 220 tac atc tgt gtt tac ttg gct tct aac gaa tct aaa ttt gca acg ggt       720
Tyr Ile Cys Val Tyr Leu Ala Ser Asn Glu Ser Lys Phe Ala Thr Gly
225                 230                 235                 240 tct gaa ttt gta gtt gac ggt ggc tac act gct caa                       756
Ser Glu Phe Val Val Asp Gly Gly Tyr Thr Ala Gln
                245                 250

<210> SEQ ID NO 4
<211> LENGTH: 252
<212> TYPE: PRT
<213> ORGANISM: Lactobacillus brevis

<400> SEQUENCE: 4

Met Ser Asn Arg Leu Asp Gly Lys Val Ala Ile Val Thr Gly Gly Thr
 1               5                  10                  15

Leu Gly Ile Gly Leu Ala Ile Ala Thr Lys Phe Val Glu Glu Gly Ala
             20                  25                  30

Lys Val Met Ile Thr Gly Arg His Ser Asp Val Gly Glu Lys Ala Ala
             35                  40                  45

Lys Ser Val Gly Thr Pro Asp Gln Ile Gln Phe Phe Gln His Asp Ser
         50                  55                  60

Ser Asp Glu Asp Gly Trp Thr Lys Leu Phe Asp Ala Thr Glu Lys Ala
 65                  70                  75                  80

Phe Gly Pro Val Ser Thr Leu Val Asn Asn Ala Gly Ile Ala Val Asn
```

```
                        85                  90                  95
Lys Ser Val Glu Glu Thr Thr Thr Ala Glu Trp Arg Lys Leu Leu Ala
            100                 105                 110
Val Asn Leu Asp Gly Val Phe Phe Gly Thr Arg Leu Gly Ile Gln Arg
            115                 120                 125
Met Lys Asn Lys Gly Leu Gly Ala Ser Ile Ile Asn Met Ser Ser Ile
            130                 135                 140
Glu Gly Phe Val Gly Asp Pro Ser Leu Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Tyr Ile Lys
            180                 185                 190
Thr Pro Leu Val Asp Asp Leu Pro Gly Ala Glu Glu Ala Met Ser Gln
            195                 200                 205
Arg Thr Lys Thr Pro Met Gly His Ile Gly Glu Pro Asn Asp Ile Ala
            210                 215                 220
Tyr Ile Cys Val Tyr Leu Ala Ser Asn Glu Ser Lys Phe Ala Thr Gly
225                 230                 235                 240
Ser Glu Phe Val Val Asp Gly Gly Tyr Thr Ala Gln
                245                 250

<210> SEQ ID NO 5
<211> LENGTH: 472
<212> TYPE: DNA
<213> ORGANISM: Candida magnoliae
<220> FEATURE:
<221> NAME/KEY: CDS
<222> LOCATION: (1)..(471)

<400> SEQUENCE: 5 aac gcg ctg gtg acg ggc ggc agc cgc ggc att ggc gaa gcc act gcc        48
Asn Ala Leu Val Thr Gly Gly Ser Arg Gly Ile Gly Glu Ala Thr Ala
1               5                   10                  15 att aag ctc gcc gag gag ggc tac agc gtc acg att gcg tct cgc ggc        96
Ile Lys Leu Ala Glu Glu Gly Tyr Ser Val Thr Ile Ala Ser Arg Gly
                20                  25                  30 ctt aag cag ctc gag gct gtg aag gcc aaa cta ccc att gtg aag cag       144
Leu Lys Gln Leu Glu Ala Val Lys Ala Lys Leu Pro Ile Val Lys Gln
            35                  40                  45 gga cag gtt cac cac gtg tgg cag ctt gat ctc agt gat gtc gac gct       192
Gly Gln Val His His Val Trp Gln Leu Asp Leu Ser Asp Val Asp Ala
        50                  55                  60 gcg gcc gcc ttc aaa ggg tcg ccg cta cct gcc agc cgc tac gac gtg       240
Ala Ala Ala Phe Lys Gly Ser Pro Leu Pro Ala Ser Arg Tyr Asp Val
65                  70                  75                  80 ctc gtc agc aat gct ggc gtg gcc cag ttt agc ccg ttc atc gag cat       288
Leu Val Ser Asn Ala Gly Val Ala Gln Phe Ser Pro Phe Ile Glu His
                85                  90                  95 gcg aag cag gac tgg tcg cag atg ctt gcc atc aat ctg gcg gca ccc       336
Ala Lys Gln Asp Trp Ser Gln Met Leu Ala Ile Asn Leu Ala Ala Pro
            100                 105                 110 att gcg ctg gcc cag aca ttt gct aag gcc att ggc gac aag ccg cgc       384
Ile Ala Leu Ala Gln Thr Phe Ala Lys Ala Ile Gly Asp Lys Pro Arg
        115                 120                 125 aac aca ccg gcc cac att gtg ttt gtc tcg tcg aac gtc tcg ttg cga       432
Asn Thr Pro Ala His Ile Val Phe Val Ser Ser Asn Val Ser Leu Arg
    130                 135                 140
```

```
ggc ttc ccg aac atc ggc gtc aac tcc atc acc ccc ggc a      472
Gly Phe Pro Asn Ile Gly Val Asn Ser Ile Thr Pro Gly
145                 150                 155

<210> SEQ ID NO 6
<211> LENGTH: 157
<212> TYPE: PRT
<213> ORGANISM: Candida magnoliae

<400> SEQUENCE: 6

Asn Ala Leu Val Thr Gly Gly Ser Arg Gly Ile Gly Glu Ala Thr Ala
1               5                   10                  15

Ile Lys Leu Ala Glu Glu Gly Tyr Ser Val Thr Ile Ala Ser Arg Gly
                20                  25                  30

Leu Lys Gln Leu Glu Ala Val Lys Ala Lys Leu Pro Ile Val Lys Gln
            35                  40                  45

Gly Gln Val His His Val Trp Gln Leu Asp Leu Ser Asp Val Asp Ala
    50                  55                  60

Ala Ala Ala Phe Lys Gly Ser Pro Leu Pro Ala Ser Arg Tyr Asp Val
65              70                  75                  80

Leu Val Ser Asn Ala Gly Val Ala Gln Phe Ser Pro Phe Ile Glu His
                85                  90                  95

Ala Lys Gln Asp Trp Ser Gln Met Leu Ala Ile Asn Leu Ala Ala Pro
            100                 105                 110

Ile Ala Leu Ala Gln Thr Phe Ala Lys Ala Ile Gly Asp Lys Pro Arg
        115                 120                 125

Asn Thr Pro Ala His Ile Val Phe Val Ser Ser Asn Val Ser Leu Arg
    130                 135                 140

Gly Phe Pro Asn Ile Gly Val Asn Ser Ile Thr Pro Gly
145                 150                 155

<210> SEQ ID NO 7
<211> LENGTH: 27
<212> TYPE: DNA
<213> ORGANISM: Artificial sequence
<220> FEATURE:
<223> OTHER INFORMATION: Primer: Mke 338

<400> SEQUENCE: 7
gggaattcca tatgtctaac cgtttgg                               27

<210> SEQ ID NO 8
<211> LENGTH: 28
<212> TYPE: DNA
<213> ORGANISM: Artificial sequence
<220> FEATURE:
<223> OTHER INFORMATION: Primer: Mke 339

<400> SEQUENCE: 8
cgtagggaag cttattgagc agtgtagc                              28

<210> SEQ ID NO 9
<211> LENGTH: 28
<212> TYPE: DNA
<213> ORGANISM: Artificial sequence
<220> FEATURE:
<223> OTHER INFORMATION: Primer: Mke 366

<400> SEQUENCE: 9
acgacgacga gcaacgcbct bgtbacgg                              28
```

-continued

<210> SEQ ID NO 10
<211> LENGTH: 28
<212> TYPE: DNA
<213> ORGANISM: Artificial sequence
<220> FEATURE:
<223> OTHER INFORMATION: Primer: Mke 367

<400> SEQUENCE: 10
acgacgacgt cgaacgcbct bgtbacgg                                28

<210> SEQ ID NO 11
<211> LENGTH: 27
<212> TYPE: DNA
<213> ORGANISM: Artificial sequence
<220> FEATURE:
<223> OTHER INFORMATION: Primer: Mke 374

<400> SEQUENCE: 11
gccggggttg atsswgttsa cgccgat                                 27

<210> SEQ ID NO 12
<211> LENGTH: 10
<212> TYPE: PRT
<213> ORGANISM: Lactobacillus brevis
<220> FEATURE:
<221> NAME/KEY: MISC_FEATURE
<222> LOCATION: (1)..(10)
<223> OTHER INFORMATION: Fragment: C terminus

<400> SEQUENCE: 12

Phe Val Val Asp Gly Gly Tyr Thr Ala Gln
1               5                   10

<210> SEQ ID NO 13
<211> LENGTH: 18
<212> TYPE: PRT
<213> ORGANISM: Candida magnoliae
<220> FEATURE:
<221> NAME/KEY: misc_feature
<222> LOCATION: (1)..(1)
<223> OTHER INFORMATION: Xaa is Ser, Gly or Thr
<220> FEATURE:
<221> NAME/KEY: misc_feature
<222> LOCATION: (2)..(2)
<223> OTHER INFORMATION: Xaa is Thr or Pro

<400> SEQUENCE: 13

Ser Thr Thr Ser Asn Ala Leu Val Thr Gly Gly Ser Arg Gly Ile Gly
1               5                   10                  15

Ala Ala

<210> SEQ ID NO 14
<211> LENGTH: 9
<212> TYPE: PRT
<213> ORGANISM: Candida magnoliae

<400> SEQUENCE: 14

Ile Gly Val Asn Ser Ile Asn Pro Gly
1               5

<210> SEQ ID NO 15
<211> LENGTH: 60
<212> TYPE: PRT
<213> ORGANISM: Lactobacillus brevis
<220> FEATURE:
<221> NAME/KEY: misc_feature
<222> LOCATION: (47)..(47)
<223> OTHER INFORMATION: Xaa is Ala or Lys

```
<220> FEATURE:
<221> NAME/KEY: UNSURE
<222> LOCATION: (48)..(48)
<223> OTHER INFORMATION: Xaa is Lys or Ala
<220> FEATURE:
<221> NAME/KEY: misc_feature
<222> LOCATION: (53)..(53)
<223> OTHER INFORMATION: Xaa is Pro or Thr
<220> FEATURE:
<221> NAME/KEY: misc_feature
<222> LOCATION: (59)..(59)
<223> OTHER INFORMATION: Xaa is Phe, Val, Gly, or Asn
<220> FEATURE:
<221> NAME/KEY: misc_feature
<222> LOCATION: (60)..(60)
<223> OTHER INFORMATION: Xaa is unknown

<400> SEQUENCE: 15

Ser Asn Arg Leu Asp Gly Lys Val Ala Ile Val Thr Gly Gly Thr Leu
1               5                   10                  15

Gly Ile Gly Leu Ala Ile Ala Thr Lys Phe Val Glu Glu Gly Ala Lys
            20                  25                  30

Val Met Ile Thr Gly Arg His Ser Asp Val Gly Glu Lys Ala Xaa Xaa
        35                  40                  45

Ser Val Gly Thr Xaa Asp Gln Ile Gln Phe Xaa Xaa
    50                  55                  60

<210> SEQ ID NO 16
<211> LENGTH: 20
<212> TYPE: PRT
<213> ORGANISM: Lactobacillus brevis
<220> FEATURE:
<221> NAME/KEY: misc_feature
<222> LOCATION: (1)..(1)
<223> OTHER INFORMATION: Xaa is Thr, Ser, or Phe
<220> FEATURE:
<221> NAME/KEY: misc_feature
<222> LOCATION: (2)..(2)
<223> OTHER INFORMATION: Xaa is Pro, Val, or Ala
<220> FEATURE:
<221> NAME/KEY: misc_feature
<222> LOCATION: (3)..(3)
<223> OTHER INFORMATION: Xaa is Leu, Gly, or Thr
<220> FEATURE:
<221> NAME/KEY: misc_feature
<222> LOCATION: (4)..(4)
<223> OTHER INFORMATION: Xaa is Val or Thr
<220> FEATURE:
<221> NAME/KEY: misc_feature
<222> LOCATION: (5)..(5)
<223> OTHER INFORMATION: Xaa is Asp, Pro, or Ser
<220> FEATURE:
<221> NAME/KEY: misc_feature
<222> LOCATION: (6)..(6)
<223> OTHER INFORMATION: Xaa is Asp, Glu, or Ile
<220> FEATURE:
<221> NAME/KEY: misc_feature
<222> LOCATION: (7)..(7)
<223> OTHER INFORMATION: Xaa is Leu, Gln, Phe, or Ala
<220> FEATURE:
<221> NAME/KEY: misc_feature
<222> LOCATION: (8)..(8)
<223> OTHER INFORMATION: Xaa is Pro, Ile, or Val
<220> FEATURE:
<221> NAME/KEY: misc_feature
<222> LOCATION: (9)..(9)
<223> OTHER INFORMATION: Xaa is Gly, Gln, Lys, or Pro
<220> FEATURE:
<221> NAME/KEY: misc_feature
<222> LOCATION: (10)..(10)
<223> OTHER INFORMATION: Xaa is Ala or Phe
<220> FEATURE:
<221> NAME/KEY: misc_feature
<222> LOCATION: (11)..(11)
```

<223> OTHER INFORMATION: Xaa is Glu or Phe
<220> FEATURE:
<221> NAME/KEY: misc_feature
<222> LOCATION: (12)..(12)
<223> OTHER INFORMATION: Xaa is Glu or Gln
<220> FEATURE:
<221> NAME/KEY: misc_feature
<222> LOCATION: (13)..(13)
<223> OTHER INFORMATION: Xaa is Ala, His, or Tyr
<220> FEATURE:
<221> NAME/KEY: misc_feature
<222> LOCATION: (14)..(14)
<223> OTHER INFORMATION: Xaa is Met, Asp, or Thr
<220> FEATURE:
<221> NAME/KEY: misc_feature
<222> LOCATION: (15)..(15)
<223> OTHER INFORMATION: Xaa is Ser or Arg
<220> FEATURE:
<221> NAME/KEY: UNSURE
<222> LOCATION: (18)..(18)
<220> FEATURE:
<221> NAME/KEY: misc_feature
<222> LOCATION: (19)..(20)
<223> OTHER INFORMATION: Xaa is unknown

<400> SEQUENCE: 16

Xaa Xaa Xaa Xaa Xaa Xaa Xaa Xaa Xaa Xaa Xaa Xaa Xaa Xaa Xaa Gln
1               5                   10                  15

Arg Arg Xaa Xaa
            20

<210> SEQ ID NO 17
<211> LENGTH: 15
<212> TYPE: PRT
<213> ORGANISM: Lactobacillus brevis
<220> FEATURE:
<221> NAME/KEY: UNSURE
<222> LOCATION: (10)..(10)
<220> FEATURE:
<221> NAME/KEY: misc_feature
<222> LOCATION: (12)..(15)
<223> OTHER INFORMATION: Xaa is unknown

<400> SEQUENCE: 17

Ser Val Glu Glu Thr Thr Thr Ala Glu Trp Arg Xaa Xaa Xaa Xaa
1               5                   10                  15

<210> SEQ ID NO 18
<211> LENGTH: 20
<212> TYPE: PRT
<213> ORGANISM: Lactobacillus brevis
<220> FEATURE:
<221> NAME/KEY: misc_feature
<222> LOCATION: (8)..(8)
<223> OTHER INFORMATION: Xaa is J

<400> SEQUENCE: 18

Ser Val Gly Thr Pro Asp Gln Xaa Gln Phe Phe Gln His Asp Ser Ser
1               5                   10                  15

Asp Glu Asp Gly
            20

<210> SEQ ID NO 19
<211> LENGTH: 15
<212> TYPE: PRT
<213> ORGANISM: Lactobacillus brevis
<220> FEATURE:
<221> NAME/KEY: misc_feature
<222> LOCATION: (1)..(1)
<223> OTHER INFORMATION: Xaa is Val (main residue from sequencing) or
      Leu <220> FEATURE:
<221> NAME/KEY: misc_feature
<222> LOCATION: (2)..(2)
<223> OTHER INFORMATION: Xaa is Asn (main residue from sequencing) or
      Phe
<220> FEATURE:
<221> NAME/KEY: misc_feature
<222> LOCATION: (3)..(3)
<223> OTHER INFORMATION: Xaa is Thr (main residue from sequencing) or
      Asp
<220> FEATURE:
<221> NAME/KEY: misc_feature
<222> LOCATION: (4)..(4)
<223> OTHER INFORMATION: Xaa is Val (main residue from sequencing) or
      Ala
<220> FEATURE:
<221> NAME/KEY: misc_feature
<222> LOCATION: (5)..(5)
<223> OTHER INFORMATION: Xaa is His (main residue from sequencing) or
      Thr
<220> FEATURE:
<221> NAME/KEY: misc_feature
<222> LOCATION: (6)..(6)
<223> OTHER INFORMATION: Xaa is Pro (main residue from sequencing) or
      Glu
<220> FEATURE:
<221> NAME/KEY: misc_feature
<222> LOCATION: (7)..(7)
<223> OTHER INFORMATION: Xaa is Gly (main residue from sequencing) or
      Lys
<220> FEATURE:
<221> NAME/KEY: misc_feature
<222> LOCATION: (8)..(8)
<223> OTHER INFORMATION: Xaa is Tyr (main residue from sequencing) or
      unknown
<220> FEATURE:
<221> NAME/KEY: misc_feature
<222> LOCATION: (9)..(9)
<223> OTHER INFORMATION: Xaa is J (main residue from sequencing) or
      unknown
<220> FEATURE:
<221> NAME/KEY: misc_feature
<222> LOCATION: (10)..(10)
<223> OTHER INFORMATION: Xaa is Lys (main residue from sequencing) or
      unknown
<220> FEATURE:
<221> NAME/KEY: misc_feature
<222> LOCATION: (11)..(15)
<223> OTHER INFORMATION: Xaa is unknown

<400> SEQUENCE: 19

Xaa Xaa Xaa Xaa Xaa Xaa Xaa Xaa Xaa Xaa Xaa Xaa Xaa Xaa Xaa
1               5                   10                  15

<210> SEQ ID NO 20
<211> LENGTH: 4
<212> TYPE: PRT
<213> ORGANISM: Lactobacillus brevis
<220> FEATURE:
<221> NAME/KEY: misc_feature
<222> LOCATION: (1)..(1)
<223> OTHER INFORMATION: Xaa is Val (main residue from sequencing) or
      Leu
<220> FEATURE:
<221> NAME/KEY: misc_feature
<222> LOCATION: (2)..(2)
<223> OTHER INFORMATION: Xaa is Asn (main residue from sequencing) or
      Phe
<220> FEATURE:
<221> NAME/KEY: misc_feature
<222> LOCATION: (3)..(3)
<223> OTHER INFORMATION: Xaa is Thr (main residue from sequencing) or
      Asp
<220> FEATURE:
<221> NAME/KEY: misc_feature
<222> LOCATION: (4)..(4)
<223> OTHER INFORMATION: Xaa is Val (main residue from sequencing) or Ala

<400> SEQUENCE: 20

Xaa Xaa Xaa Xaa
1

<210> SEQ ID NO 21
<211> LENGTH: 7
<212> TYPE: PRT
<213> ORGANISM: Lactobacillus brevis
<220> FEATURE:
<221> NAME/KEY: misc_feature
<222> LOCATION: (1)..(1)
<223> OTHER INFORMATION: Xaa is Ala (main residue from sequencing), Val,
      Ile, Leu, or Ser
<220> FEATURE:
<221> NAME/KEY: misc_feature
<222> LOCATION: (2)..(2)
<223> OTHER INFORMATION: Xaa is Phe (main residue from sequencing) or
      Met
<220> FEATURE:
<221> NAME/KEY: misc_feature
<222> LOCATION: (4)..(4)
<223> OTHER INFORMATION: Xaa is Pro (main residue from sequencing) or
      Gln
<220> FEATURE:
<221> NAME/KEY: misc_feature
<222> LOCATION: (5)..(5)
<223> OTHER INFORMATION: Xaa is Gly (main residue from sequencing) or
      Tyr
<220> FEATURE:
<221> NAME/KEY: misc_feature
<222> LOCATION: (7)..(7)
<223> OTHER INFORMATION: Xaa is Arg (main residue from sequencing) or
      Asn

<400> SEQUENCE: 21

Xaa Xaa Ile Xaa Xaa Lys Xaa
1               5

<210> SEQ ID NO 22
<211> LENGTH: 15
<212> TYPE: PRT
<213> ORGANISM: Lactobacillus brevis
<220> FEATURE:
<221> NAME/KEY: UNSURE
<222> LOCATION: (1)..(1)
<220> FEATURE:
<221> NAME/KEY: misc_feature
<222> LOCATION: (6)..(6)
<223> OTHER INFORMATION: Xaa is unknown
<220> FEATURE:
<221> NAME/KEY: misc_feature
<222> LOCATION: (10)..(15)
<223> OTHER INFORMATION: Xaa is unknown

<400> SEQUENCE: 22

Ser Ala Ala Leu Asp Xaa Ala Leu Lys Xaa Xaa Xaa Xaa Xaa Xaa
1               5                   10                  15

<210> SEQ ID NO 23
<211> LENGTH: 18
<212> TYPE: PRT
<213> ORGANISM: Lactobacillus brevis
<220> FEATURE:
<221> NAME/KEY: misc_feature
<222> LOCATION: (1)..(1)
<223> OTHER INFORMATION: Xaa is Ser (main residue from sequencing) or
      Phe
<220> FEATURE:
<221> NAME/KEY: UNSURE
<222> LOCATION: (2)..(2)
<220> FEATURE:

```
<221> NAME/KEY: misc_feature
<222> LOCATION: (3)..(3)
<223> OTHER INFORMATION: Xaa is Ala (main residue from sequencing) or
      Thr
<220> FEATURE:
<221> NAME/KEY: misc_feature
<222> LOCATION: (4)..(4)
<223> OTHER INFORMATION: Xaa is Leu (main residue from sequencing) or
      Gly
<220> FEATURE:
<221> NAME/KEY: misc_feature
<222> LOCATION: (5)..(5)
<223> OTHER INFORMATION: Xaa is Asp (main residue from sequencing) or
      Ser
<220> FEATURE:
<221> NAME/KEY: misc_feature
<222> LOCATION: (6)..(6)
<223> OTHER INFORMATION: Xaa is unknown or Glu
<220> FEATURE:
<221> NAME/KEY: misc_feature
<222> LOCATION: (7)..(7)
<223> OTHER INFORMATION: Xaa is Ala (main residue from sequencing) or
      Phe
<220> FEATURE:
<221> NAME/KEY: misc_feature
<222> LOCATION: (8)..(8)
<223> OTHER INFORMATION: Xaa is Leu (main residue from sequencing) or
      Val
<220> FEATURE:
<221> NAME/KEY: misc_feature
<222> LOCATION: (9)..(9)
<223> OTHER INFORMATION: Xaa is Lys (main residue from sequencing) or
      Val
<220> FEATURE:
<221> NAME/KEY: misc_feature
<222> LOCATION: (10)..(10)
<223> OTHER INFORMATION: Xaa is Asp (main residue from sequencing) or
      unsure
<220> FEATURE:
<221> NAME/KEY: misc_feature
<222> LOCATION: (11)..(11)
<223> OTHER INFORMATION: Xaa is Tyr (main residue from sequencing) or
      Gly
<220> FEATURE:
<221> NAME/KEY: misc_feature
<222> LOCATION: (12)..(12)
<223> OTHER INFORMATION: Xaa is unknown or Gly
<220> FEATURE:
<221> NAME/KEY: misc_feature
<222> LOCATION: (13)..(13)
<223> OTHER INFORMATION: Xaa is Val (main residue from sequencing) or
      Tyr
<220> FEATURE:
<221> NAME/KEY: misc_feature
<222> LOCATION: (14)..(14)
<223> OTHER INFORMATION: Xaa is Arg (main residue from sequencing) or
      Thr
<220> FEATURE:
<221> NAME/KEY: misc_feature
<222> LOCATION: (15)..(15)
<223> OTHER INFORMATION: Xaa is unknown or Ala
<220> FEATURE:
<221> NAME/KEY: misc_feature
<222> LOCATION: (16)..(16)
<223> OTHER INFORMATION: Xaa is unknown or Gln
<220> FEATURE:
<221> NAME/KEY: misc_feature
<222> LOCATION: (17)..(18)
<223> OTHER INFORMATION: Xaa is unknown

<400> SEQUENCE: 23

Xaa Ala Xaa Xaa Xaa Xaa Xaa Xaa Xaa Asp Xaa Xaa Xaa Xaa Xaa Xaa
1               5                   10                  15

Xaa Xaa

<210> SEQ ID NO 24
```

```
<211> LENGTH: 17
<212> TYPE: PRT
<213> ORGANISM: Lactobacillus brevis
<220> FEATURE:
<221> NAME/KEY: misc_feature
<222> LOCATION: (6)..(6)
<223> OTHER INFORMATION: Xaa is unknown
<220> FEATURE:
<221> NAME/KEY: misc_feature
<222> LOCATION: (10)..(17)
<223> OTHER INFORMATION: Xaa is unknown

<400> SEQUENCE: 24

Ser Ala Ala Leu Asp Xaa Ala Leu Lys Xaa Xaa Xaa Xaa Xaa Xaa Xaa
1               5                   10                  15

Xaa

<210> SEQ ID NO 25
<211> LENGTH: 20
<212> TYPE: PRT
<213> ORGANISM: Lactobacillus brevis
<220> FEATURE:
<221> NAME/KEY: misc_feature
<222> LOCATION: (16)..(20)
<223> OTHER INFORMATION: Xaa is unknown

<400> SEQUENCE: 25

Lys Leu Leu Ala Val Asn Leu Asp Gly Val Phe Phe Gly Thr Arg Xaa
1               5                   10                  15

Xaa Xaa Xaa Xaa
            20

<210> SEQ ID NO 26
<211> LENGTH: 6
<212> TYPE: PRT
<213> ORGANISM: Lactobacillus brevis
<220> FEATURE:
<221> NAME/KEY: misc_feature
<222> LOCATION: (1)..(1)
<223> OTHER INFORMATION: Xaa is unknown
<220> FEATURE:
<221> NAME/KEY: misc_feature
<222> LOCATION: (3)..(3)
<223> OTHER INFORMATION: Xaa is unknown

<400> SEQUENCE: 26

Xaa Met Xaa Thr Gly Arg
1               5

<210> SEQ ID NO 27
<211> LENGTH: 15
<212> TYPE: PRT
<213> ORGANISM: Lactobacillus brevis
<220> FEATURE:
<221> NAME/KEY: misc_feature
<222> LOCATION: (1)..(1)
<223> OTHER INFORMATION: Xaa is Thr (main residue from sequencing), Ser,
      or Phe
<220> FEATURE:
<221> NAME/KEY: misc_feature
<222> LOCATION: (2)..(2)
<223> OTHER INFORMATION: Xaa is Lys (main residue from sequencing) or
      Ala
<220> FEATURE:
<221> NAME/KEY: misc_feature
<222> LOCATION: (3)..(3)
<223> OTHER INFORMATION: Xaa is Thr (main residue from sequencing) or
      Ala
<220> FEATURE:
<221> NAME/KEY: misc_feature
<222> LOCATION: (4)..(4)
```

```
<223> OTHER INFORMATION: Xaa is Phe (main residue from sequencing), Leu,
      or Gly
<220> FEATURE:
<221> NAME/KEY: misc_feature
<222> LOCATION: (5)..(5)
<223> OTHER INFORMATION: Xaa is Met (main residue from sequencing), Asp,
      or Ser
<220> FEATURE:
<221> NAME/KEY: misc_feature
<222> LOCATION: (6)..(6)
<223> OTHER INFORMATION: Xaa is Gly (main residue from sequencing) or
      Glu
<220> FEATURE:
<221> NAME/KEY: misc_feature
<222> LOCATION: (7)..(7)
<223> OTHER INFORMATION: Xaa is His (main residue from sequencing), Ala,
      or Phe
<220> FEATURE:
<221> NAME/KEY: misc_feature
<222> LOCATION: (8)..(8)
<223> OTHER INFORMATION: Xaa is Ile (main residue from sequencing), Leu,
      or Val
<220> FEATURE:
<221> NAME/KEY: MISC_FEATURE
<222> LOCATION: (9)..(9)
<223> OTHER INFORMATION: Xaa is unknown, Lys, or Val
<220> FEATURE:
<221> NAME/KEY: misc_feature
<222> LOCATION: (10)..(10)
<223> OTHER INFORMATION: Xaa is Glu (main residue from sequencing) or
      Asp
<220> FEATURE:
<221> NAME/KEY: misc_feature
<222> LOCATION: (11)..(11)
<223> OTHER INFORMATION: Xaa is Pro (main residue from sequencing), Tyr,
      or Gly
<220> FEATURE:
<221> NAME/KEY: misc_feature
<222> LOCATION: (12)..(12)
<223> OTHER INFORMATION: Xaa is Asn (main residue from sequencing),
      Asp, or Gly
<220> FEATURE:
<221> NAME/KEY: MISC_FEATURE
<222> LOCATION: (13)..(13)
<223> OTHER INFORMATION: Xaa is unknown, Val, or Tyr
<220> FEATURE:
<221> NAME/KEY: misc_feature
<222> LOCATION: (14)..(14)
<223> OTHER INFORMATION: Xaa is Ile (main residue from sequencing),
      Arg, or Thr
<220> FEATURE:
<221> NAME/KEY: misc_feature
<222> LOCATION: (15)..(15)
<223> OTHER INFORMATION: Xaa is Ala (main residue from sequencing) or
      unknown

<400> SEQUENCE: 27

Xaa Xaa Xaa Xaa Xaa Xaa Xaa Xaa Xaa Xaa Xaa Xaa Xaa Xaa Xaa
1               5                   10                  15

<210> SEQ ID NO 28
<211> LENGTH: 20
<212> TYPE: PRT
<213> ORGANISM: Lactobacillus brevis
<220> FEATURE:
<221> NAME/KEY: misc_feature
<222> LOCATION: (1)..(1)
<223> OTHER INFORMATION: Xaa is Thr (main residue from sequencing), Phe,
      or Ser
<220> FEATURE:
<221> NAME/KEY: misc_feature
<222> LOCATION: (2)..(2)
<223> OTHER INFORMATION: Xaa is Lys (main residue from sequencing) or
      Ala
<220> FEATURE:
<221> NAME/KEY: misc_feature
<222> LOCATION: (3)..(3)
```

<223> OTHER INFORMATION: Xaa is Thr (main residue from sequencing) or
      Ala
<220> FEATURE:
<221> NAME/KEY: misc_feature
<222> LOCATION: (4)..(4)
<223> OTHER INFORMATION: Xaa is Pro (main residue from sequencing), Gly,
      or Leu
<220> FEATURE:
<221> NAME/KEY: misc_feature
<222> LOCATION: (5)..(5)
<223> OTHER INFORMATION: Xaa is Met (main residue from sequencing), Ser,
      or Asp
<220> FEATURE:
<221> NAME/KEY: misc_feature
<222> LOCATION: (6)..(6)
<223> OTHER INFORMATION: Xaa is Gly, Glu, or Cys (unsure)
<220> FEATURE:
<221> NAME/KEY: MISC_FEATURE
<222> LOCATION: (7)..(7)
<223> OTHER INFORMATION: Xaa is unknown, Phe, or Ala
<220> FEATURE:
<221> NAME/KEY: misc_feature
<222> LOCATION: (8)..(8)
<223> OTHER INFORMATION: Xaa is Ile (main residue from sequencing), Val,
      or Leu
<220> FEATURE:
<221> NAME/KEY: misc_feature
<222> LOCATION: (9)..(9)
<223> OTHER INFORMATION: Xaa is Ala (unsure) (main residue from
      sequencing), Val, or Lys
<220> FEATURE:
<221> NAME/KEY: misc_feature
<222> LOCATION: (10)..(10)
<223> OTHER INFORMATION: Xaa is Glu (main residue from sequencing) or
      Asp
<220> FEATURE:
<221> NAME/KEY: misc_feature
<222> LOCATION: (11)..(11)
<223> OTHER INFORMATION: Xaa is Pro (unsure) (main residue from
      sequencing), Gly, or Tyr
<220> FEATURE:
<221> NAME/KEY: misc_feature
<222> LOCATION: (12)..(12)
<223> OTHER INFORMATION: Xaa is Asn (unsure) (main residue from
      sequencing), Gly, or Asp
<220> FEATURE:
<221> NAME/KEY: misc_feature
<222> LOCATION: (13)..(13)
<223> OTHER INFORMATION: Xaa is Asp (unsure) (main residue from
      sequencing), Tyr, or Val
<220> FEATURE:
<221> NAME/KEY: misc_feature
<222> LOCATION: (14)..(14)
<223> OTHER INFORMATION: Xaa is Ile (main residue from sequencing), Thr,
      or Arg
<220> FEATURE:
<221> NAME/KEY: misc_feature
<222> LOCATION: (15)..(15)
<223> OTHER INFORMATION: Xaa is Ala (main residue from sequencing) or
      unknown
<220> FEATURE:
<221> NAME/KEY: misc_feature
<222> LOCATION: (16)..(16)
<223> OTHER INFORMATION: Xaa is Tyr or Gln
<220> FEATURE:
<221> NAME/KEY: misc_feature
<222> LOCATION: (17)..(20)
<223> OTHER INFORMATION: Xaa is unknown

<400> SEQUENCE: 28

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 29

```
<211> LENGTH: 25
<212> TYPE: PRT
<213> ORGANISM: Lactobacillus brevis
<220> FEATURE:
<221> NAME/KEY: misc_feature
<222> LOCATION: (1)..(1)
<223> OTHER INFORMATION: Xaa is Lys, Thr, or Gln
<220> FEATURE:
<221> NAME/KEY: misc_feature
<222> LOCATION: (2)..(2)
<223> OTHER INFORMATION: Xaa is Ala or Gly
<220> FEATURE:
<221> NAME/KEY: misc_feature
<222> LOCATION: (3)..(3)
<223> OTHER INFORMATION: Xaa is Ala or Leu
<220> FEATURE:
<221> NAME/KEY: misc_feature
<222> LOCATION: (4)..(4)
<223> OTHER INFORMATION: Xaa is Lys or Phe
<220> FEATURE:
<221> NAME/KEY: misc_feature
<222> LOCATION: (5)..(5)
<223> OTHER INFORMATION: Xaa is Ser, Leu, or Arg
<220> FEATURE:
<221> NAME/KEY: misc_feature
<222> LOCATION: (7)..(7)
<223> OTHER INFORMATION: Xaa is Gly or Val
<220> FEATURE:
<221> NAME/KEY: misc_feature
<222> LOCATION: (8)..(8)
<223> OTHER INFORMATION: Xaa is Thr, Leu, or Val
<220> FEATURE:
<221> NAME/KEY: misc_feature
<222> LOCATION: (9)..(9)
<223> OTHER INFORMATION: Xaa is Pro or Arg
<220> FEATURE:
<221> NAME/KEY: misc_feature
<222> LOCATION: (10)..(10)
<223> OTHER INFORMATION: Xaa is Asp, Val, or Asn
<220> FEATURE:
<221> NAME/KEY: misc_feature
<222> LOCATION: (11)..(11)
<223> OTHER INFORMATION: Xaa is Gln, Ala, or Glu
<220> FEATURE:
<221> NAME/KEY: misc_feature
<222> LOCATION: (12)..(12)
<223> OTHER INFORMATION: Xaa is Ile or Thr
<220> FEATURE:
<221> NAME/KEY: misc_feature
<222> LOCATION: (13)..(13)
<223> OTHER INFORMATION: Xaa is Gln or Val
<220> FEATURE:
<221> NAME/KEY: misc_feature
<222> LOCATION: (15)..(15)
<223> OTHER INFORMATION: Xaa is Phe or Pro
<220> FEATURE:
<221> NAME/KEY: misc_feature
<222> LOCATION: (16)..(16)
<223> OTHER INFORMATION: Xaa is Gln or Gly
<220> FEATURE:
<221> NAME/KEY: misc_feature
<222> LOCATION: (17)..(17)
<223> OTHER INFORMATION: Xaa is His or Tyr
<220> FEATURE:
<221> NAME/KEY: misc_feature
<222> LOCATION: (18)..(18)
<223> OTHER INFORMATION: Xaa is Asp or Ile
<220> FEATURE:
<221> NAME/KEY: misc_feature
<222> LOCATION: (19)..(19)
<223> OTHER INFORMATION: Xaa is Ser, Lys, or Asp
<220> FEATURE:
<221> NAME/KEY: misc_feature
<222> LOCATION: (20)..(20)
<223> OTHER INFORMATION: Xaa is Ser or Ala
<220> FEATURE:
<221> NAME/KEY: misc_feature
<222> LOCATION: (21)..(21)
<223> OTHER INFORMATION: Xaa is Phe or Thr
```

```
<220> FEATURE:
<221> NAME/KEY: misc_feature
<222> LOCATION: (23)..(23)
<223> OTHER INFORMATION: Xaa is Val (unsure) or Ala
<220> FEATURE:
<221> NAME/KEY: misc_feature
<222> LOCATION: (24)..(24)
<223> OTHER INFORMATION: Xaa is Val (unsure) or Asn
<220> FEATURE:
<221> NAME/KEY: UNSURE
<222> LOCATION: (25)..(25)

<400> SEQUENCE: 29

Xaa Xaa Xaa Xaa Xaa Val Xaa Xaa Xaa Xaa Xaa Xaa Xaa Phe Xaa Xaa
1               5                   10                  15

Xaa Xaa Xaa Xaa Xaa Glu Xaa Xaa Gln
            20                  25

<210> SEQ ID NO 30
<211> LENGTH: 20
<212> TYPE: PRT
<213> ORGANISM: Lactobacillus brevis
<220> FEATURE:
<221> NAME/KEY: misc_feature
<222> LOCATION: (1)..(1)
<223> OTHER INFORMATION: Xaa is unknown
<220> FEATURE:
<221> NAME/KEY: misc_feature
<222> LOCATION: (2)..(2)
<223> OTHER INFORMATION: Xaa is Val(main residue from sequencing), Lys,
      or Arg
<220> FEATURE:
<221> NAME/KEY: misc_feature
<222> LOCATION: (5)..(5)
<223> OTHER INFORMATION: Xaa is Leu(main residue from sequencing) or Ala
<220> FEATURE:
<221> NAME/KEY: misc_feature
<222> LOCATION: (10)..(10)
<223> OTHER INFORMATION: Xaa is unknown, Ile, or Asp
<220> FEATURE:
<221> NAME/KEY: misc_feature
<222> LOCATION: (11)..(20)
<223> OTHER INFORMATION: Xaa is unknown

<400> SEQUENCE: 30

Xaa Xaa Lys Leu Xaa Ala Val Asn Leu Xaa Xaa Xaa Xaa Xaa Xaa Xaa
1               5                   10                  15

Xaa Xaa Xaa Xaa
            20

<210> SEQ ID NO 31
<211> LENGTH: 20
<212> TYPE: PRT
<213> ORGANISM: Lactobacillus brevis
<220> FEATURE:
<221> NAME/KEY: misc_feature
<222> LOCATION: (1)..(1)
<223> OTHER INFORMATION: Xaa is Thr or Gly (main residues from
      sequencing), or Val
<220> FEATURE:
<221> NAME/KEY: misc_feature
<222> LOCATION: (3)..(3)
<223> OTHER INFORMATION: Xaa is Phe (main residue from sequencing) or
      Val
<220> FEATURE:
<221> NAME/KEY: misc_feature
<222> LOCATION: (4)..(4)
<223> OTHER INFORMATION: Xaa is Phe (main residue from sequencing) or
      Asn
<220> FEATURE:
<221> NAME/KEY: misc_feature
<222> LOCATION: (5)..(5)
<223> OTHER INFORMATION: Xaa is Gly (unsure) (main residue from
``` sequencing) or Thr
<220> FEATURE:
<221> NAME/KEY: misc_feature
<222> LOCATION: (6)..(6)
<223> OTHER INFORMATION: Xaa is Leu (main residue from sequencing) or
      Val
<220> FEATURE:
<221> NAME/KEY: misc_feature
<222> LOCATION: (7)..(7)
<223> OTHER INFORMATION: Xaa is Lys (main residue from sequencing) or
      His
<220> FEATURE:
<221> NAME/KEY: misc_feature
<222> LOCATION: (8)..(8)
<223> OTHER INFORMATION: Xaa is Gln (main residue from sequencing) or
      Pro
<220> FEATURE:
<221> NAME/KEY: misc_feature
<222> LOCATION: (9)..(9)
<223> OTHER INFORMATION: Xaa is Asn (main residue from sequencing) or
      Gly
<220> FEATURE:
<221> NAME/KEY: misc_feature
<222> LOCATION: (10)..(10)
<223> OTHER INFORMATION: Xaa is Ile (main residue from sequencing) or
      Tyr
<220> FEATURE:
<221> NAME/KEY: misc_feature
<222> LOCATION: (11)..(11)
<223> OTHER INFORMATION: Xaa is Glu (main residue from sequencing) or
      Ile
<220> FEATURE:
<221> NAME/KEY: misc_feature
<222> LOCATION: (12)..(12)
<223> OTHER INFORMATION: Xaa is Asn (main residue from sequencing), Lys,
      or Asp
<220> FEATURE:
<221> NAME/KEY: misc_feature
<222> LOCATION: (13)..(13)
<223> OTHER INFORMATION: Xaa is Ile (main residue from sequencing) or
      Thr
<220> FEATURE:
<221> NAME/KEY: misc_feature
<222> LOCATION: (14)..(14)
<223> OTHER INFORMATION: Xaa is Asn (main residue from sequencing) or
      Pro
<220> FEATURE:
<221> NAME/KEY: misc_feature
<222> LOCATION: (15)..(15)
<223> OTHER INFORMATION: Xaa is Ile or Asn (main residues from
      sequencing), or Leu
<220> FEATURE:
<221> NAME/KEY: misc_feature
<222> LOCATION: (16)..(16)
<223> OTHER INFORMATION: Xaa is Ala (main residue from sequencing), Met,
      Gly, or Val
<220> FEATURE:
<221> NAME/KEY: misc_feature
<222> LOCATION: (17)..(17)
<223> OTHER INFORMATION: Xaa is Ala (main residue from sequencing) or
      Asp
<220> FEATURE:
<221> NAME/KEY: misc_feature
<222> LOCATION: (18)..(18)
<223> OTHER INFORMATION: Xaa is Val (main residue from sequencing) or
      Asp
<220> FEATURE:
<221> NAME/KEY: misc_feature
<222> LOCATION: (19)..(19)
<223> OTHER INFORMATION: Xaa is Arg (main residue from sequencing), Asp,
      or Leu
<220> FEATURE:
<221> NAME/KEY: Unsure
<222> LOCATION: (20)..(20)

<400> SEQUENCE: 31

Xaa Val Xaa Xaa Xaa Xaa Xaa Xaa Xaa Xaa Xaa Xaa Xaa Xaa Xaa Xaa
 1               5                  10                  15

Xaa Xaa Xaa Pro
            20

<210> SEQ ID NO 32
<211> LENGTH: 30
<212> TYPE: PRT
<213> ORGANISM: Lactobacillus brevis
<220> FEATURE:
<221> NAME/KEY: misc_feature
<222> LOCATION: (1)..(1)
<223> OTHER INFORMATION: Xaa is Gly (main residue from sequencing), Gln,
      Thr, or Pro
<220> FEATURE:
<221> NAME/KEY: misc_feature
<222> LOCATION: (2)..(2)
<223> OTHER INFORMATION: Xaa is Phe (main residue from sequencing), Val,
      or Ser
<220> FEATURE:
<221> NAME/KEY: misc_feature
<222> LOCATION: (3)..(3)
<223> OTHER INFORMATION: Xaa is Val (main residue from sequencing) or
      Leu
<220> FEATURE:
<221> NAME/KEY: misc_feature
<222> LOCATION: (5)..(5)
<223> OTHER INFORMATION: Xaa is Asp (main residue from sequencing), Ala,
      or Ile
<220> FEATURE:
<221> NAME/KEY: misc_feature
<222> LOCATION: (6)..(6)
<223> OTHER INFORMATION: Xaa is Pro (main residue from sequencing), Gln,
      or Tyr
<220> FEATURE:
<221> NAME/KEY: misc_feature
<222> LOCATION: (7)..(7)
<223> OTHER INFORMATION: Xaa is Ser (main residue from sequencing), Asn,
      Arg, or Lys
<220> FEATURE:
<221> NAME/KEY: misc_feature
<222> LOCATION: (8)..(8)
<223> OTHER INFORMATION: Xaa is Leu (main residue from sequencing), Met,
      or Ala
<220> FEATURE:
<221> NAME/KEY: misc_feature
<222> LOCATION: (9)..(9)
<223> OTHER INFORMATION: Xaa is Gly (main residue from sequencing) or
      Lys
<220> FEATURE:
<221> NAME/KEY: misc_feature
<222> LOCATION: (10)..(10)
<223> OTHER INFORMATION: Xaa is Ala (main residue from sequencing), Asn,
      or Lys
<220> FEATURE:
<221> NAME/KEY: misc_feature
<222> LOCATION: (11)..(11)
<223> OTHER INFORMATION: Xaa is Tyr (main residue from sequencing), Gly,
      or Lys
<220> FEATURE:
<221> NAME/KEY: misc_feature
<222> LOCATION: (12)..(12)
<223> OTHER INFORMATION: Xaa is Asn (main residue from sequencing), Gly,
      or Ala
<220> FEATURE:
<221> NAME/KEY: misc_feature
<222> LOCATION: (13)..(13)
<223> OTHER INFORMATION: Xaa is Ala (main residue from sequencing), Leu,
      or Val
<220> FEATURE:
<221> NAME/KEY: misc_feature
<222> LOCATION: (14)..(14)
<223> OTHER INFORMATION: Xaa is Gly (main residue from sequencing), Ser,
      or Arg
<220> FEATURE:
<221> NAME/KEY: misc_feature
<222> LOCATION: (15)..(15)
<223> OTHER INFORMATION: Xaa is Lys (main residue from sequencing), Ala,
      or Ile

```
<220> FEATURE:
<221> NAME/KEY: misc_feature
<222> LOCATION: (16)..(16)
<223> OTHER INFORMATION: Xaa is Gly (main residue from sequencing), Met,
      or Ser
<220> FEATURE:
<221> NAME/KEY: misc_feature
<222> LOCATION: (17)..(17)
<223> OTHER INFORMATION: Xaa is Ala (main residue from sequencing) or
      Ile
<220> FEATURE:
<221> NAME/KEY: misc_feature
<222> LOCATION: (18)..(18)
<223> OTHER INFORMATION: Xaa is Val (main residue from sequencing) or
      Lys
<220> FEATURE:
<221> NAME/KEY: misc_feature
<222> LOCATION: (19)..(19)
<223> OTHER INFORMATION: Xaa is Arg (main residue from sequencing) or
      Asn
<220> FEATURE:
<221> NAME/KEY: misc_feature
<222> LOCATION: (20)..(20)
<223> OTHER INFORMATION: Xaa is Ile (main residue from sequencing), Met,
      or Ala
<220> FEATURE:
<221> NAME/KEY: UNSURE
<222> LOCATION: (28)..(28)
<220> FEATURE:
<221> NAME/KEY: misc_feature
<222> LOCATION: (29)..(30)
<223> OTHER INFORMATION: Xaa is unknown

<400> SEQUENCE: 32

Xaa Xaa Xaa Gly Xaa Xaa Xaa Xaa Xaa Xaa Xaa Xaa Xaa Xaa Xaa Xaa
1               5                   10                  15

Xaa Xaa Xaa Xaa Met Ser Lys Ser Ala Ala Leu Asp Xaa Xaa
            20                  25                  30

<210> SEQ ID NO 33
<211> LENGTH: 10
<212> TYPE: PRT
<213> ORGANISM: Lactobacillus brevis
<220> FEATURE:
<221> NAME/KEY: misc_feature
<222> LOCATION: (5)..(10)
<223> OTHER INFORMATION: Xaa is unknown

<400> SEQUENCE: 33

Phe Val Val Asp Xaa Xaa Xaa Xaa Xaa Xaa
1               5                   10

<210> SEQ ID NO 34
<211> LENGTH: 20
<212> TYPE: PRT
<213> ORGANISM: Lactobacillus brevis
<220> FEATURE:
<221> NAME/KEY: misc_feature
<222> LOCATION: (1)..(1)
<223> OTHER INFORMATION: Xaa is Asp (main residue from sequencing) or
      Arg
<220> FEATURE:
<221> NAME/KEY: misc_feature
<222> LOCATION: (2)..(2)
<223> OTHER INFORMATION: Xaa is Gly (main residue from sequencing), Lys,
      or Tyr
<220> FEATURE:
<221> NAME/KEY: MISC_FEATURE
<222> LOCATION: (3)..(3)
<223> OTHER INFORMATION: Xaa is unknown, Leu (unsure), or Phe (unsure)
<220> FEATURE:
<221> NAME/KEY: misc_feature
<222> LOCATION: (4)..(4)
<223> OTHER INFORMATION: Xaa is Thr (main residue from sequencing) or
```

Lys

<220> FEATURE:
<221> NAME/KEY: misc_feature
<222> LOCATION: (5)..(5)
<223> OTHER INFORMATION: Xaa is  Lys (main residue from sequencing),
      Asp, or Pro
<220> FEATURE:
<221> NAME/KEY: misc_feature
<222> LOCATION: (6)..(6)
<223> OTHER INFORMATION: Xaa is Leu (main residue from sequencing) or
      Ala
<220> FEATURE:
<221> NAME/KEY: misc_feature
<222> LOCATION: (8)..(8)
<223> OTHER INFORMATION: Xaa is Asp (main residue from sequencing) or
      Glu
<220> FEATURE:
<221> NAME/KEY: misc_feature
<222> LOCATION: (9)..(9)
<223> OTHER INFORMATION: Xaa is Ala (main residue from sequencing) or
      Asp
<220> FEATURE:
<221> NAME/KEY: UNSURE
<222> LOCATION: (12)..(12)
<220> FEATURE:
<221> NAME/KEY: misc_feature
<222> LOCATION: (13)..(20)
<223> OTHER INFORMATION: Xaa is unknown

<400> SEQUENCE: 34

Xaa Xaa Xaa Xaa Xaa Xaa Phe Xaa Xaa Thr Glu Glu Xaa Xaa Xaa Xaa
1               5                   10                  15

Xaa Xaa Xaa Xaa
            20

<210> SEQ ID NO 35
<211> LENGTH: 14
<212> TYPE: PRT
<213> ORGANISM: Lactobacillus brevis
<220> FEATURE:
<221> NAME/KEY: misc_feature
<222> LOCATION: (11)..(14)
<223> OTHER INFORMATION: Xaa is unknown

<400> SEQUENCE: 35

Phe Val Val Asp Gly Gly Tyr Thr Ala Gln Xaa Xaa Xaa Xaa
1               5                   10

<210> SEQ ID NO 36
<211> LENGTH: 30
<212> TYPE: PRT
<213> ORGANISM: Lactobacillus brevis
<220> FEATURE:
<221> NAME/KEY: misc_feature
<222> LOCATION: (1)..(1)
<223> OTHER INFORMATION: Xaa is unknown
<220> FEATURE:
<221> NAME/KEY: misc_feature
<222> LOCATION: (2)..(2)
<223> OTHER INFORMATION: Xaa is Ala (main residue from sequencing) or
      Ser
<220> FEATURE:
<221> NAME/KEY: misc_feature
<222> LOCATION: (24)..(24)
<223> OTHER INFORMATION: Xaa is Val (unsure) (main residue from
      sequencing) or Asp
<220> FEATURE:
<221> NAME/KEY: misc_feature
<222> LOCATION: (30)..(30)
<223> OTHER INFORMATION: Xaa is Glu (main residue from sequencing) or
      Gly (unsure)

<400> SEQUENCE: 36

```
Xaa Xaa Leu Lys Asp Tyr Asp Val Arg Val Asn Thr Val His Pro Gly
1               5                   10                  15

Tyr Ile Lys Thr Pro Leu Val Xaa Asp Leu Pro Gly Ala Xaa
            20                  25                  30
```

<210> SEQ ID NO 37
<211> LENGTH: 15
<212> TYPE: PRT
<213> ORGANISM: Lactobacillus brevis

<400> SEQUENCE: 37

```
Lys Ala Ala Lys Ser Val Gly Thr Pro Asp Gln Ile Gln Phe Phe
1               5                   10                  15
```

<210> SEQ ID NO 38
<211> LENGTH: 13
<212> TYPE: PRT
<213> ORGANISM: Lactobacillus brevis

<400> SEQUENCE: 38

```
Gly Ala Lys Val Met Ile Thr Gly Arg His Ser Asp Val
1               5                   10
```

<210> SEQ ID NO 39
<211> LENGTH: 10
<212> TYPE: PRT
<213> ORGANISM: Lactobacillus brevis
<220> FEATURE:
<221> NAME/KEY: misc_feature
<222> LOCATION: (1)..(1)
<223> OTHER INFORMATION: Xaa is Ser (main residue from sequencing) or
      Ala
<220> FEATURE:
<221> NAME/KEY: misc_feature
<222> LOCATION: (3)..(3)
<223> OTHER INFORMATION: Xaa is Phe (main residue from sequencing) or
      Gly
<220> FEATURE:
<221> NAME/KEY: misc_feature
<222> LOCATION: (5)..(5)
<223> OTHER INFORMATION: Xaa is Thr (main residue from sequencing), Phe,
      or Ile
<220> FEATURE:
<221> NAME/KEY: misc_feature
<222> LOCATION: (6)..(6)
<223> OTHER INFORMATION: Xaa is Gly (main residue from sequencing) or
      Val
<220> FEATURE:
<221> NAME/KEY: misc_feature
<222> LOCATION: (7)..(7)
<223> OTHER INFORMATION: Xaa is Ser (main residue from sequencing) or
      Tyr
<220> FEATURE:
<221> NAME/KEY: misc_feature
<222> LOCATION: (8)..(8)
<223> OTHER INFORMATION: Xaa is Glu (main residue from sequencing) or
      Leu

<400> SEQUENCE: 39

```
Xaa Lys Xaa Ala Xaa Xaa Xaa Xaa Phe Val
1               5                   10
```

<210> SEQ ID NO 40
<211> LENGTH: 25
<212> TYPE: PRT
<213> ORGANISM: Lactobacillus brevis
<220> FEATURE:
<221> NAME/KEY: misc_feature
<222> LOCATION: (1)..(1)
<223> OTHER INFORMATION: Xaa is unknown
<220> FEATURE:

```
<221> NAME/KEY: misc_feature
<222> LOCATION: (2)..(2)
<223> OTHER INFORMATION: Xaa is Asp (main residue from sequencing), Val,
      Ser, or Leu
<220> FEATURE:
<221> NAME/KEY: misc_feature
<222> LOCATION: (3)..(3)
<223> OTHER INFORMATION: Xaa is Val (main residue from sequencing), Phe,
      or Leu
<220> FEATURE:
<221> NAME/KEY: misc_feature
<222> LOCATION: (4)..(4)
<223> OTHER INFORMATION: Xaa is Arg (main residue from sequencing), Lys,
      or Gly
<220> FEATURE:
<221> NAME/KEY: misc_feature
<222> LOCATION: (5)..(5)
<223> OTHER INFORMATION: Xaa is Val (main residue from sequencing), Ile,
      Ala, or Gly
<220> FEATURE:
<221> NAME/KEY: misc_feature
<222> LOCATION: (14)..(14)
<223> OTHER INFORMATION: Xaa is Lys (main residue from sequencing) or
      Gly
<220> FEATURE:
<221> NAME/KEY: misc_feature
<222> LOCATION: (15)..(15)
<223> OTHER INFORMATION: Xaa is Thr (main residue from sequencing) or
      Ala
<220> FEATURE:
<221> NAME/KEY: misc_feature
<222> LOCATION: (19)..(19)
<223> OTHER INFORMATION: Xaa is Asp (main residue from sequencing) or
      Asn
<220> FEATURE:
<221> NAME/KEY: misc_feature
<222> LOCATION: (20)..(20)
<223> OTHER INFORMATION: Xaa is Asp (main residue from sequencing) or
      Met
<220> FEATURE:
<221> NAME/KEY: misc_feature
<222> LOCATION: (22)..(22)
<223> OTHER INFORMATION: Xaa is Pro (main residue from sequencing) or
      Leu

<400> SEQUENCE: 40

Xaa Xaa Xaa Xaa Xaa Asn Thr Val His Pro Gly Tyr Ile Xaa Xaa Pro
1               5                   10                  15

Leu Val Xaa Xaa Leu Xaa Gly Ala Glu
            20                  25

<210> SEQ ID NO 41
<211> LENGTH: 40
<212> TYPE: PRT
<213> ORGANISM: Lactobacillus brevis
<220> FEATURE:
<221> NAME/KEY: misc_feature
<222> LOCATION: (2)..(2)
<223> OTHER INFORMATION: Xaa is unknown
<220> FEATURE:
<221> NAME/KEY: UNSURE
<222> LOCATION: (36)..(38)
<220> FEATURE:
<221> NAME/KEY: misc_feature
<222> LOCATION: (39)..(40)
<223> OTHER INFORMATION: Xaa is unknown

<400> SEQUENCE: 41

Trp Xaa Lys Leu Leu Ala Val Asn Leu Asp Gly Val Phe Phe Gly Thr
1               5                   10                  15

Arg Leu Gly Ile Gln Arg Met Lys Asn Lys Gly Leu Gly Ala Ser Ile
            20                  25                  30

Ile Asn Met Ser Ser Ile Xaa Xaa
```

```
<210> SEQ ID NO 42
<211> LENGTH: 40
<212> TYPE: PRT
<213> ORGANISM: Lactobacillus brevis
<220> FEATURE:
<221> NAME/KEY: UNSURE
<222> LOCATION: (1)..(1)
<220> FEATURE:
<221> NAME/KEY: misc_feature
<222> LOCATION: (3)..(3)
<223> OTHER INFORMATION: Xaa is Ser (main residue from sequencing), Lys,
      or Ala
<220> FEATURE:
<221> NAME/KEY: misc_feature
<222> LOCATION: (4)..(4)
<223> OTHER INFORMATION: Xaa is Gln (main residue from sequencing), Leu,
      Lys, or Glu
<220> FEATURE:
<221> NAME/KEY: misc_feature
<222> LOCATION: (5)..(5)
<223> OTHER INFORMATION: Xaa is Arg (main residue from sequencing), Leu,
      or Ser
<220> FEATURE:
<221> NAME/KEY: misc_feature
<222> LOCATION: (6)..(6)
<223> OTHER INFORMATION: Xaa is Thr (main residue from sequencing), Ala,
      or Val
<220> FEATURE:
<221> NAME/KEY: misc_feature
<222> LOCATION: (7)..(7)
<223> OTHER INFORMATION: Xaa is Lys (main residue from sequencing), Val,
      or Gly
<220> FEATURE:
<221> NAME/KEY: misc_feature
<222> LOCATION: (8)..(8)
<223> OTHER INFORMATION: Xaa is Thr (main residue from sequencing) or
      Asn
<220> FEATURE:
<221> NAME/KEY: misc_feature
<222> LOCATION: (9)..(9)
<223> OTHER INFORMATION: Xaa is Pro (main residue from sequencing) or
      Leu
<220> FEATURE:
<221> NAME/KEY: misc_feature
<222> LOCATION: (10)..(10)
<223> OTHER INFORMATION: Xaa is Met (main residue from sequencing), Asp,
      or Ala
<220> FEATURE:
<221> NAME/KEY: misc_feature
<222> LOCATION: (11)..(11)
<223> OTHER INFORMATION: Xaa is Gly (main residue from sequencing), Gln,
      or Tyr
<220> FEATURE:
<221> NAME/KEY: misc_feature
<222> LOCATION: (12)..(12)
<223> OTHER INFORMATION: Xaa is His (main residue from sequencing), Val,
      Ile, or Asn
<220> FEATURE:
<221> NAME/KEY: misc_feature
<222> LOCATION: (13)..(13)
<223> OTHER INFORMATION: Xaa is Ile (main residue from sequencing), Phe,
      Ala, or Gln
<220> FEATURE:
<221> NAME/KEY: misc_feature
<222> LOCATION: (14)..(14)
<223> OTHER INFORMATION: Xaa is Gly (unsure) (main residue from
      sequencing) or Phe
<220> FEATURE:
<221> NAME/KEY: misc_feature
<222> LOCATION: (15)..(15)
<223> OTHER INFORMATION: Xaa is Glu (main residue from sequencing) or
      Gly
<220> FEATURE:
<221> NAME/KEY: misc_feature
<222> LOCATION: (16)..(16)
<223> OTHER INFORMATION: Xaa is Pro (main residue from sequencing) or
```

```
                Thr
<220> FEATURE:
<221> NAME/KEY: misc_feature
<222> LOCATION: (17)..(17)
<223> OTHER INFORMATION: Xaa is Asn (main residue from sequencing) or
      Arg
<220> FEATURE:
<221> NAME/KEY: misc_feature
<222> LOCATION: (18)..(18)
<223> OTHER INFORMATION: Xaa is Asp (main residue from sequencing) or
      Leu
<220> FEATURE:
<221> NAME/KEY: misc_feature
<222> LOCATION: (19)..(19)
<223> OTHER INFORMATION: Xaa is Ile (main residue from sequencing) or
      Gly
<220> FEATURE:
<221> NAME/KEY: misc_feature
<222> LOCATION: (20)..(20)
<223> OTHER INFORMATION: Xaa is Ala (main residue from sequencing) or
      Ile
<220> FEATURE:
<221> NAME/KEY: misc_feature
<222> LOCATION: (21)..(21)
<223> OTHER INFORMATION: Xaa is Tyr (main residue from sequencing) or
      Gln
<220> FEATURE:
<221> NAME/KEY: misc_feature
<222> LOCATION: (25)..(25)
<223> OTHER INFORMATION: Xaa is Tyr (main residue from sequencing) or
      Asn
<220> FEATURE:
<221> NAME/KEY: misc_feature
<222> LOCATION: (27)..(27)
<223> OTHER INFORMATION: Xaa is Ala (main residue from sequencing) or
      Gly
<220> FEATURE:
<221> NAME/KEY: misc_feature
<222> LOCATION: (37)..(39)
<223> OTHER INFORMATION: Xaa is unknown

<400> SEQUENCE: 42

Ala Met Xaa Xaa Xaa Xaa Xaa Xaa Xaa Xaa Xaa Xaa Xaa Xaa Xaa Xaa
1               5                   10                  15

Xaa Xaa Xaa Xaa Xaa Arg Met Lys Xaa Lys Xaa Leu Gly Ala Ser Ile
            20                  25                  30

Ile Asn Met Ser Xaa Xaa Xaa Gly
        35                  40

<210> SEQ ID NO 43
<211> LENGTH: 15
<212> TYPE: PRT
<213> ORGANISM: Lactobacillus brevis
<220> FEATURE:
<221> NAME/KEY: misc_feature
<222> LOCATION: (12)..(15)
<223> OTHER INFORMATION: Xaa is unknown

<400> SEQUENCE: 43

Ser Lys Phe Ala Thr Gly Ser Glu Phe Val Val Xaa Xaa Xaa Xaa
1               5                   10                  15

<210> SEQ ID NO 44
<211> LENGTH: 15
<212> TYPE: PRT
<213> ORGANISM: Lactobacillus brevis
<220> FEATURE:
<221> NAME/KEY: misc_feature
<222> LOCATION: (1)..(1)
<223> OTHER INFORMATION: Xaa is Ser (main residue from sequencing), Ala,
      Phe, or Val
<220> FEATURE:
<221> NAME/KEY: misc_feature
```

```
<222> LOCATION: (4)..(4)
<223> OTHER INFORMATION: Xaa is Ala (main residue from sequencing) or
      Thr
<220> FEATURE:
<221> NAME/KEY: misc_feature
<222> LOCATION: (5)..(5)
<223> OTHER INFORMATION: Xaa is Thr (main residue from sequencing), Ile,
      or Pro
<220> FEATURE:
<221> NAME/KEY: misc_feature
<222> LOCATION: (6)..(6)
<223> OTHER INFORMATION: Xaa is Gly (main residue from sequencing), Leu,
      or Asp
<220> FEATURE:
<221> NAME/KEY: misc_feature
<222> LOCATION: (7)..(7)
<223> OTHER INFORMATION: Xaa is Ser (main residue from sequencing) or
      Gln
<220> FEATURE:
<221> NAME/KEY: misc_feature
<222> LOCATION: (8)..(8)
<223> OTHER INFORMATION: Xaa is Glu (main residue from sequencing) or
      Ile
<220> FEATURE:
<221> NAME/KEY: misc_feature
<222> LOCATION: (9)..(9)
<223> OTHER INFORMATION: Xaa is Phe (main residue from sequencing) or
      Gln
<220> FEATURE:
<221> NAME/KEY: misc_feature
<222> LOCATION: (11)..(11)
<223> OTHER INFORMATION: Xaa is Val (main residue from sequencing), Leu,
      or Ser
<220> FEATURE:
<221> NAME/KEY: misc_feature
<222> LOCATION: (12)..(12)
<223> OTHER INFORMATION: Xaa is Asp (main residue from sequencing), Gln,
      or Lys
<220> FEATURE:
<221> NAME/KEY: misc_feature
<222> LOCATION: (13)..(15)
<223> OTHER INFORMATION: Xaa is unknown

<400> SEQUENCE: 44

Xaa Lys Phe Xaa Xaa Xaa Xaa Xaa Xaa Val Xaa Xaa Xaa Xaa Xaa
1               5                   10                  15
```

METHODS FOR THE PRODUCTION OF 3-METHYLAMINO-1-(THIENE-2-YL)-PROPANE-1-OL

RELATED APPLICATIONS

This application is a national stage application (under 35 U.S.C. 371) of PCT/EP2004/010939 filed Sep. 30, 2004 which claims benefit to German application 103 45 772.0 filed Oct. 1, 2003.

BACKGROUND OF THE INVENTION

Methods for the production of 3-methylamino-1-(thiene-2-yl)propane-1-ol

The present invention relates to a process for preparing 3-methylamino-1-(thien-2-yl)propan-1-ol of the formula I

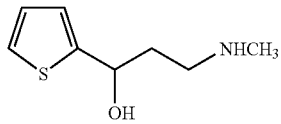

(I)

and, in particular, to a process for preparing the S-enantiomer I-S.

The S enantiomer of the aminopropanol I of the formula I-S

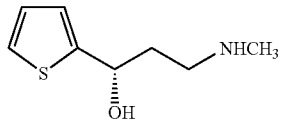

(I-S)

is an important precursor for synthesizing the antidepressant duloxetine of the formula II

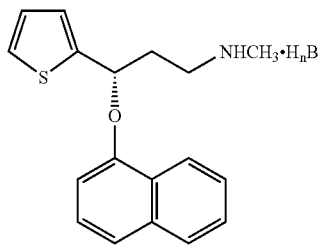

(II)

in which B is an n-fold negatively charged inorganic or organic acid radical and $H_nB$ is a pharmaceutically tolerated acid.

Methods of the prior art for preparing duloxetine or its corresponding base are elaborate and necessitate the use of chiral reagents or chiral starting compounds.

Thus, EP-B-0273658 describes a method for preparing the corresponding base of duloxetine by reacting 2-acetylthiophene in a Mannich reaction with formaldehyde and dimethylamine, reducing the keto group of the resulting Mannich base to give racemic (S)-3-N,N-dimethylamino-1-(thien-2-yl)propan-1-ol, etherifying the alcohol function with naphthyl fluoride and finally converting the dimethylamino group into a methylamino function. The desired enantiomer of the naphthyl ether is obtained by means of using chiral starting materials or by means of racemate resolution at the step of the end product, for example by way of the salts with optically active acids or by way of chromatography on a chiral stationary phase.

U.S. Pat. No. 5,362,886 describes an analogous method in which S-mandelic acid is added to the racemic propanol which is obtained after reduction of the keto group. The S enantiomer of the alcohol which is obtained in this connection is used in the subsequent reaction steps.

EP-A-0457559 also describes a method which is analogous to that in EP-B-0273658. In this case, the keto group of the Mannich base is reduced using the asymmetric reducing system LAH-Icb (lithium aluminum hydride-[(2R,2S)-(−)-4-dimethylamino-1,2-diphenyl-3-methyl-2-butanol]) to give the alcohol in the form of the S enantiomer. Apart from the costs, a disadvantage of this method is the lability of the reducing system LAH-Icb, which is only stable for a few minutes.

In Journal of Labelled Compounds and Radiopharmaceuticals, volume XXXVI, No. 3, pages 213 to 223, W. J. Wheeler and F. Kuo also describe a method for preparing duloxetine. In this method, thiophene-2-carbonyl chloride is reacted, in a Stille coupling, with vinyl tri-n-butylstannane in the presence of catalytic quantities of benzyl(chloro)-bis(triphenylphosphine)palladium(II) in DMPU (dimethylpropyleneurea) to give 1-(thien-2-yl)propenone of the formula II

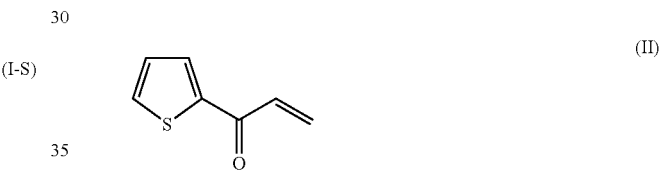

(II)

which is subsequently converted, by treatment with hydrogen chloride, into 3-chloro-1-(thien-2-yl)propan-1-one of the formula III.1

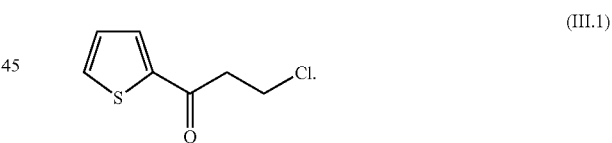

(III.1)

The chloropropanone III.1 which is obtained in this way is subsequently reduced, using a chiral oxazaborolidine and $BH_3$, to give (S)-3-chloro-1-(thien-2-yl)propan-1-ol of the formula IV.1-S

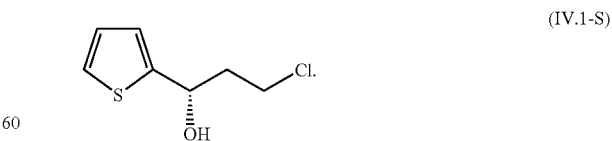

(IV.1-S)

The alcohol IV.1-S which is obtained in this way is converted, by successively reacting with sodium iodide and then with methylamine, into (S)-3-methylamino-1-(thien-2-yl)propan-1-ol I-S. By subsequently successively reacting with sodium hydride, 1-fluoronaphthalene and hydrogen chloride, duloxetine is obtained in the form of the hydrochloride. In this connection, it is disadvantageous, in the first place, that numerous steps and expensive reagents are required for preparing the chloropropanone intermediate III.1. In the second place, the chloropropanol IV.1-S is isolated when the chloropropanone III.1 is converted into the amino alcohol. However, investigations carried out by the applicant have shown that this chloropropanol is labile and very readily decomposes in a strongly exothermic reaction, something which not only leads to yield losses as regards the amino alcohol but also makes it more difficult to manage the reaction on an industrial scale.

Methods for preparing the 3-chloro-1-(thien-2-yl)propan-1-one, which is described by W. J. Wheeler et al. and which arises as an intermediate during the synthesis of duloxetine, are known from the literature. However, a disadvantage of the known methods from the prior art is that either the chloropropanone III.1 is formed in poor yield or that it is necessary to use reagents which are difficult to handle. Thus, in CR Acad. Sci., Ser. C, 1979, 288 (1), 49-52, A. Etienne et al. describe the preparation of the chloropropanone III.1 by means of the Friedel-Crafts reaction of thiophene with 3-chloropropionyl chloride in the presence of aluminum trichloride, as a Lewis acid catalyst, and in nitromethane as solvent. The chloropropanone III.1 is obtained in a yield of only 7%. The corresponding reaction, as described by Liu et al. in Chirality, 12, 26-29 (2000), in the presence of tin tetrachloride, as the Lewis acid catalyst and benzene, as solvent, also results in an unsatisfactory yield. In Acta Chem. Scand. B 20 (6), 1577-1587 (1966), Meth-Cohn et al. describe the corresponding Friedel-Crafts acylation on thiophene in the presence of iron trichloride or aluminum trichloride, with the chloropropanone III.1 being formed in moderate to good yields. A disadvantage of this method is that carbon disulfide has to be used as solvent.

In Tetrahedron Lett. 44, 2003, 4783-4787, Kamal, G. B. R. Khanna, R. Ramu and T. Krishnaji describe the preparation of the duloxetine precursor (S)-3-hydroxy-3-(thien-2-yl)propanenitrile by means of acetylating thiophene with chloroacetyl chloride, reducing the ketone with sodium borohydride to give the racemic alcohol, replacing the chlorine radical with cyanide and reacting the racemic nitrile alcohol with vinyl acetate in the presence of a *Pseudomonas* cepacia lipase (immobilized on diatomite), with the lipase selectively catalyzing the esterification of the R enantiomer, such that the desired S enantiomer, which remains unesterified, can be isolated in pure form. Disadvantages in this connection are, on the one hand, the large number of reaction steps which are required and, on the other hand, the loss of half of the nitrile alcohol since the esterified R moiety is not further reacted to give duloxetine.

BRIEF SUMMARY OF THE INVENTION

It is therefore an object of the present invention to provide a process for preparing 3-methylamino-1-(thien-2-yl)propan-1-ol I which overcomes the above-described disadvantages of the prior art. Furthermore, this process should furnish compound I in good overall yield and, in particular, also make it possible to prepare the S enantiomer I-S enantioselectively.

We have found that this object is achieved by first of all reacting thiophene, in a Friedel-Crafts reaction, with a β-halopropionyl halide or an acryloyl halide in the presence of a Lewis acid, with a hydrogen halide being passed in before the reaction product is isolated. After that, the keto group of the resulting 3-halo-1-(thien-2-yl)-propan-1-one of the formula III

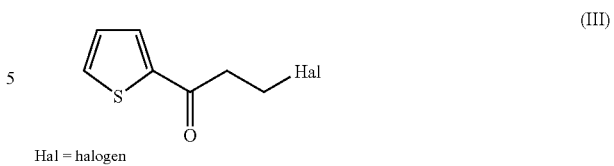

Hal = halogen is reduced and the reduced product of the formula IV

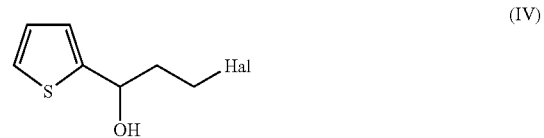

is reacted with methylamine.

The present invention therefore relates to a process for preparing 3-methylamino-1-(thien-2-yl)propan-1-ol of the formula I

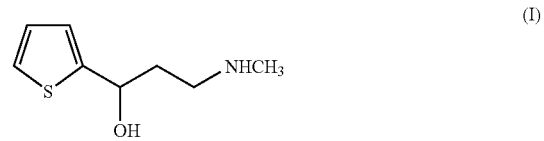

wherein
a) thiophene is reacted with a β-halopropionyl halide or an acryloyl halide, in the presence of a Lewis acid to give a 3-halo-1-(thien-2-yl)propan-1-one, with a hydrogen halide being passed in simultaneously or after the reaction has taken place, but before the reaction product is isolated, and
b) the propanone which is obtained in step a) is reduced and then, preferably without isolating the reaction product, reacted with methylamine.

The process according to the invention furnishes the target compound I in good overall yield. Furthermore, the preparation of the halopropanone intermediate III is not coupled to using expensive organotin reagents. There is no need to isolate the halopropanol IV, which is difficult to handle. In addition, the method makes it possible to enantioselectively prepare the S enantiomer I-S in a simple manner by means of reducing the halopropenone intermediate III in the presence of a chiral catalyst or a chiral reducing agent which exhibit selectivity with regard to the formation of (S)-3-halo-1-(thien-2-yl)propan-1-ol I-S.

BRIEF DESCRIPTION OF THE FIGURES

FIG. 3A shows the result of the N-terminal sequencing of a blot band of Lu10288 dehydrogenase which was isolated in accordance with the invention; and FIG. 3B shows the sequencing data for different proteolytic fragments of an Lu10288 dehydrogenase which was purified in accordance with the invention.

DETAILED DESCRIPTION OF THE INVENTION

Figure 1:
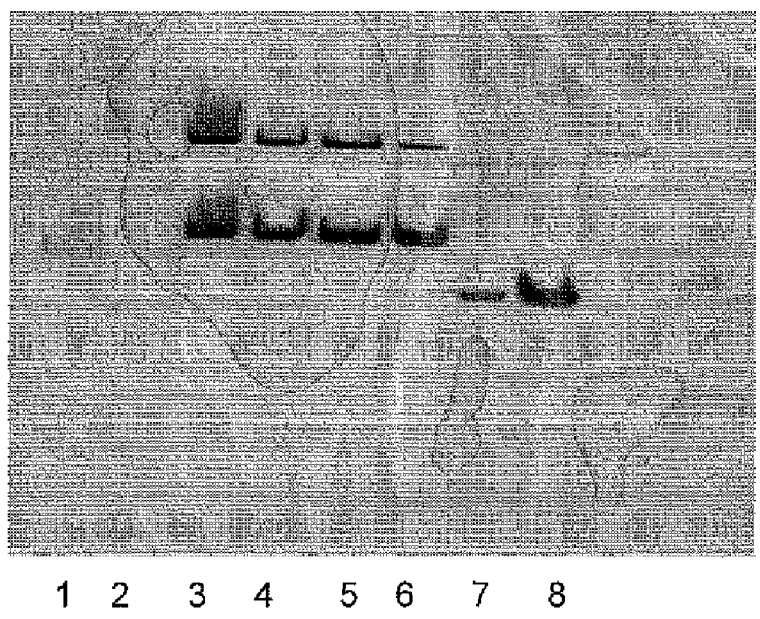
FIG. 1 shows the activity-stained gel for an Lu10288 dehydrogenase which was isolated in accordance with the invention; lane 1: molecular weight standards, from the bottom: 47 kDa, 74 kDa, 121 kDa and 205 kDa; lane 2: empty; lane 3: homogenate supernatant; lane 4: Q Sepharose useful fraction; lane 5: Q Sepharose useful fraction (three-fold quantity); lane 6: Superdex useful fraction; lane 7: Mono-Q useful fraction; lane 8: Mono-P useful fraction.

In the context of the present invention, "enantioselectivity" means that the enantiomeric excess ee (in %) of the S enantiomer, which is calculated, in a known manner, in accordance with:

$$ee(\%)=[S \text{ enantiomer}-R \text{ enantiomer}/(S \text{ enantiomer}-R \text{ enantiomer})]\times 100,$$

is at least 50%, preferably at least 80%, in particular at least 90% and, especially, at least 95%.

As a result of passing in a hydrogen halide during acylation, or preferably after acylation has taken place, but before the reaction product is isolated, essentially no 1-thien-2-yl-propenone II, which always arises as a by-product in the methods of the prior art and diminishes the yield of desired acylation product III, is obtained as an end product of step a).

Covalent metal halides and semimetal halides which have an electron pair vacancy are suitable for use as Lewis acid. As a rule, they are selected from halogen compounds of titanium, tin, aluminum, vanadium, iron or boron. The chlorides are preferred; however, the monoalkylaluminum dichlorides and the dialkylaluminum chlorides are also suitable in the case of aluminum. The fluoride is also suitable in the case of boron. Examples of suitable Lewis acids are titanium tetrachloride, boron trichloride, boron trifluoride, tin tetrachloride, vanadium pentachloride, iron trichloride, aluminum trichloride, alkylaluminum dichlorides and dialkylaluminum chlorides. Particular preference is given to using aluminum trichloride.

Suitable β-halopropionyl halides are 3-chloropropionyl chloride and 3-bromopropionyl bromide or 3-bromopropionyl chloride. Preference is given to using 3-chloropropionyl chloride.

Preference is given to using acryloyl chloride as the acryloyl halide.

A β-halopropionyl halide is preferably used in step a) as the acylating agent.

Hydrogen chloride and hydrogen bromide are suitable hydrogen halides. Use is preferably made of a hydrogen halide in which the halogen atom corresponds to the β-halogen radical in the β-halopropionyl halide which is employed. Accordingly, hydrogen chloride is preferably used when 3-chloropropionyl chloride is employed.

All solvents which are customarily employed in Friedel-Crafts acylation reactions are suitable for use as solvents for the reaction in step a). In principle, the solvents which are suitable are aprotic solvents which do not lower the reactivity of the reagents employed, in particular of the Lewis acid, or which do not enter into any competitive reactions with the Lewis acid under the given reaction conditions. Examples of these solvents are the aromatic to be acylated itself (i.e. thiophene), aromatic hydrocarbons which are markedly more difficult to acylate than thiophene, such as benzene, nitrobenzene and halogenated aromatic hydrocarbons, e.g. chlorobenzene and dichlorobenzene, and, in addition, halogenated aliphatic hydrocarbons, in particular haloalkanes, such as chloromethane, dichloromethane, chloroform, carbon tetrachloride, chloroethane, dichloroethane and trichloroethane. Mixtures of the abovementioned solvents are also suitable. Use is preferably made of solvents, such as nitrobenzene or halogenated hydrocarbons, in which the Friedel-Crafts acylation can essentially proceed homogeneously. Preference is given, in particular, to halogenated aromatic or aliphatic hydrocarbons, with haloalkanes being particularly preferred. Use is made, especially of dichloroethane or chlorobenzene.

The Lewis acid must be used in at least equimolar quantities, based on the quantity of acylated thiophene which is theoretically to be achieved, since it forms a complex with the ketone which is formed during the acylation, with this complex being stable under the customary conditions of the Friedel-Crafts reaction. The Lewis acid is preferably used in a molar ratio of from 1:1 to 1:2, particularly preferably of from 1:1 to 1:1.5 and, in particular, of from 1:1.1 to 1:1.5, based on 1 mol of the acylation component (thiophene or β-halopropionyl halide) which is used in smaller proportion.

Thiophene and the β-haloropionyl halide are used in a molar ratio of preferably from 1:0.5 to 1:2, particularly preferably of from 1:0.7 to 1:1.5 and, in particular, of from 1:0.8 to 1:1.2.

The sequence in which the reagents are added together in connection with the Friedel-Crafts acylation is of secondary importance. Thus, it is possible, for example, to initially introduce the Lewis acid into the solvent and firstly add the β-halopropionyl halide and then the thiophene. Alternatively, it is possible to initially introduce thiophene and Lewis acid and to add the β-halopropionyl halide to them.

As a rule, it is advantageous to cool when adding the β-halopropionyl halide since the reaction of the Lewis acid with the acid halide is usually strongly exothermic. The reaction temperature is selected, inter alia, in dependence on the solvent. It is usually in the range from 10° C. to 40° C. When halohydrocarbons, in particular haloalkanes are used, the reaction temperature is suitably at most 50° C. since, otherwise, the solvent itself reacts. The reaction temperature is preferably from −20° C. to 40° C., particularly preferably from 0 to 30° C.

In principle, the reaction pressure is not critical. In general, the reaction is carried out under normal pressure; however, it can also be carried out under positive pressure or under negative pressure. Positive pressure is used, for example, when the solvent is highly volatile or not liquid under normal conditions, as is the case, for example, with chloromethane.

The hydrogen halide is preferably passed in after the acylation has taken place. Customary methods of the prior art, for example gas chromatography, thin layer chromatography or NMR spectroscopy, can be used to establish the completion of the acylation reaction. The period over which the passing in takes place depends, inter alia, on the batch size and can be determined by the skilled person in each individual case. As a rule, the hydrogen halide is passed in at least until it is no longer possible to detect any 1-thien-2-ylpropenone.

For the working-up of the acylation product, the reaction mixture is as a rule initially processed hydrolytically in order to cleave the ketone-Lewis acid complex which has formed. Water or else dilute aqueous mineral acids, for example dilute hydrochloric acid, are used for the hydrolysis. The further purification and isolation is effected using known methods, as are described, for example, in Organikum [Practical course in organic chemistry], VEB Deutscher Verlag der Wissenschaften, 17th edition, 1988, pp. 323 et seq.

The process according to the invention gives rise, in step a), to a 3-halo-(thien-2-yl)-1-propanone III in high yields. Any 1-thien-2-ylpropenone II which may be formed during the course of the acylation reaction is essentially completely converted into 3-halo-(thien-2-yl)-1-propanone III such that the reaction mixture contains at most 1 mol %, particularly preferably at most 0.5 mol %, of propenone II, based on the yield of 3-halo-(thien-2-yl)-1-propanone III.

The reduction of the propanone III in step b) is achieved, for example, by using a metal hydride or semimetal hydride or using hydrogen in the presence of a suitable transition metal catalyst.

Suitable metal hydrides or semimetal hydrides are both the neutral and the complex hydrides of metals and semimetals, respectively. Use is advantageously made of metal hydrides or semimetal hydrides which have proved to be of value in reducing ketones to alcohols. The hydrides are preferably hydrides of boron or of aluminum.

Examples of suitable neutral hydrides are borane ($BH_3$; $B_2H_6$), alane ($AlH_3$), silane ($SiH_4$), monoboranes and dialkylboranes, such as bis(3-methylbut-2-yl)borane (disiamylborane) or 9-borabicyclo[3.3.1]nonane (9-BBN), monoalkylaluminum and dialkylaluminum compounds, such as diisobutylaluminum hydride (DIBAL-H), and trialkylsilanes, such as trimethylsilane or triethylsilane.

Examples of suitable complex hydrides are complex borohydrides, such as sodium borohydride ($NaBH_4$), lithium borohydride ($LiBH_4$) or calcium borohydride $Ca[BH_4]_2$, complex aluminum hydrides, such as lithium aluminum hydride ($LiAlH_4$), complex alkylborohydrides or alkoxyborohydrides, such as lithium triethylborohydride or potassium triisopropoxyborohydride ($KB[OCH(CH_3)_2]_3H$), or complex alkylaluminum hydrides or alkoxyaluminum hydrides, such as sodium diethylaluminum hydride, lithium bis(2-methoxyethoxy)aluminum hydride ($LiAl[OC_2H_4OCH_3]_2H_2$), sodium bis(2-methoxyethoxy)aluminum hydride ($NaAl[OC_2H_4OCH_3]_2H_2$; "red Al") or lithium aluminum tris(tert-butoxy)hydride ($LiAl[OC(CH_3)_3]_3H$), and the like.

Solvents which are suitable for the reduction with metal hydrides or semimetal hydrides depend, in particular, on the reducing agent employed and should naturally not contain any groups which are also reduced under the reaction conditions. Thus, the reduction with the abovementioned hydrides is preferably carried out in aprotic solvents which do not possess any functional groups which can be reduced under the given reaction conditions. Examples of these solvents are aromatic and aliphatic hydrocarbons, for example $C_5$-$C_8$-alkanes and $C_5$-$C_8$-cycloalkanes, such as pentane, hexane, heptane, cyclopentane, cyclohexane and cyclooctane, aromatics, such as benzene, toluene, nitrobenzene, chlorobenzene and dichlorobenzene, and, in addition, open-chain and cyclic ethers having from 4 to 8 carbon atoms, such as diethyl ether, methyl tert-butyl ether, tetrahydrofuran or dioxane, and also chlorinated hydrocarbons, in particular haloalkanes, such as chloromethane, dichloromethane, chloroform, carbon tetrachloride, dichloroethane or trichloroethane. Mixtures of the abovementioned solvents are also suitable. Preference is given to using the abovementioned aromatic hydrocarbons, ethers or halohydrocarbons.

Reduction with some of the abovementioned complex hydrides, in particular with less reactive hydrides, such as sodium borohydride, can also be effected in the presence of protic solvents, e.g. of $C_1$-$C_3$-alcohols, such as methanol, ethanol, propanol or isopropanol, or even in aqueous solution. In this case, use is preferably made of a mixture composed of at least one of the previously mentioned aprotic solvents and at least one alcohol. Since the hydrides are more stable in basic protic solutions, the reaction is preferably carried out in the presence of a suitable base when protic solvents are used.

Examples of suitable bases are alkali metal hydroxides, such as sodium hydroxide or potassium hydroxide, or alkali metal carbonates, such as sodium carbonate or potassium carbonate. Sodium hydroxide is preferably used.

When many of the previously mentioned metal hydrides or semimetal hydrides are used, the reduction frequently proceeds exothermically such that the reaction is suitably carried out while removing the reaction heat, i.e. while cooling. The reaction temperature is preferably from −50 to 40° C., particularly preferably from −30 to 30° C. and, in particular, from −20 to 20° C. The reduction can be carried out using customary methods of the prior art as are described, for example, in Organikum [Practical course in organic chemistry], VEB Deutscher Verlag der Wissenschaften, 17th edition, 1988, pp. 492 et seq. In these methods, the propanone III is as a rule introduced initially and the reducing agent is added in portions. However, it is also possible to add propanone III and reducing agent in portions simultaneously.

The propanone III can also be reduced, for example, using an aluminum alkoxide. The reduction of ketones with an aluminum alkoxide is also customarily termed Meerwein-Ponndorf-Verley reduction. In this reduction, a ketone is converted into the corresponding alcohol and the alkoxide is simultaneously oxidized to the corresponding aldehyde (in the case of alkoxides formed from primary alcohols) or ketone (in the case of alkoxides formed from secondary alcohols). The reaction can be carried out using known methods as are described, for example, in Organikum [Practical course in organic chemistry], VEB Deutscher Verlag der Wissenschaften, 17th edition, 1988, pp. 486 et seq.

In addition, the propanone III can also be reduced by means of catalytic hydrogenation, i.e. by means of reacting the propanone III with hydrogen in the presence of suitable transition metal catalysts. The suitable transition metals include the metals of the subgroups VIII, VI and I, in particular platinum, ruthenium, copper, chromium and nickel. The catalysts have naturally to be selected such that they do not catalyze the hydrogenation of the thiophene group. The catalysts can be used either as heterogeneous catalysts or as homogeneous catalysts. Suitable methods are known in principle and are described, for example, in Transition Metals in Organic Synthesis. M. Beller, C. Bolm, Wiley-VCH, Weinheim, 1998, volume 2, pp. 1 et seq. (homogeneous catalysts) or p. 81 et seq. (heterogeneous catalysts).

The reduction in step b) is preferably effected using a metal hydride or semimetal hydride and particularly preferably using one of the abovementioned complex metal hyrides or semimetal hydrides. Sodium borohydride is used, in particular.

When the above-described nonasymmetric reducing agents are used, the prochiral 3-halo-1-(thien-2-yl)propan-1-one III is principally reduced to the racemic alcohol IV. The subsequent reaction with methylamine correspondingly leads to the racemic 3-methylamino-1-(thien-2-yl)propan-1-ol I.

In a preferred embodiment, the process according to the invention is used to prepare (S)-3-methylamino-1-(thien-2-yl)propan-1-ol of the formula I-S

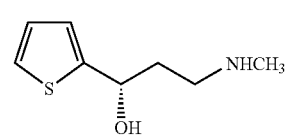

(I-S)

or to prepare this compound together with its R enantiomer I-R, in a mixture in which the enantiomer I-S predominates, with the reduction in step b) being carried out in the presence of a chiral reducing agent or a chiral catalyst which exhibit selectivity with regard to the formation of (S)-3-methylamino-1-(thien-2-yl)propan-1-ol I-S.

When this is done, the prochiral halopropanone III is reduced enantioselectively, in step b), to the S-halopropanol of the formula IV-S

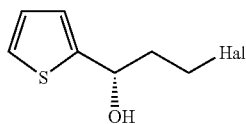

(IV-S)

or to a mixture of S and R enantiomer in which the S enantiomer predominates. For this purpose, an asymmetric metal hydride or semimetal hydride is, for example, used as the reducing agent in step b), or else the reduction is carried out in the presence of a compound which mediates asymmetric induction.

The asymmetric metal hydrides or semimetal hydrides are preferably asymmetric aluminum hydrides, boron hydrides or silicon hydrides. Suitable asymmetric borohydrides are described, for example, in E. J. Corey, C. J. Helal, Angew. Chem. 1998, 110, 2092-2118 or in M. M. Midland, L. A. Morell, Methoden Org. Chem. [Methods of organic chemistry], Houben-Weyl, 4th edtn., volume E 21d, pp. 4082-4098, 1995 which are hereby incorporated by reference in their entirety. Suitable asymmetric silicon hydrides are described, inter alia, in H. Brunner, Methoden Org. Chem. [Methods of organic chemistry], Houben-Weyl, 4th edtn., volume E21d, pp. 4074-4081,1995, which is likewise hereby incorporated by reference in its entirety.

Within the context of the present invention, compounds which mediate asymmetric induction are understood as being those compounds which, by influencing the actual reducing agent, e.g. by means of forming a bond or forming a complex with the reducing agent, or by taking up a hydrogen atom or another reductive constituent from the reducing agent, make the reduction of the propanone III enantioselective. As a rule, the compounds which mediate asymmetric induction are not themselves reducing.

These compounds include, on the one hand, asymmetric hydrogenation catalysts. In asymmetric hydrogenation, hydrogen serves as the actual reducing agent while the asymmetric catalyst favors the enantioselective formation of one of the possible enantiomers. The hydrogenation can take place either in heterogeneous phase or in homogeneous phase. Suitable catalysts for asymmetric hydrogenation in heterogeneous phase are, for example, in A. Baiker, H. U. Blaser in Handbook of Heterogeneous Catalysis, volume 5 (editors G. Ertl, H. Knörzinger and J. Weitkamp), Wiley-VCH, Weinheim, 1997, 2422-2436, which is hereby incorporated in its entirety by reference.

However, catalysts for hydrogenation in homogeneous phase are of greater importance. Catalysts which comprise a subgroup VIII metal, e.g. platinum or ruthenium, in particular ruthenium, and at least one phosphorus-containing ligand are particularly suitable. Suitable catalysts are described, for example, in R. Noyori, T. Ohkuma, Angew. Chem. 2001, 113, 40-75, which is hereby incorporated in its entirety by reference. Ruthenium(II) diamine complexes in which the ruthenium is additionally bonded to a bidentate chiral diphosphane ligand are particularly suitable. Examples of diphosphane ligands which are suitable for reducing the halopropanone III to the S-halopropanol IV-S are (R)-BINAP of the formula A, (R,R)-DIOP of the formula B and (R,R)-CHIRAPHOS of the formula C

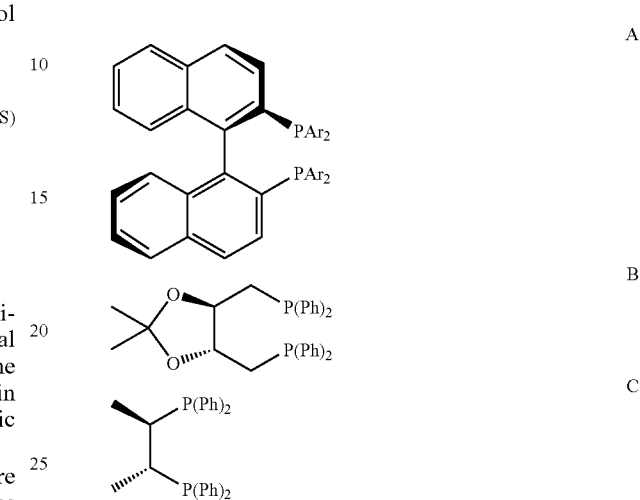

Ar=phenyl (BINAP) Ph=phenyl
4-methylphenyl (TolBINAP)
3,5-dimethylphenyl (XylBINAP)

In addition, particularly preferred catalysts contain a diamine ligand. Examples of suitable diamine ligands are 1,2-ethylenediamine, 1,2-diphenyl-1,2-ethylenediamine and 1,2-cyclohexanediamine in their enantiomeric forms.

The hydrogenation is as a rule carried out under the previously described conditions.

The oxazaborylidine of the formula D is a particularly preferred asymmetric induction-mediating compound

(D)

in which R is $C_1$-$C_4$-alkyl, such as methyl, ethyl, propyl, isopropyl, n-butyl, sec-butyl, isobutyl or tert-butyl and, in particular, methyl.

This reagent can be used to convert prochiral ketones into secondary alcohols with a high degree of enantioselectivity (E. J. Corey, Pure Appl. Chem. 62, 1209, 1990; E. J. Corey, J. O. Link, J. Am. Chem. Soc. 114, 1906, 1992). Boranes, e.g. $BH_3$, dialkylboranes, dialkoxyboranes or diaryloxyboranes are used as the actual reducing agent. The reaction of the chloropropanone III.1 with the oxazaborylidine D (R=methyl) and $BH_3$ to give the S-chloropropanol IV.1-S has already been described by W. J. Wheeler and F. Kuo in Journal of Labelled Compounds and Radiopharmaceuticals, volume XXXVI, No. 3, pp. 213-223.

In the reduction, the oxazaborylidene is as a rule used in catalytic quantities. While the borane is used in at least equimolar quantities, based on the halopropanone III, it is preferably used in excess. The reaction is usually carried out in suitable solvents. Suitable solvents are aprotic solvents which do not possess any groups which can be reduced under the given reaction conditions. These solvents include, in particular, the previously mentioned haloalkanes, aromatics and cyclic or acyclic ethers. Preference is given to using ethers, with tetrahydrofuran being particularly preferred. The reaction temperature is preferably from −80 to 20° C., particularly preferably from −30 to 10° C. The reaction is as a rule carried out such that the oxazaborylidine is initially introduced into the solvent and either first the borane and then the halopropanone III or, conversely, first the halopropanone III and then the borane, are added, at the desired reaction temperature, with the first addition procedure being preferred. The duration of the reaction depends, inter alia, on the batch size and can be determined by the skilled person in each individual case.

It has been found, surprisingly, that the enantioselective reduction of the propanone III to the S-halopropanol IV-S works well when catalyzed by an enzyme, in particular when a dehydrogenase is present. A dehydrogenase is therefore used as the reducing agent in another preferred embodiment of the process according to the invention.

After the reduction in the process according to the invention has been completed, and depending on the reducing method which has been used, the catalyst or excess reducing agent employed is, where appropriate, inactivated or removed. When metal hydrides or semimetal hydrides are used, this is as a rule effected by means of hydrolysis, for example using an aqueous or alcoholic solution. Hydrolytic working-up is also frequently employed when using homogeneous hydrogenation catalysts or when reducing with aluminum alkoxides. If the reduction is carried out in the form of a catalytic hydrogenation in heterogeneous phase, or using an enzyme as the reducing agent, the catalyst or the enzyme can be removed by physical separation, e.g. by means of decanting or filtering. However, preference is given to not inactivating initially when homogeneous reduction systems are used, in particular when reduction takes place using metal hydrides or semimetal hydrides.

It has proved to be advantageous for the haloporopanol IV which is obtained after the reduction not to be isolated but, instead, to be reacted directly with methylamine to give the 3-methylamino-1-(thien-2-yl)propan-1-ol I. To do this, the reaction mixture, which may, where appropriate, have been inactivated, or which has been separated from heterogeneous reduction systems, is treated with methylamine and reacted, preferably at an elevated temperature, for example at from 30 to 80° C., in particular at from 50 to 70° C. The methylamine can be used either in gas form or as an aqueous solution, with its use as an aqueous solution being preferred. It is preferably used in a quantity of from 1 to 100 molar equivalents, particularly preferably of from 5 to 10 molar equivalents, based on the quantity of the halopropanone III employed. The reaction is preferably effected under a pressure of from 1 to 250 bar and, in particular under the intrinsic pressure which the system itself generates.

After the reaction with methylamine has been completed, the reaction mixture is worked up in a customary manner. For this, the catalyst or the reducing agent is inactivated and separated off as already described, if this was not already done before the methylamine was added, after which the solvent is removed and pure methylaminopropanol I is isolated from the residue, for example by means of crystallization, digestion, extraction or chromatography.

It is possible to use the process according to the invention to obtain 3-methylamino-1-(thien-2-yl)propan-1-ol I in good yields. In particular, no reagents or solvents which are expensive or elaborate to handle are required in step a) of the process and the halopropanone III is formed in very high yield. In step b), the isolation of the labile halopropanol IV, and a loss of yield and/or the difficult handling of the halopropanol IV associated therewith, are avoided. In addition, the process according to the invention can be used to selectively obtain the S enantiomer of the methylaminopropanol I-S, which is essential for the further conversion into duloxetine, if the reduction in step b) is carried out using a chiral reducing agent.

In addition, the present invention also relates to a process for preparing (S)-3-methylamino-1-(thien-2-yl)propan-1-ol of the formula I-S, in which a 3-halo-1-(thien-2-yl)propan-1-one III is reduced enantioselectively, which comprises carrying out the reduction in the presence of a dehydrogenase. In a preferred embodiment of the process, the (S)-3-halo-1-(thien-2-yl)propan-1-ol IV-S which is obtained in this connection is reacted with methylamine without being isolated. The reader is expressly referred to the following observations as regards suitable and preferred dehydrogenases and as regards implementing the process.

Biochemical Embodiments:

Suitable dehydrogenases (EC 1.1.X.X) are, in particular, dehydrogenases (E.C. 1.1.1.x), in particular alcohol dehydrogenases (E.C.1.1.1.1 or E.C.1.1.1.2), which bring about the selective reduction of the halopropanone III to the S-halopropanol IV-S. The dehydrogenase is preferably obtained from a microorganism, particularly preferably from a bacterium or a fungus, in particular a yeast, which is in each case deposited in strain collections or obtainable from natural source isolates such as soil samples, biomass samples and the like. The dehydrogenase is in particular derived from a yeast or a lactic acid bacterium.

The dehydrogenase can be used in purified or partially purified form or in the form of the microorganism itself. Methods for isolating and purifying dehydrogenases from microorganisms are sufficiently well known to the skilled person, for example from K. Nakamura & T. Matsuda, "Reduction of Ketones" in K. Drauz and H. Waldmann, Enzyme Catalysis in Organic Synthesis 2002, Vol. III, 991-1032, Wiley-VCH, Weinheim. Recombinant methods for producing dehydrogenases are likewise known, for example from W. Hummel, K. Abokitse, K. Drauz, C. Rollmann and H. Gröger, Adv. Synth. Catal. 2003, 345, Nos. 1+2, pp. 153-159.

Examples of suitable bacteria are those of the genus *Pseudomonas, Burkholderia, Agrobacterium, Rhodococcus, Lactobaccillus* or *Lactococcus*. Examples of suitable yeasts are those of the genus *Geotrichum, Pichia, Candida, Hansenula* or *Saccharomyces*.

Particular preference is given to using dehydrogenases which are derived from yeasts and lactic acid bacteria. Of these dehydrogenases, those which are preferred are dehydrogenases which are obtained from yeasts of the genus *Geotrichum* or *Candida* or those which are obtained from lactic acid bacteria of the genus *Lactobaccillus* or *Lactococcus*.

Examples of *Lactobaccillus* species are *L. brevis, L. kefir, L. plantarum, L. casei, L. acidophilus, L. delbrueckii* and *L. sanfrancisco*.

Examples of *Candida* species are *C. magnoliae, C. rugosa, C. utilis, C. boidinii, C. parapsilosis* and *C. antarctica*.

Examples of *Geotrichum* species are *G. candidum, G. clavatum* and *G. fermentans*.

Particular preference is given to using dehydrogenases derived from *Candida magnoliae, Geotrichum candidum* or *Lactobaccillus brevis.*

The reduction with the dehydrogenase is usually carried out in the presence of a suitable coenzyme (also termed cofactor). NADH and/or NADPH is usually employed as the coenzyme for reducing the ketone. In addition, it is possible to use dehydrogenases as cellular systems which inherently contain cofactor or to which alternative redox mediators are added (A. Schmidt, F. Hollmann and B. Bühler "Oxidation of Alcohols" in K. Drauz and H. Waldmann, Enzyme Catalysis in Organic Synthesis 2002, Vol. III, 991-1032, Wiley-VCH, Weinheim).

The reduction with the dehydrogenase is also usually carried out in the presence of a suitable cosubstrate which as a rule acts as reducing agent for the coenzyme which is oxidized during the course of the reduction and consequently regenerates this coenzyme. Examples of suitable cosubstrates are sugars, in particular hexoses, such as glucose, mannose or fructose, and/or oxidizable alcohols, in particular ethanol, propanol or isopropanol, and also formate. A second dehydrogenase, such as glucose dehydrogenase when glucose is being used as a cosubstrate, can be added for the purpose of oxidizing the cosubstrate and, in association with this, for regenerating the coenzyme. This dehydrogenase can be employed as a free or immobilized enzyme or in the form of free or immobilized cells. It can be prepared either separately or by means of coexpression in a (recombinant) dehydrogenase strain.

The dehydrogenases which are used in accordance with the invention can be employed in free or immobilized form. An immobilized enzyme is understood as meaning an enzyme which is fixed to an inert support. Suitable support materials, and the enzymes which are immobilized on them, are known from EP-A-1149849, EP-A-1 069 183 and DE-OS 100193773, and also from the literature references which are cited therein. In this regard, the disclosure in these documents is hereby incorporated, in its entirety, by reference. The suitable support materials include, for example, clays, clay minerals, such as kaolinite, diatomaceous earth, pearlite, silicon dioxide, aluminum oxide, sodium carbonate, calcium carbonate, cellulose powders, anion exchange materials, synthetic polymers, such as polystyrene, acrylic resins, phenolformaldehyde resins, polurethanes and polyolefins, such as polyethylene and polypropylene. The support materials are used for preparing the supported enzymes, usually in a finely divided, particulate form, with porous forms being preferred. The particle size of the support material is usually not more than 5 mm, in particular not more than 2 mm (grading curve). In an analogous manner, it is possible to select a free or immobilized form when using the dehydrogenase as whole-cell catalyst. Examples of support materials are Ca alginate and carrageenan. Enzymes as well as cells can also be crosslinked directly with glutaraldehyde (crosslinking to give CLEAs).

Corresponding, and additional immobilization methods are described, for example, in J. Lalonde and A. Margolin "Immobilization of Enzymes" in K. Drauz and H. Waldmann, Enzyme Catalysis in Organic Synthesis 2002, Vol. III, 991-1032, Wiley-VCH, Weinheim.

The reduction can be carried out in aqueous or nonaqueous reaction media or in 2-phase systems or (micro)emulsions. The aqueous reaction media are preferably buffered solutions which as a rule are at a pH of from 5 to 8, preferably of from 6 to 8. Apart from water, the aqueous solvent can additionally contain at least one alcohol, e.g. ethanol or isopropanol.

"Nonaqueous reaction media" are to be understood as meaning reaction media which contain less than 1% by weight, preferably less than 0.5% by weight, of water, based on the total weight of the reaction medium. The reaction is preferably carried out in an organic solvent. Examples of suitable solvents are aliphatic hydrocarbons, preferably having from 5 to 8 carbon atoms, such as pentane, cyclopentane, hexane, cyclohexane, heptane, octane or cyclooctane, halogenated aliphatic hydrocarbons, preferably having one or two carbon atoms, such as dichlormethane, chloroform, carbon tetrachloride, dichloroethane or tetrachlorethane, aromatic hydrocarbons, such as benzene, toluene, the xylenes, chlorobenzene or dichlorobenzene, aliphatic acyclic and cyclic ethers, preferably having from 4 to 8 carbon atoms, such as diethyl ether, methyl tert-butyl ether, ethyl tert-butyl ether, dipropyl ether, diisopropyl ether, dibutyl ether or tetrahydrofuran, or esters, such as ethyl acetate or n-butyl acetate, or ketones, such as methyl isobutyl ketone or dioxane, or mixtures thereof. Particular preference is given to using the abovementioned ethers, in particular tetrahydrofuran.

For example, the reduction with the dehydrogenase is carried out in an aqueous-organic, in particular aqueous reaction medium.

The halopropanone III is preferably employed, in the enzymic reduction, at a concentration of from 0.1 g/l to 500 g/l, particularly preferably of from 1 g/l to 50 g/l, and can be subsequently supplied continuously or discontinuously.

As a rule, the enzymic reduction is carried out at a reaction temperature which is below the temperature at which the dehydrogenase employed is inactivated and is preferably at least −10° C. It is particularly preferably in the range from 0 to 100° C., in particular of from 15 to 60° C. and, especially of from 20 to 40° C., e.g. at about 30° C.

In order to implement the reaction, it is possible, for example, to initially introduce the halopropanone III together with the dehydrogenase, the solvent and, where appropriate, the coenzymes, where appropriate an auxiliary dehydrogenase for regenerating the coenzyme, and/or other cosubstrates, and to blend the mixture, e.g. by mean of stirring or shaking. However, it is also possible to immobilize the dehydrogenase(s) in a reactor, for example in a column, and to pass a mixture containing the halopropanone III and, where, appropriate, coenzymes and/or cosubstrates through the reactor. For this purpose, it is possible to pass the mixture through the reactor in a cyclic process until the desired conversion has been achieved. In this connection, the keto group of the halopropanone III is reduced to an OH group in connection with which the S enantiomer of the haloropanol IV-S is formed essentially selectively. As a rule, the reduction will be conducted up to a conversion of at least 70%, particularly preferably of at least 85% and, in particular, of at least 95%, based on the halopropanone III which is present in the mixture. In this connection, the progress of the reaction, i.e. the sequential reduction of the ketone, can be monitored by means of customary methods, such as gas chromatography.

The dehydrogenases which are particularly preferably used in the process according to the invention are alcohol dehydrogenases which possess at least one of the following properties:

Alcohol dehydrogenases having an amino acid sequence which, in the region of the N terminus a) comprises a constituent amino acid sequence of at least 5, 6, 7 or 8, preferably at least 10, such as 10, 11, 12, 13, 14 or 15, consecutive amino acid residues as depicted in SEQ ID NO: 1, with the position corresponding to amino acid position 12 as depicted in SEQ ID NO:1 preferably additionally standing for valine; or b) comprises a constituent amino acid sequence of at least 5, 6, 7 or 8, preferably at least 10, such as 10,11, 12, 13, 14 or 15, consecutive amino acid residues as depicted in SEQ ID NO: 2; and functional equivalents thereof.

Alcohol dehydrogenases which are capable of reducing 3-chloro-1-(thien-2-yl)propan-1-one to (S)-3-chloro-1-(thien-2-yl)propan-1-ol.

Alcohol dehydrogenases which catalyze the reduction (in the presence of NADH and/or NADPH; at 30° C. and pH 6.0) in an enantiomeric purity of at least 85% ee.

Alcohol dehydrogenases which are encoded by a nucleic acid sequence comprising SEQ ID NO:3 or which comprise an amino acid sequence as depicted in SEQ ID NO: 4 or at least a constituent sequence as depicted in FIG. 3, and can preferably be obtained from *Lactobaccillus brevis*; and also the functionally equivalent alcohol dehydrogenases which are derived therefrom.

Alcohol dehydrogenases which are encoded by a nucleic acid sequence comprising SEQ ID NO: 5 or which possess an amino acid sequence comprising SEQ ID NO: 6 and can preferably be obtained from *Candida magnoliae* (ATCC 12573); and also the functionally equivalent alcohol dehydrogenases which are derived therefrom.

The present invention also relates to an (S)-3-chloro-1-(thien-2-yl)-propan-1-ol dehydrogenase which possesses at least one of the above-listed properties.

The temperature range in which the dehydrogenase is stable is preferably from 10 to 80° C. The temperature at which its activity is optimal is preferably in the range of from 20 to 60° C., particularly preferably of from 25 to 40° C. The pH range in which it is stable is preferably from pH 4 to 10. The optimum pH for the dehydrogenation is preferably in the range of from pH 5 to 8.

In addition, the dehydrogenase according to the invention is preferably capable of dehydrogenating (S)-3-chloro-1-(thien-2-yl)propan-1-ol to give 3-chloro-1-(thien-2-yl)propan-1-one in the presence of $NAD^+$ or $NADP^+$. It preferably has a molecular weight in the region of 30±2 kdaltons.

The present invention also relates to a nucleic acid sequence which comprises the coding sequence for the dehydrogenase according to the invention or a constituent coding sequence. A nonlimiting example of this is the sequence depicted in SEQ ID NO: 3 or SEQ ID NO: 6.

The present invention furthermore relates to an expression cassette which comprises the nucleic acid sequence according to the invention in operative linkage with at least one regulatory nucleic acid sequence.

The present invention furthermore relates to a recombinant vector which comprises at least one expression cassette according to the invention.

In addition, the present invention relates to a prokaryotic or eukaryotic host which is transformed with at least one vector according to the invention.

Finally, the present invention relates to the use of the dehydrogenase according to the invention, or of a microorganism which produces this dehydrogenase, for preparing (S)-3-halo-1-(thien-2-yl)propan-1-ol and, in particular for preparing duloxetine.

Further Modifications of Dehydrogenase According to the Invention

The invention also includes "functional equivalents" of the specifically disclosed enzymes which possess (S)-3-chloro-1-(thien-2-yl)propan-1-ol dehydrogenase activity as well as the use of these equivalents in the processes according to the invention.

Within the context of the present invention, "functional equivalents" or analogs of the specifically disclosed enzymes are polypeptides which differ from these enzymes but which still possess the desired biological activity, such as substrate specificity. Thus, "functional equivalents" are understood, for example, as meaning enzymes which reduce 3-chloro-1-(thien-2-yl)propan-1-one to the corresponding S alcohol and which possess at least 20%, preferably 50%, particularly preferably 75%, very particularly preferably 90%, of the activity of an enzyme which comprises one of the amino acid sequences listed under SEQ ID NO: 1, 2, 4 or 6 or depicted in FIG. 3. Functional equivalents are also preferably stable beween pH 4 and 10 and advantageously possess a pH optimum between 5 and 8 as well as a temperature optimum in the range from 20° C. to 80° C.

According to the invention, "functional equivalents" are also understood as meaning, in particular, mutants which possess an amino acid other than the specifically mentioned amino acid in at least one sequence position in the abovementioned amino acid sequences but nevertheless possess one of the abovementioned biological activities. "Functional equivalents" consequently comprise the mutants which can be obtained by means of one or more amino acid additions, amino acid replacements, amino acid deletions and/or amino acid inversions, with said changes being able to appear in any sequence position as long as they lead to a mutant which possesses the property profile according to the invention. Functional equivalence also exists, in particular, when the reactivity patterns of the mutant and the unaltered polypeptide agree qualitatively, i.e. the same substrates are, for example, converted at different rates.

Examples of suitable amino acid replacements are listed in the following table:

| Original residue | Examples of the replacement |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the described polypeptides as well as "functional derivatives" and "salts" of the polypeptides.

In this connection "precursors" are natural or synthetic precursors of the polypeptides, which precursors do or do not possess the desired biological activity.

The expression "salts" is understood as meaning both salts of carboxyl groups and acid addition salts of amino groups of the protein molecules according to the invention. Salts of carboxyl groups can be prepared in a manner known per se and comprise inorganic salts, such as sodium, calcium, ammonium, iron and zinc salts, as well as salts with organic bases, for example amines, such as triethanolamine, arginine, lysine, piperidine and the like. Acid addition salts, for example salts with mineral acids, such as hydrochloric acid or sulfuric acid, and salts with organic acids, such as acetic acid and oxalic acid, likewise form part of the invention.

"Functional derivatives" of polypeptides according to the invention can likewise be prepared, using known techniques, at functional amino acid side groups or at their N-terminal or C-terminal ends. These derivatives comprise, for example, aliphatic esters of carboxylic acid groups; amides of carboxylic acid groups, which amides can be obtained by reacting with ammonia or with a primary or secondary amine; N-acyl derivatives of free amino groups, which derivatives are prepared by reacting with acyl groups; or O-acyl derivatives of free hydroxyl groups, which derivatives are prepared by reacting with acyl groups.

In the case of a possible protein glycosylation, "functional equivalents" according to the invention include proteins of the above-described type in deglycosylated or glycosylated form as well as modified forms which can be obtained by altering the glycosylation pattern.

"Functional equivalents" naturally also include polypeptides which are available from other organisms as well as naturally occurring variants. For example, areas of homologous sequence regions can be established by means of sequence comparisons and equivalent enzymes can be identified using the specific guidelines of the invention.

"Functional equivalents" also include fragments, preferably individual domains or sequence motifs, of the polypeptides according to the invention, which fragments possess, for example, the desired biological function.

In addition, "functional equivalents" are fusion proteins which contain one of the abovementioned polypeptide sequences, or functional equivalents derived therefrom, and at least one further heterologous sequence, which is functionally different therefrom and is functionally linked N-terminally or C-terminally (i.e. without any significant reciprocal functional impairment of the fusion protein moieities). Non-limiting examples of such heterologous sequences are signal peptides or enzymes.

"Functional equivalents" which are also included in the invention are homologs of the specifically disclosed proteins. These homologs possess at least 60%, preferably at least 75%, in particular at least 85%, such as 90%, 95%, 97% or 99%, homology with one of the specifically disclosed amino acid sequences, as calculated using the Pearson and Lipman algorithm, Proc. Natl. Acad, Sci. (USA) 85(8), 1988, 2444-2448. The percentage homology of a homologous polypeptide according to the invention means, in particular, the percentage identity of the amino acid residues based on the entire length of one of the amino acid sequences which is specifically described herein.

Homologs of the proteins or polypeptides according to the invention can be produced by means of mutagenesis, e.g. by means of point mutation or truncation of the protein.

Homologs of the proteins according to the invention can be identified by means of screening combinatorial libraries of mutants, such as truncation mutants. For example, a variegated library of protein variants can be produced by means of combinatorial mutagenesis at the nucleic acid level, for example by enzymatically ligating a mixture of synthetic oligonucleotides. There are a large number of methods which can be used for preparing libraries of potential homologs from a degenerate oligonucleotide sequence. A degenerate gene sequence can be synthesized chemically in an automatic DNA synthesizing machine and the synthetic gene can be ligated into a suitable expression vector. Using a degenerate gene set makes it possible to prepare all the sequences in a mixture which encode the desired set of potential protein sequences. Methods for synthesizing degenerate oligonucleotides are known to the skilled person (e.g. Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

Several techniques for screening combinatorial library gene products which have been prepared by point mutations or truncation, and for screening cDNA libraries for gene products possessing a selected property, are known in the prior art. These techniques can be adapted for rapidly screening the gene libraries which have been generated by combinatorial mutagenesis of homologs according to the invention. The most frequently employed techniques for screening large gene libraries which are subject to a high-throughput analysis comprise cloning the gene library into replicable expression vectors, transforming the suitable cells with the resulting vector library and expressing the combinatorial genes under conditions under which detection of the desired activity facilitates the isolation of the vector which encodes the gene whose product was detected. Recursive ensemble mutagenesis (REM), a technique which augments the frequency of functional mutants in the libraries, can be used in combination with the screening tests in order to identify homologs (Arkin and Yourvan (1992) PNAS 89:7811-7815; Delgrave et al. (1993) Protein Engineering 6(3):327-331).

Further Embodiment of Coding Nucleic Acid Sequences According to the Invention

The invention relates, in particular, to nucleic acid sequences (single-stranded and double-stranded DNA and RNA sequences, such as cDNA and mRNA) which encode an enzyme which possesses dehydrogenase activity according to the invention. Preference is given to nucleic acid sequences which, for example, encode amino acid sequences as depicted in SEQ ID NO: 1, 2, 4, 6 or FIG. 3, or characteristic constituent sequences thereof, or which comprise nucleic acid sequences as depicted in SEQ ID NO: 3 or 5, or characteristic constituent sequences thereof.

All of the nucleic acid sequences which are mentioned herein can be prepared, in a manner known per se, by means of chemical synthesis from the nucleotide building blocks, as, for example, by means of fragment condensation of individual overlapping complementary nucleic acid building blocks of the double helix. Oligonucleotides can, for example, be synthesized chemically, in a known manner, using the phosphoamidite method (Voet, Voet, 2nd edition, Wiley Press New York, pages 896-897). The attachment of synthetic oligonucleotides and the filling-in of gaps using the DNA polymerase Klenow fragment and ligation reactions, and also general cloning methods, are described in Sambrook et al. (1989), Molecular Cloning: A laboratory manual, Cold Spring Harbor Laboratory Press.

The invention also relates to nucleic acid sequences (single-stranded and double-stranded DNA and RNA sequences, such as cDNA and mRNA) which encode one of the above polypeptides and their functional equivalents which are accessible, for example, using artificial nucleotide analogs.

The invention relates both to isolated nucleic acid molecules which encode polypeptides or proteins according to the invention or biologically active segments thereof and to nucleic acid fragments which can be used, for example, as hybridization probes or primers for identifying or amplifying coding nucleic acids according to the invention.

The nucleic acid molecules according to the invention can furthermore contain untranslated sequences from the 3' end and/or the 5' end of the coding gene region.

The invention also includes the nucleic acid molecules, or a segment thereof, which are complementary to the specifically described nucleotide sequences.

The nucleotide sequences according to the invention make it possible to generate probes and primers which can be used for identifying and/or cloning homologous sequences in other cell types and organisms. These probes or primers usually comprise a nucleotide sequence region which hybridizes, under "stringent" conditions (see below), with at least about 12, preferably at least about 25, such as about 40, 50 or 75, consecutive nucleotides in a sense strand of a nucleic acid sequence according to the invention or in a corresponding antisense strand.

An "isolated" nucleic acid molecule is separated from other nucleic acid molecules which are present in the natural source of the nucleic acid and can moreover be essentially free of other cellular material or culture medium, when it is prepared by means of recombinant techniques, or free of chemical precursors or other chemicals when it is synthesized chemically.

A nucleic acid molecule according to the invention can be isolated using standard molecular biological techniques and the sequence information which is provided in accordance with the invention. For example, cDNA can be isolated from a suitable cDNA library by using one of the specifically disclosed complete sequences, or a segment thereof, as the hybridization probe and employing standard hybridization techniques (as described, for example, in Sambrook, J., Fritsch, E. F. and Maniatis, T. Molecular Cloning: A Laboratory Manual. $2^{nd}$ edtn., Cold Spring Harbor Laboratory, Cold Spring Harbor Laboratory Press, Cold Spring Harbor, N.Y., 1989). Furthermore, the polymerase chain reaction can be used to isolate a nucleic acid molecule which comprises one of the disclosed sequences, or a segment thereof, with use being made of the oligonucleotide primers which have been constructed on the basis of this sequence. The nucleic acid which has been amplified in this way can be cloned into a suitable vector and characterized by means of DNA sequence analysis. The oligonucleotides according to the invention can also be prepared by means of standard methods of synthesis, e.g. using an automated DNA synthesis appliance. In principle, the nucleic acid sequences according to the invention can be identified in, and isolated from, any organisms. Advantageously, the nucleic acid sequences according to the invention, or the homologs thereof, can be isolated from fungi, yeasts or bacteria. Bacteria which may be mentioned are Gram-negative bacteria and Gram-positive bacteria. The nucleic acids according to the invention are preferably isolated from Gram-negative bacteria, advantageously from alpha-proteobacteria, beta-proteobacteria or gamma-proteobacteria, particularly preferably from bacteria of the families Enterobacteriaceae, Pseudomonadaceae, or Rhizobiaceae, very particularly preferably from bacteria of the genus *Agrobacterium, Pseudomonas* or *Burkholderia,* using methods known to the skilled person.

Nucleic acid sequences according to the invention can, for example, be isolated from other fungi or bacteria using customary hybridization methods or the PCR technique, for example by way of genomic or cDNA libraries. These DNA sequences hybridize with the sequences according to the invention under standard conditions. Use is advantageously made, for the hybridization, of short oligonucleotides from the conserved regions, for example from the active center, with it being possible to identify these oligonucleotides by comparing with a dehydrogenase according to the invention in a manner known to the skilled person. However, it is also possible to use longer fragments of the nucleic acids according to the invention, or the complete sequences, for the hybridization. These standard conditions vary depending on the nucleic acid employed (oligonucleotide, longer fragment or complete sequence) or depending on which nucleic acid type, DNA or RNA, is used for the hybridization. Thus, the melting temperatures for DNA:DNA hybrids are, for example, approx. 10° C. lower than those for DNA:RNA hybrids of the same length.

Depending on the nucleic acid, standard conditions are to be understood, for example, as being temperatures between 42 and 58° C. in an aqueous buffer solution containing a concentration of from 0.1 to 5×SSC (1×SSC=0.15 M NaCl, 15 mM sodium citrate, pH 7.2) or additionally in the presence of 50% formamide, such as 42° C. in 5×SSC, 50% formamide. Advantageously, the hybridization conditions for DNA:DNA hybrids are 0.1×SSC and temperatures from about 20° C. to 45° C., preferably from about 30° C. to 45° C. For DNA:RNA hybrids, the hybridization conditions are advantageously 0.1×SSC and temperatures from about 30° C. to 55° C., preferably from about 45° C. to 55° C. These temperatures which are specified for the hybridization are melting temperature values, which have been calculated by way of example, for a nucleic acid having a length of approx. 100 nucleotides and a G+C content of 50% in the absence of formamide. The experimental conditions for the DNA hybridization are described in specialist textbooks of genetics, such as Sambrook et al., "Molecular Cloning", Cold Spring Harbor Laboratory, 1989, and can be calculated using formulae known to the skilled person, for example in dependence on the length of the nucleic acids, the nature of the hybrids or the G+C content. The skilled person can obtain further information with regard to hybridization from the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

The invention also relates to derivatives of the nucleic acid sequences which are specifically disclosed or which can be derived.

Thus, further nucleic acid sequences according to the invention can be derived, for example, from SEQ ID NO:3 or 5 and differ therefrom by the addition, replacement, insertion or deletion of single or several nucleotides but still encode polypeptides having the desired property profile.

The invention also includes those nucleic acid sequences which comprise what are termed silent mutations or are altered, as compared with a specifically mentioned sequence, in accordance with the codon usage of a specific organism of origin or host organism, as well as naturally occurring variants, such as splice variants or allele variants, thereof.

The invention likewise relates to sequences which can be obtained by means of conservative nucleotide replacements (e.g. the amino acid in question is replaced with an amino acid of the same charge, size, polarity and/or solubility).

The invention also relates to the molecules which are derived from the specifically disclosed nucleic acids as a result of sequence polymorphisms. These genetic polymorphisms can exist between individuals within a population as a result of natural variation. These natural variations usually give rise to a variance of from 1 to 5% in the nucleotide sequence of a gene.

"Derivatives of a nucleic acid sequence according to the invention" are to be understood to mean, for example, allele variants which possess at least 40% homology on the deduced amino acid level, preferably at least 60% homology, very particularly preferably at least 80, 85, 90, 93, 95 or 98% homology, over the entire sequence region (in regard to homology at the amino acid level, the reader may be referred to the above observations regarding the polypeptides). The homologies may advantageously be higher over constituent regions of the sequences.

Furthermore, "derivatives" are also to be understood as being homologs of the nucleic acid sequences according to the invention, for example fungal or bacterial homologs, truncated sequences, or single-stranded DNA or RNA of the coding and noncoding DNA sequence. They thus possess, for example, at the DNA level a homology of at least 40%, preferably of at least 60%, particularly preferably of at least 70%, very particularly preferably of at least 80%, over the entire DNA region specified.

In addition, "derivatives" are also to be understood as being, for example, fusions with promoters. The promoters, which are located upstream of the given nucleotide sequences, can be altered by means of one or more nucleotide exchanges, insertions, inversions and/or deletions without, however, the functionality or the activity of the promoters being impaired. Furthermore, the activity of the promoters can be increased by altering their sequences or the promoters can be completely replaced with more active promoters, including those from organisms belonging to other species.

"Derivatives" are also to be understood as being variants whose nucleotide sequences have been altered in the region from −1 to −1000 bases upstream of the start codon or from 0 to 1000 bases downstream of the stop codon such that gene expression and/or protein expression is altered, preferably augmented.

The invention also furthermore comprises nucleic acid sequences which hybridize with the abovementioned coding sequences under "stringent conditions". This property is understood as being the ability of a polynucleotide or oligonucleotide to bind, under stringent conditions, to a sequence which is virtually complementary whereas, under these conditions, nonspecific bonds are not formed between non-complementary partners. For this purpose, the sequences should be 70-100%, preferably 90-100%, complementary. The characteristic of complementary sequences of being able to bind to each other specifically is utilized, for example, in the Northern blotting or Southern blotting technique or in connection with primer binding in PCR or RT-PCR. Oligonucleotides of a length of 30 base pairs and upwards are customarily used for this purpose. In the Northern blotting technique, for example, stringent conditions are understood as being the use of a washing solution, for example 0.1×SSC buffer containing 0.1% SDS (20×SSC: 3M NaCl, 0.3M Na citrate, pH 7,0), which is at a temperature of 50-70° C., preferably 60-65° C., for eluting nonspecifically hybridized cDNA probes or oligonucleotides. In this connection, as mentioned above, the only nucleic acids to remain bound to each other are those which are highly complementary. The establishment of stringent conditions is known to the skilled person and is described, for example, in Ausubel et al., Current Protocols in Molecular Biology, John Wiley & Sons, N.Y. (1989), 6.3.1-6.3.6.

These polynucleotides can be found by screening genomic or cDNA libraries and, where appropriate, amplified therefrom by means of PCR using suitable primers and then, for example, isolated using suitable probes. In addition, polynucleotides according to the invention can also be synthesized chemically.

Embodiments of Constructs According to the Invention

In addition, the invention also relates to expression constructs which contain, under the genetic control of regulatory nucleic acid sequences, a nucleic acid sequence which encodes a polypeptide according to the invention; it also relates to vectors which comprise at least one of these expression constructs.

These constructs according to the invention preferably comprise a promoter 5'-upstream of the given coding sequence and a terminator sequence 3'-downstream and also, where appropriate, further customary regulatory elements which are in each case operatively linked to the coding sequence.

An "operative linkage" is understood as being the sequential arrangement of promoter, coding sequence, terminator and, where appropriate, further regulatory elements such that each of the regulatory elements is able, as required, to fulfill its function in connection with the expression of the coding sequence. Examples of operatively linkable sequences are targeting sequences as well as enhancers, polyadenylation signals and the like. Other regulatory elements include selectable markers, amplification signals, origins of replication and the like. Suitable regulatory sequences are described, for example, in Goeddel, Gene Expression Technology: Methods in Enzymology 185, Academic Press, San Diego, Calif. (1990).

A nucleic acid construct according to the invention is to be understood, in particular, as being those in which the gene for a dehydrogenase according to the invention has been operatively or functionally linked to one or more regulatory signals for the purpose of regulating, e.g. increasing, expression of the gene.

In addition to these regulatory sequences, the natural regulation of these sequences, upstream of the actual structural genes, can still be present and, where appropriate, have been genetically altered such that the natural regulation has been switched off and the expression of the genes has been increased. However, the nucleic acid construct can also have a simpler composition, i.e. no additional regulatory signals have been inserted upstream of the coding sequence and the natural promoter, together with its regulation, has not been removed. Instead of this, the natural regulatory sequence is mutated such that there is no longer any regulation and expression of the gene is increased.

A preferred nucleic acid construct also advantageously contains one or more of the previously mentioned enhancer sequences which is/are functionally linked to the promoter and which make(s) it possible to increase the expression of the nucleic acid sequence. It is also possible to insert additional advantageous sequences, such as further regulatory elements or terminators, at the 3' end of the DNA sequences. The nucleic acids according to the invention can be present in the construct in one or more copies. The construct can also contain additional markers, such as antibiotic resistances or auxotrophy-complementing genes, where appropriate for the purpose of selecting for the construct.

The regulatory sequences which are advantageous for the process according to the invention are present, for example, in promoters such as the cos, tac, trp, tet, trp-tet, lpp, lac, lpp-lac, lacI$^q$, T7, T5, T3, gal, trc, ara, rhaP (rhaP$_{BAD}$) SP6, lambda-P$_R$ or lambda-P$_L$ promoter, which promoters are advantageously used in Gram-negative bacteria. Other advantageous regulatory sequences are present, for example, in the Gram-positive promoters amy and SPO2 and in the yeast or fungal promoters ADC1, MFalpha, AC, P-60, CYC1, GAPDH, TEF, rp28 and ADH. The pyruvate decarboxylase and methanol oxidase promoters, for example from *Hansenula*, are also advantageous in this connection. It is also possible to use artificial promoters for the regulation.

For the purpose of expression in a host organism, the nucleic acid construct is advantageously inserted into a vector, such as a plasmid or a phage, which enables the genes to be expressed optimally in the host. In addition to plasmids and phages, the vectors are also to be understood as being any other vectors known to the skilled person, that is, for example, viruses, such as SV40, CMV, baculovirus and adenovirus, transposons, IS elements, phasmids, cosmids and linear or circular DNA. These vectors can be replicated autonomously in the host organism or replicated chromosomally. These vectors constitute a further embodiment of the invention. Examples of suitable plasmids are pLG338, pACYC184, pBR322, pUC18, pUC19, pKC30, pRep4, pHS1, pKK223-3, pDHE19.2, pHS2, pPLc236, pMBL24, pLG200, pUR290, pIN-III$^{113}$-B1, Igt11 and pBdCl, in *E. coli,* pIJ101, pIJ364, pIJ702 and pIJ361, in *Streptomyces,* pUB110, pC194 and pBD214, in *Bacillus,* pSA77 and pAJ667, in *Corynebacterium,* pALS1, pIL2 and pBB116, in fungi, 2alphaM, pAG-1, YEp6, YEp13 and pEMBLYe23, in yeasts, and pLGV23, pGHlac⁺, pBIN19, pAK2004 and pDH51, in plants. These plasmids constitute a small selection of the possible plasmids. Other plasmids are well known to the skilled person and information about them can be obtained, for example, from the book Cloning Vectors (Eds. Pouwels P. H. et al. Elsevier, Amsterdam-New York-Oxford, 1985, ISBN 0 444 904018).

For the purpose of expression the other genes which are present, the nucleic acid construct advantageously also contains 3'-terminal and/or 5'-terminal regulatory sequences for increading expression, which sequences are selected for optimal expression in dependence on the host organism and gene or genes which are selected.

These regulatory sequences should enable the genes to be expressed selectively and the protein to be expressed. This can, for example, mean that, depending on the host organism, the gene is only expressed, or overexpressed, following induction or that it is expressed and/or overexpressed immediately.

In this connection, the regulatory sequences or factors can preferably influence positively, and thereby increase, the expression of the genes which have been introduced. Thus, the regulatory elements can advantageously be augmented at the transcription level by using strong transcription signals such as promoters and/or enhancers. However, in addition to this, it is also possible to augment translation by, for example, improving the stability of the mRNA.

In another embodiment of the vector, the nucleic acid construct according to the invention or the vector which contains the nucleic acid according to the invention can also advantageously be inserted into the microorganisms in the form of a linear DNA and be integrated into the genome of the host organism by means of heterologous or homologous recombination. This linear DNA can consist of a linearized vector, such as a plasmid, or only of the nucleic acid construct or the nucleic acid according to the invention.

In order to be able to express heterologous genes optimally in organisms, it is advantageous to alter the nucleic acid sequences in conformity with the specific codon usage which is employed in the organism. The codon usage can readily be determined with the aid of computer analyses of other known genes from the organism in question.

An expression cassette according to the invention is prepared by fusing a suitable promoter to a suitable coding nucleotide sequence and to a terminator signal or polyadenylation signal. Customary recombination and cloning techniques, as are described, for example, in T. Maniatis, E. F. Fritsch and J. Sambrook, Molecular Cloning: A Laboratory Manual, Cold Spring Harbor Laboratory, Cold Spring Harbor, N.Y. (1989) as well as in T. J. Silhavy, M. L. Berman und L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987) are used for this purpose.

For the purpose of achieving expression in a suitable host organism, the recombinant nucleic acid construct or gene construct is advantageously inserted into a host-specific vector which enables the genes to be expressed optimally in the host. Vectors are well known to the skilled person and information about them can be obtained, for example, from "Cloning Vectors" (Pouwels P. H. et al., Eds., Elsevier, Amsterdam-New York-Oxford, 1985).

Host Organisms which can be Used in Accordance with the Invention

It is possible to use the vectors or constructs according to the invention to prepare recombinant microorganisms which are, for example, transformed with at least one vector according to the invention and can be used for producing the polypeptides according to the invention. Advantageously, the above-described recombinant constructs according to the invention are introduced into a suitable host system and expressed. In this connection, cloning and transfection methods with which the skilled person is familiar, such as coprecipitation, protoplast fusion, electroporation, retroviral transfection and the like, are preferably used in order to cause said nucleic acids to be expressed in the given expression system. Suitable systems are described, for example, in Current Protocols in Molecular Biology, F. Ausubel et al., Eds., Wiley Interscience, New York 1997, or Sambrook et al. Molecular Cloning: A Laboratory Manual. 2$^{nd}$ edtn., Cold Spring Harbor Laboratory, Cold Spring Harbor Laboratory Press, Cold Spring Harbor, N.Y., 1989.

According to the invention, it is also possible to prepare homologously recombined microorganisms. For this, it is necessary to prepare a vector which contains at least one segment of a gene according to the invention or of a coding sequence in which at least one amino acid deletion, addition or replacement has, where appropriate, been introduced in order to modify, e.g. disrupt functionally ("knock-out" vector) the sequence according to the invention. The introduced sequence can also, for example, be a homolog from a related microorganism or be derived from a mammalian, yeast or insect source. Alternatively, the vector which is used for the homologous recombination can be configured such that the endogenous gene in connection with the homologous recombination is mutated or otherwise modified but still encodes the functional protein (e.g. the downstream regulatory region can be modified such that the expression of the endogenous protein is thereby altered). The modified segment of the gene according to the invention is in the homologous recombination vector. The construction of vectors which are suitable for the homologous recombination is described, for example, in Thomas, K. R. and Capecchi, M. R. (1987) Cell 51:503.

In principle, any prokaryotic or eukaryotic organisms are suitable for being used as recombinant host organisms for the nucleic acid according to the invention or the nucleic acid construct. Advantageously, microorganisms such as bacteria, fungi or yeasts are used as host organisms. Gram-positive or Gram-negative bacteria, preferably bacteria of the families Enterobacteriaceae, Pseudomonadaceae, Rhizobiaceae, Streptomycetaceae or Nocardiaceae, particularly preferably bacteria of the genera *Escherichia, Pseudomonas, Streptomyces, Nocardia, Burkholderia, Salmonella, Agrobacterium* or *Rhodococcus,* are advantageously used. Very particular preference is given to the genus and species *Escherichia coli.* In addition to this, other advantageous bacteria can be found in the group of the alpha-protobacteria, beta-protobacteria and gamma-protobacteria.

In this connection, the host organism, or the host organisms, according to the invention preferably contain(s) at least one of the nucleic acid sequences, nucleic acid constructs or vectors which are described in this invention and which encode an enzyme possessing dehydrogenase activity according to the invention.

The organisms which are used in the process according to the invention are, depending on the host organism, grown or cultured in a manner known to the skilled person. Microorganisms are as a rule grown in a liquid medium, which contains a carbon source, usually in the form of sugars, a nitrogen source, usually in the form of organic nitrogen sources such as yeast extract or salts such as ammonium sulfate, trace elements, such as iron salts, manganese salts and magnesium salts and, where appropriate, vitamins, at temperatures of between 0° C. and 100° C., preferably of from 10° C. to 60° C., while being gassed with oxygen. In this connection, the pH of the nutrient liquid can be kept at a fixed value, that is regulated during the culture, or not. The culture can be carried out batchwise, semibatchwise or continuously. Nutrients can be initially introduced at the beginning of the fermentation or be fed in subsequently semicontinuously or continuously. The ketone can be added directly to the culture or, advantageously, after culture. The enzymes can be isolated from the organisms using the method described in the examples or else used for the reaction as a crude extract.

Preparing the Polypeptides According to the Invention Recombinantly

The invention furthermore relates to a process for recombinantly preparing polypeptides according to the invention, or functional, biologically active fragments thereof, with a polypeptide-producing microorganism being cultured, expression of the polypeptides being induced, where appropriate, and these polypeptides being isolated from the culture. The polypeptides can also be produced in this way on an industrial scale if this is desired.

The recombinant microorganism can be cultured and fermented in accordance with known methods. Bacteria can, for example, be propagated in TB medium or LB medium and at a temperature of from 20 to 40° C. and a pH of from 6 to 9. Suitable culturing conditions are described in detail, for example, in T. Maniatis, E. F. Fritsch and J. Sambrook, Molecular Cloning: A Laboratory Manual, Cold Spring Harbor Laboratory, Cold Spring Harbor, N.Y. (1989).

If the polypeptides are not secreted into the culture medium, the cells are then disrupted and the product is obtained from the lysate using known protein isolation methods. The cells can, as desired, be disrupted by means of high-frequency ultrasound, by means of high pressure, as, for example, in a French pressure cell, by means of osmolysis, by the action of detergents, lytic enzymes or organic solvents, by using homogenizers or by a combination of several of the methods cited.

The polypeptides can be purified using known chromatographic methods, such as molecular sieve chromatography (gel filtration), such as Q Sepharose chromatography, ion exchange chromatography and hydrophobic chromatography, and also using other customary methods such as ultrafiltration, crystallization, salting-out, dialysis and native gel electrophoresis. Suitable methods are described, for example, in Cooper, F. G., Biochemische Arbeitsmethoden [Biochemical methods of operation], Verlag Walter de Gruyter, Berlin, New York, or in Scopes, R., Protein Purification, Springer Verlag, New York, Heidelberg, Berlin.

For the purpose of isolating the recombinant protein, it can be advantageous to use vector systems or oligonucleotides which extend the cDNA by particular nucleotide sequences and thereby encode altered polypeptides or fusion proteins which are used, for example, to simplify purification. The examples of such suitable modifications are what are termed tags which act as anchors, such as the modification known as the hexahistidine anchor, or epitopes which can be recognized as antigens by antibodies (described, for examle, in Harlow, E. and Lane, D., 1988, Antibodies: A Laboratory Manual. Cold Spring Harbor (N.Y.) Press). These anchors can be used for attaching the proteins to a solid support, such as a polymer matrix, which can, for example, be packed into a chromatography column, or to a microtiter plate or to another support.

At the same time, these anchors can also be used for recognizing the proteins. For the purpose of recognizing the proteins, it is also possible to use customary labels such as fluorescent dyes, enzyme labels, which, after reaction with a substrate, form a detectable reaction product, or radioactive labels, either on their own or in combination with the anchors, for the purpose of derivatizing the proteins.

Other Embodiments for Implementing the Enzymic Reduction Method According to the Invention In the process according to the invention, the dehydrogenases can be used as free or immobilized enzymes.

The process according to the invention is advantageously carried out at a temperature of from 0° C. to 95° C., preferably of from 10° C. to 85° C., particularly preferably of from 15° C. to 75° C.

In the process according to the invention, the pH is advantageously kept between pH 4 and 12, preferably between pH 4.5 and 9, particularly preferably between pH 5 and 8.

In the process according to the invention, enantiomerically pure or chiral products, such as 3-chloro-1-(thien-2-yl)-(S)-propan-1-ol, are to be understood as being enantiomers which exhibit enantiomer enrichment. Enantiomeric purities of at least 70% ee, preferably of at least 80% ee, particularly preferably of at least 90% ee, very particularly preferably of at least 98% ee, are preferably achieved in the process.

For the process according to the invention, it is possible to use growing cells which contain the nucleic acids, nucleic acid constructs or vectors according to the invention. It is also possible to use resting or disrupted cells. Disrupted cells are to be understood, for example, as being cells which have been made permeable as a result of being treated with solvents, for example, or cells which have been broken up by means of being treated with an enzyme, by means of being treated mechanically (e.g. French press or ultrasonication) or by means of another method. The crude extracts which are obtained in this way are advantageously suitable for the process according to the invention. It is also possible to use purified enzymes or partially purified enzymes for the process. Immobilzed microorganisms or enzymes, which can advantageously be used in the reaction, are likewise suitable.

The process according to the invention can be operated batchwise, semibatchweise or continuously.

The process can advantageously be carried out in bioreactors as described, for example, in Biotechnology, volume 3, 2nd edition, Rehm et al. Eds., (1993), in particular chapter II.

Figure 2A:
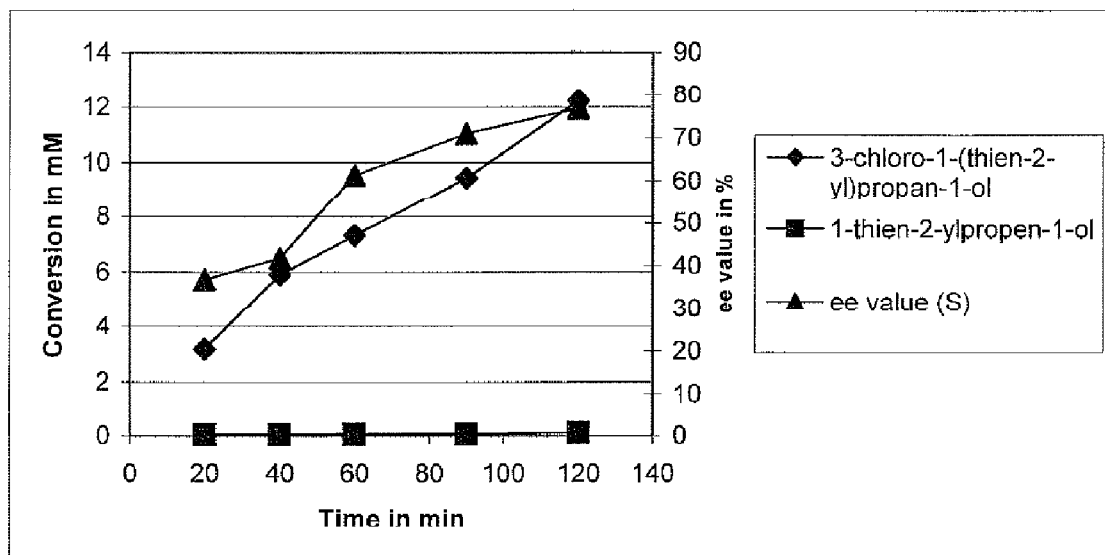
FIGS. 2A and 2B show typical reaction sequences for different mixtures used for preparing (S)-3-methylamino-1-(thien-2-yl)propan-1-ol I-S by means of reducing with a *Lactobaccillus brevis* dehydrogenase.
Figure 2B:
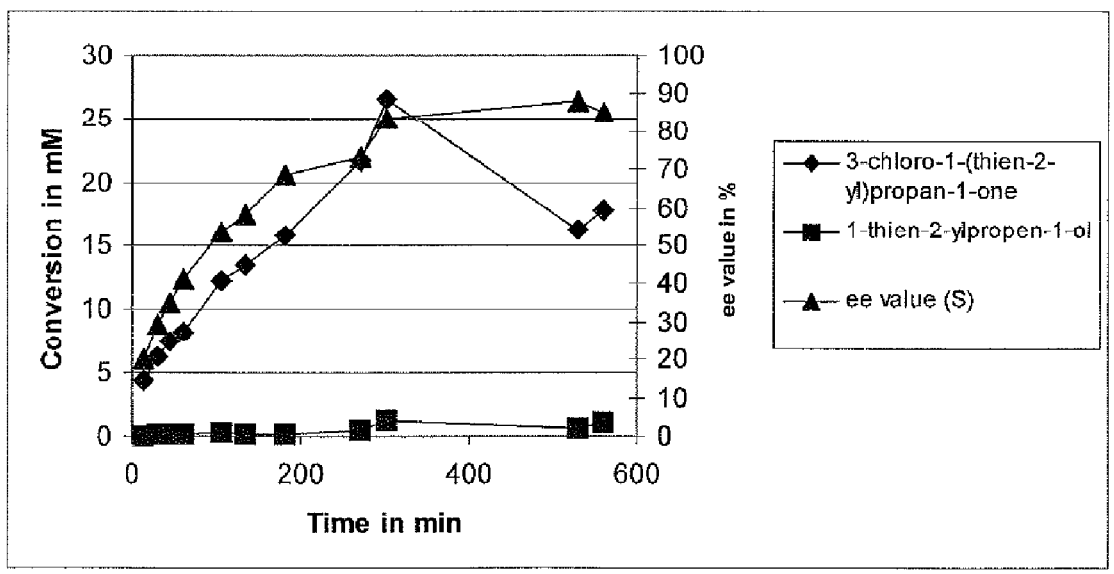

The following examples are intended to illustrate the invention without limiting it. The reader is referred, in this connection, to the enclosed figures, wherein:

FIG. 1 shows the activity-stained gel for an Lu10288 dehydrogenase which was isolated in accordance with the invention; lane 1: molecular weight standards, from the bottom: 47 kDa, 74 kDa, 121 kDa and 205 kDa; lane 2: empty; lane 3: homogenate supernatant; lane 4: Q Sepharose useful fraction; lane 5: Q Sepharose useful fraction (three-fold quantity); lane 6: Superdex useful fraction; lane 7: Mono-Q useful fraction; lane 8: Mono-P useful fraction;

FIGS. 2A and 2B show typical reaction sequences for different mixtures used for preparing (S)-3-methylamino-1-(thien-2-yl)propan-1-ol I-S by means of reducing with a *Lactobaccillus brevis* dehydrogenase.

FIG. 3A shows the result of the N-terminal sequencing of a blot band of Lu10288 dehydrogenase which was isolated in accordance with the invention; and FIG. 3B shows the sequencing data for different proteolytic fragments of an Lu10288 dehydrogenase which was purified in accordance with the invention; insofar as it was possible to establish a main sequence when several signals were obtained per sequence step, this is depicted by being underlined twice. Unreadable positions are labeled "/"; in the case of positions whose identification is somewhat uncertain, the amino acid residue is given in brackets. Two amino acids are given at one position when it is not possible to specify any unambiguous preference. "?" denotes an unknown or unidentifiable amino acid.

EXAMPLES

A. Chemical Examples

Example 1

Preparing 3-chloro-1-(thien-2-yl)propan-1-one III.1

33 kg of thiophene were initially introduced into 150 kg of dichloroethane after which 62.7 kg of aluminum trichloride were added. The reaction mixture was cooled down to 10° C. and 55 kg of 3-chloropropionyl chloride were added. The mixture was then stirred at room temperature for 12 h. Checking by GC and NMR showed that the reaction mixture still contained about 3-4 mol % of 3-chloro-1-(thien-2-yl)propenone based on the sum of formed 3-chloro-1-(thien-2-yl)propan-1-one and 3-chloro-1-(thien-2-yl)propenone. Hydrogen chloride was then passed in at room temperature until (approx. 30 minutes) it was no longer possible to detect any propenone. The reaction mixture was then hydrolyzed by adding 100 kg of deionized water. The organic phase was separated off and washed with 100 kg of deionized water. After the solvent had been removed in vacuo, 65.7 kg (96% of theory) of the title compound were obtained as an oil.

Example 2

Preparing 3-methylamino-1-(thien-2-yl)propan-1-ol I by reducing with sodium borohydride The propanone from Example 1 was initially introduced, at 0° C., into a mixture of 400 ml of toluene and 200 g of methanol. After 2 g of a 30%-strength aqueous solution of sodium hydroxide had been added, 21.4 g of sodium borohydride were added, in portions, within the space of 2.5 h. After having been stirred at 0° C. for 40 min, the reaction mixture was treated with 12.1 g of a 40%-strength aqueous solution of methylamine. The mixture was stirred at 60° C. for 6 h under its intrinsic pressure. After the mixture had been cooled down to room temperature, the solvent was removed and the residue was digested with toluene and filtered off from it. The filtrate was dried and 175.8 g of the title compound were obtained in the form of a pale yellow solid.

B. Biochemical Examples

Example 3

Preparing Glucose Dehydrogenase for the Cofactor Regeneration

For the purpose of regenerating the cofactor, it was possible to use glucose dehydrogenase from commercial sources (e.g. Jülich Fine Chemicals Order No. 22.10 or 19.10) or our own sources, with the latter being an *E. coli* XL10 Gold pUC19 clone which contained the glucose dehydrogenase gene from Bacillus subtilis (Genbank Acc. No. M12276) (Lu11293).

The following medium was prepared for fermenting *E. coli* Lu11293:

| | | |
|---|---|---|
| 560 g | yeast extract (65%) | |
| 448 g | tryptone (Difco) | |
| 42 g | $KH_2PO_4$ | |
| 84 g | $Na_2HPO_4$ | |
| 644 g | glycerol (99%) | |
| 100 ml | SL4 solution (5-fold) | |
| 1 g | Tegosipon 3062 | |
| | Make up the medium with water to 13.5 L, adjust the pH to 7.0, remove approx. 300 ml for preliminary culture and, after that, sterilize at 122° C. for 30 min. Add sterile salt solution* (before that, remove the salt solution for the shaker flasks, see report). | |
| *Salt solution: | 2.1 g | $CaCl_2 * 2\ H_2O$ |
| | 3.5 g | $MgSO_4 * 7\ H_2O$ |
| | 14 g | $NH_4Cl$ |
| | +14 ml | of ampicillin solution (100 mg/ml) dissolved in 500 ml of water and sterilized by filtration |

In each case 150 ml of medium were sterilized in two 1 l Erlenmeyer flasks and supplemented with 5 ml of sterile salt solution. After inoculating from an LB ampicillin agar plate, the preliminary cultures were incubated for 12 hours at 37° C. and 200 rpm and added to the fermentation medium. The fermentation was started at 37° C., 0.1 bar internal pressure and pH 7.0 (regulated with 20% phosphoric acid and 25% NaOH), with a gassing rate of 7.5 l/min and at 300 rpm ($pO_2$ regulated to between 20 and 50% with air entering at 10-20 l/min and at 500-1500 rpm). After 2 h, 0.1 mM IPTG was added for the induction and the fermentation was terminated after a total of 13 h. After the cells (1.3 kg) had been harvested and washed, they were stored until use (2-20 g/l in the mixture) at −20° C.

Example 4

Screening for Dehydrogenases for Reducing 3-chloro-1-(thien-2-yl)propan-1-one a) Various bacterial and fungal strains (mainly from a variety of strain collections) were grown, at 30 or 37° C. and from 24 to 48 h, in 20 ml of LB medium, MRS medium (from Difco) or GYP medium (used for yeasts) (1% w/v D-glucose, in each case 0.5% w/v yeast extract and polypeptone, pH 6.0), washed in 3 mM Tris-HCl, pH 7.5, and resuspended in 2 ml of buffer. An aliquot was disrupted with 1 vol of glass beads (0.3-0.5 mm diameter) in a vibratory mill (3×5 min with 10 min intervals of cooling on ice). After the turbidity had been separated off by centrifugation (5 min at 14 000 rpm and 4° C.), a clear crude extract was obtained. The cell suspensions and crude extracts were then tested for their activity to reduce 3-chloro-1-(thien-2-yl)propan-1-one from Example 3).

Assay Employed:
150 µl, of cells/crude extract
50 µl, of 1 M glucose solution
50 µl, of glucose dehydrogenase (12-15 U/µl; 20-200 mg MBM/ml) from Example 3
50 µl of 2 mM NADH
50 µl of 2 mM NADPH
10 µl of 0.5 M 3-chloro-1-(thien-2-yl)propan-1-one in methanol
190 µl of 50 mM MES, pH 6.0 or Tris-HCl, pH 7.5

The incubation was carried out at 30° C. The samples (200 µl) were stopped with 3 µl of conc. HCl after 1, 2 or 24 h. Following centrifugation, the supernatants were analyzed by means of HPLC for 3-chloro-1-(thien-2-yl)propan-1-one and 3-chloro-1-(thien-2-yl)propan-1-ol (Chromolith Speed ROD, RP-18e 50-4.6 mm, flow rate 1.5 ml/min, 0.0-1.0 min: 35% acetonitrile+65% 10 mM $KH_2PO_4$ buffer, pH 2.5; 1.1-1.3 min: 80% acetonitrile+20% 10 mM $KH_2PO_4$ buffer, pH 2.5; 1.3-2.0 min: 35% acetonitrile+65% 10 mM $KH_2PO_4$ buffer pH 2,5; detection at 230 nm (alcohol) and 260 nm (ketone) at a retention time Rt=1.250 min (3-chloro-1-(thien-2-yl)propan-1-ol) and Rt=1.500 min (3-chloro-1-(thien-2-yl) propan-1-one); possible by-products from HCl elimination (1-thien-2-ylpropen-1-one and 1-thien-2-ylpropen-1-ol) at Rt=0.971 min and Rt=1.165 min).

Selected strains were tested repeatedly, with the samples being extracted with methyl tert-butyl ether (MTBE) or methyl isobutyl ketone (MIBK), and characterized by means of chiral GC analysis or HPLC analysis, for the purpose of determining the enantiomeric excess (ee). The following methods were used for this purpose: GC: Hydrodex-β-6-TBDM, 25 m, 90° C. 10 min 5° C./min 180° C. 10 min, running time: 38 min, inlets: heater: 200° C., pressure: 106.8 kPa, total flow: 102 ml/min, split ratio: 125:1, split flow: 99.8 ml/min, detector: 200° C. or HPLC: Chiracel OD-H, 250*4.6 mm (Daicel), 40° C., flow rate 1.0 ml/min, 0.0-1.0 min: 97.5% n-hexane+2.5% isopropanol; detection at 230 nm (alcohol) and 260 nm (ketone) at Rt 9.50 (3-chloro-1-(thien-2-yl)propan-1-one), Rt 16.60 min (R-3-chloro-1-(thien-2-yl) propan-1-ol) and Rt 18.30 min (S-3-chloro-1-(thien-2-yl) propan-1-ol).

b) Various *Lactobaccillus* strains were newly isolated

The *Lactobaccillus brevis* strains Lu10288, 10290 and 10291 were isolated as follows.

b1) Media employed

Kleymann's Medium:
The following substances were dissolved in 915 ml:
10 g/l tryptone (Difco-Becton Dickinson)
7 g/l yeast extract (Difco-Becton Dickinson)
2 g/l beef extract (Difco-Becton Dickinson)
5 g/l fructose
2 g/l maltose
3.6 g/l gluconic acid 50%
1.9 g/l citric acid*$H_2O$
5 g/l acetate
1 g/l Tween 80
0.2 g/l $MgSO_4$*$7H_2O$
0.05 g/l $MnSO_4$
0.01 g/l $FeSO_4$
0.4 g/l L-cysteine
1.25 ml $NH_4OH$ (25%)
for agar plates: 2% Bacto Agar (Difco-Becton Dickinson) added The pH of the solution was adjusted to 5.4.
The solution was autoclaved at 121° C. for 15'.
After the autoclaving, 50 ml of sterile glucose solution (5 g made up to 50 ml with $H_2O$) and 40 ml of ethanol were added while stirring and agar plates were poured.

KMB Medium:
10 g/l tryptone (Difco-Becton Dickinson)
7 g/l yeast extract (Difco-Becton Dickinson)
2 g/l $KH_2PO_4$
1 g/l Tween 80
0.5 g/l $MgSO_4$*$7H_2O$
1 g/l $MnSO_4$
20 g/l $CaCO_3$
10 g/l glucose
1.5% agar for preparing agar plates The solution was autoclaved at 121° C. for 15'.

The glucose and the $CaCO_3$ (Riedel de Haen) were dissolved and autoclaved separately and admixed with the agar before pouring the plates.

b2) Isolating the microorganisms:

5-10 g of corn silage from the north German region (LUFA-Oldenburg) were incubated anaerobically, overnight at 37° C. with 20 ml of saline in a 50 ml Erlenmeyer flask. The liquid fraction which was obtained was inoculated, in a ratio of 1:100, into 50 ml of Kleymann's medium and the latter was incubated anaerobically at RT for 24 h and while stirring gently. After that, the cell suspension was plated out on the described Kleymann's selection agar plates. The plates were incubated anaerobically at 37° C. for 48-72h and the resulting colonies were isolated by streaking out repeatedly on KMB medium.

The strains were characterized by determining the acid fermentation pattern (measurement of the pH and determination, by HPLC analysis of the culture supernatants, of the concentrations of glucose, fructose, lactate, acetate and ethanol) in liquid KMB medium containing 20 g of fructose/L (24 h, 37° C., 50 rpm). Heterofermentative strains which formed acetate and lactate were isolated and characterized systematically by analyzing the 16sRNA.

c) Screening results

Tables 1,2 and 3 show examples of strains and/or the conversions and ee values.

TABLE 1

| Lu No.: | Genus | Species | Collection | Number |
|---|---|---|---|---|
| 44 | Byssochlamys | fulva | IMI | 163641 |
| 105 | Geotrichum | candidum | ATCC | 28747 |
| 106 | Geotrichum | candidum | ATCC | 20141 |
| 582 | Pichia | glucozyma | ATCC | 18938 |
| 716 | Hansenula | polymorpha | — | |
| 908 | Saccharomyces | rouxi | IFO | 493 |
| 1844 | Kluyveromyces | lactis | ATCC | 56498 |
| 2707 | Saccharomyces | cerevisiae | ATCC | 9080 |
| 3458 | Geotrichum | candidum | ATCC | 34614 |
| 896 | Geotrichum | vanrij | ATCC | 22375 |
| 897 | Geotrichum | fermentans | ATCC | 56301 |
| 3458 | Geotrichum | klebahnii | ATCC | 20001 |
| 4986 | Candida | utilis | — | |
| 8472 | Candida | magnoliae | ATCC | 12573 |
| 1821 | Candida | guilliermondii | ATCC | 20403 |
| 1823 | Candida | guilliermondii | ATCC | 20474 |
| 8478 | Candida | tropicalis | ATCC | 24887 |
| 8833 | Rhodotorula | aurantiaca | ATCC | 32770 |
| 127 | Pseudomonas | desmolytica | NRRL | 3108 |
| 404 | Rhodococcus | fragi | IFO | 12049 |
| 444 | Pseudomonas | paucimobilis | ATCC | 10829 |
| 493 | Pseudomonas | citronellolis | ATCC | 13674 |
| 4006 | Pseudomonas | lemoignei | NCIMB | 9947 |

TABLE 1-continued

| Lu No.: | Genus | Species | Collection | Number |
|---|---|---|---|---|
| 8099 | Burkholderia | gladioli | ATCC | 25417 |
| 8510 | Rhodococcus | ruber | DSMZ | 8316 |
| 10288 | Lactobacillus | brevis | * | |
| 10290 | Lactobacillus | brevis | —* | |
| 10291 | Lactobacillus | brevis | —* | |

TABLE 2

Conversions:

| Lu No.: | Genus | Species | OD 600 | Conversion 2 h/mM | Conversion 24 h/mM |
|---|---|---|---|---|---|
| 44 | Byssochlamys | fulva | n.d. | 0.0 | 0.2 |
| 105 | Geotrichum | candidum | 12.18 | 0.2 | 0.2 |
| 106 | Geotrichum | candidum | 7.8 | 3.1 | 4.1 |
| 582 | Pichia | glucozyma | 9.98 | 0.1 | 0.1 |
| 716 | Hansenula | polymorpha | 12.24 | 0.0 | 0.3 |
| 908 | Saccharomyces | rouxi | 8.78 | 0.0 | 0.3 |
| 1844 | Kluyveromyces | lactis | 13.86 | 0.0 | 0.3 |
| 2707 | Saccharomyces | cerevisiae | 10 | 0.2 | 0.4 |
| 3458 | Geotrichum | candidum | 8.26 | 0.2 | 0.4 |
| 896 | Geotrichum | vanrij | 11.36 | 0.03 | n.d. |
| 897 | Geotrichum | fermentans | 9.30 | 0.04 | n.d. |
| 3458 | Geotrichum | klebahnii | 10.84 | 0.08 | n.d. |
| 4986 | Candida | utilis | 11.06 | 0.0 | 0.2 |
| 1821 | Candida | guilliermondii | 5.76 | 0.09 | n.d. |
| 1823 | Candida | guilliermondii | 5.54 | 0.07 | n.d. |
| 8472 | Candida | magnoliae | 13.78 | 0.8 | 0.8 |
| 8478 | Candida | tropicalis | 2.6 | 0.05 | n.d. |
| 8833 | Rhodotorula | aurantiaca | 2.32 | 0.1 | 0.3 |
| 127 | Pseudomonas | desmolytica | 3.74 | 0.0 | 0.4 |
| 404 | Rhodococcus | fragi | 1.78 | n.d. | 0.3 |
| 493 | Pseudomonas | citronellolis | 3.54 | 0.0 | 0.2 |
| 4006 | Pseudomonas | lemoignei | 2.24 | n.d. | 0.2 |
| 8099 | Burkholderia | gladioli | 15.34 | 0.1 | 0.2 |
| 8510 | Rhodococcus | ruber | 1.1 | 0.0 | 0.1 |
| 10288 | Lactobacillus | brevis | 4.89 | 0.2 | 0.4 |
| 10290 | Lactobacillus | brevis | 2.08 | 0.1 | 0.2 |
| 10291 | Lactobacillus | brevis | 2.84 | 0.2 | 0.2 | n.d.; not determined
Conversions based on 3-chloro-1-(thien-2-yl)-propan-1-ol formed in mM

TABLE 3

Test repeat including ee value determination

| Lu No.: | Genus | Species | OD 600 | Conversion 2 h/mM | ee value 24 h/% |
|---|---|---|---|---|---|
| 10288 | Lactobacillus | brevis | 4.89 | 5.2 | n.d. |
| 105 | Geotrichum | candidum | 7.86 | 4.2 | 98 |
| 8472 | Candida | magnoliae | 6.56 | 0.13 | 56 |

Example 5

Purifying the Dehydrogenase from *Lactobaccillus brevis*

The following medium was prepared for fermenting *Lactobaccillus brevis* Lu10288:

| 1400 g | yeast extract (65%) |
|---|---|
| 44.1 g | citric acid |
| 63 g | $KH_2PO_4$ |
| 21.5 g | $MgSO_4 * 7 H_2O$ |
| 4.1 g | $MnSO_4 * H_2O$ |
| 21 g | Tween 80 |
| 15.4 g | $(NH_4)_2Fe(SO_4)_2 \cdot 12 H_2O$ |
| 1 g | Tegosipon 3062 |

Make up medium with water to 12.6 l, adjust pH to 5.8, remove approx. 300 ml for preliminary cultures; sterilization, 30 min. at 122° C.; dissolve 840 g of glucose in 860 ml of water and sterilize; in each case add 15 ml of glucose solution to 135 ml of preliminary culture medium in a 1 l flask, add remainder to the fermentation medium.

2 preliminary cultures were inoculated from an MRS agar plate, the preliminary cultures were incubated for 17 h at 37° C. and 200 rpm and added to the fermentation medium. The fermentation was started at 37° C., 0.1 bar internal pressure and pH 5.8, with a gassing rate of 1 l/min and at 100 rpm (no p $O_2$ regulation) and terminated after 23 h at an OD600 of 14.8.

The activity of the washed cell samples was determined in analogy with Example 4a) using resting cells in MES, pH 6.0.

The Lu10288 dehydrogenase was purified as follows:

Homogenization:

100 g of Lu10288 (*Lactobaccillus brevis*) moist biomass were resuspended in 5×20 g portions using 100 ml of MES buffer, 1 mM MgCl2, pH 7.1, and homogenized, in 10 portions for 20 minutes, at 4000 rpm and while cooling with ice, in a ball mill using glass beads (0.1 mm-0.2 mm diameter, 50 ml of resuspended cells to 50 ml of glass beads). The glass beads were separated off through a G2 glass suction filter and washed with 20 ml of buffer. The collected homogenate (610 ml) was then clarified in a GSA rotor at 12 000 rpm for 20 minutes.

a) Q-Sepharose ion Exchange Chromatography:

A Q-Sepharose fast flow (Pharmacia) column having a diameter of 5 cm and a volume of 400 ml was equilibrated in 20 mM MES buffer, 1 mM $MgCl_2$, pH 6.8. 610 ml of homogenate were treated with 11 tablets of Complete (protease inhibitor mixture, Roche, Complete, EDTA-free; Cat. No.: 1873580) and loaded onto the Q-Sepharose column at a loading rate of 10 ml/min. Detection was at 280 nm. The column was then washed with three column volumes in the same buffer. For elution, a linear gradient of 20 mM MES, 1 mM $MgCl_2$, 1 M NaCl, pH 6.8 (from 0% NaCl to 100% NaCl in 100 minutes) was applied. 10 ml fractions were collected and tested. Fractions 42 to 62 were active with 3-chloro-1-(thien-2-yl)propan-1-one in an HPLC test.

b) Superdex Molecular Sieve Chromatography:

A Superdex 200 molecular sieve column (Pharmacia) having a diameter of 2.6 cm and a volume of 240 ml was equilibrated in 20 mM MES, 1 mM $MgCl_2$, 1 tablet of Complete per liter of buffer (EDTA-free), pH 7.1. The useful fractions from the Q-Sepharose were combined (240 ml) and adjusted to 80% saturation by slowly adding 124 g of ammonium sulfate. The pH was kept at 7.1. The solution was stirred at 4° C. for 10 minutes and then centrifuged at 12 000 rpm for 20 minutes. The resulting pellet was resuspended in 5 ml of equilibration buffer and this suspension was dialyzed for 1 hour at 4 degrees Celsius (10 kDa exclusion volume). The dialyzed solution was divided into two 9 ml parts and loaded onto the molecular sieve column at a flow rate of 4 ml per minute. 4 ml fractions were collected and tested. Fractions 48 to 56 were once again active for both substrates.

c) Mono-Q ion Exchange Chromatography:

A preparative Mono-Q HR column (Pharmacia) having a volume of 20 ml was equilibrated in 20 mM MES, 1 mM MgCl$_2$, pH 7.1. 70 ml of the combined useful fractions from the Superdex were loaded on at a flow rate of 4 ml per minute. After the column had been washed, it was developed with a linear gradient of up to 100% 20 mM MES, 1 mM MgCl$_2$, 0.5 M NaCl, pH 7.1 in 100 minutes. 4 ml fractions were collected. Active fractions (fractions 36 to 41) were combined.

d) Mono-P ion Exchange Chromatography:

A Mono-P column (Pharmacia, 4 ml) was equilibrated in 20 mM MOPS, 1 mM MgCl$_2$, pH 7.1. 21 ml of the Mono-Q useful fraction were loaded at a flow rate of 0.75 ml/min. Following washing down to the base line, a linear gradient of up to 100% 20 mM MOPS, 1 mM MgCl$_2$, 0.5 M NaCl, pH 7.1, in 100 minutes was applied. Fractions (0.75 ml) were collected. Active fractions (34-39) were combined.

Activity Staining in Gels:

The sample was diluted with the same volume of Novex "native Tris-glycine" sample buffer (Novex). The Anamed tris-glycine gels (without SDS, 1 mm thick, 10 sample wells) were installed in the running chamber. Invitrogen "Tris-glycine native" running buffer (Invitrogen) (10×) was used, after dilution, as the running buffer. The sample wells were loaded and the gel was started at 200 V and approx. 50 mA. The duration of the electrophoresis was about 1.5 hours. The running chamber stood in ice water. After the gel had been removed, it was placed in a glass dish and washed in 50 mM MES, 8 mM MgCl$_2$, pH 6.2 and incubated.

0.35 mM NADP and 0.35 mM NAD, 19.6 mg of NB-tetrazolium and 2.1 mg of phenazine ethosulfate (PES) were then added to this gel in this solution. The substrate (3-chloro-1-(thien-2-yl)propan-1-ol) was then added to give a final concentration of 1 mM. The gels were kept in the dark until they had become stained. A typical gel is shown in FIG. 1.

Summary of the Isolation of LU 10288 Dehydrogenase

KH$_2$PO$_4$ /i, 2 g of MgSO$_4$*7H$_2$O/l, pH 6.0, and used to inoculate 13.2 l of analogous medium containing 10.7 g of glucose/l and 4 ml of tegosipon. The fermentation was started at 28° C., 0.1 bar internal pressure and pH 6.0, with a gassing rate of 5 l/min and at 500 rpm (pO$_2$ regulated to >20%) and terminated after 26 h at an OD600 of 15.1.

Homogenization:

The harvested cells (378 g of moist biomass) were suspended in 1 l of 50 mM MES+1 mM MgCl$_2$, pH 6.5, containing 10 tablets of Roche Complete (without EDTA) protease inhibitor (approx. 9× conc.) and disrupted 2× with 1000 bar in a Z04 microfluidizer. Following centrifugation (20 min/10 000 g), half of the clear supernatant (1.3 l of homogenate) was purified as described below. In doing this, the sample fractions were tested, at suitable dilution, for activity, at 30° C., in 50 mM MES, pH 6.0, 0.2 mM NaDH/NaDPH, 100 mM glucose, 50 µl of GDH/ml and 10 mM of 3-chloro-1-(thien-2-yl)propan-1-one.

Q-Sepharose ion Exchange Chromatography:

A Q-Sepharose fast flow column (Pharmacia) having a diameter of 5 cm and a volume of 400 ml was equilibrated in 20 mM MES buffer, 1 mM MgCl$_2$, pH 6.8. 650 ml of homogenate were treated with 11 tablets of Complete (protease inhibitor mixture) and loaded onto the Q-Sepharose column at a loading rate of 7.5 ml/min. Detection was at 280 nm. The column was then washed with 700 ml of the same buffer. For the elution, a linear gradient of 20 mM MES, 1 mM MgCl$_2$, 0.75 M NaCl, pH 6.8 (from 0% NaCl to 100% NaCl in 100 minutes) was applied after which the column was washed with 200 ml 20 mM MES, 1 mM MgCl$_2$, 0.75M NaCl, pH 6.8. 10 ml fractions were collected and tested. Fractions 56 to 96 were active with 3-chloro-1-(thien-2-yl)propan-1-one in the HPLC test.

| Designation | Volume [ml] | Protein [mg/ml] | Activity [U/l] | Specific activity [mU/mg] | ee-value (S) [%] | Total protein [mg] | Total activity [U] | Protein yield [%] | Activity yield in [%] |
|---|---|---|---|---|---|---|---|---|---|
| Cell suspension | 500 | | 270.1 | | 95.0 | 0.0 | 135.1 | — | 100.0 |
| Homogenate | 610 | 3.35 | 98.1 | 29.3 | 94.1 | 2043.5 | 59.6 | 100.0 | 44.3 |
| UP-Q-Sepharose | 240 | 2.25 | 49.3 | 21.9 | 97.0 | 540.0 | 11.8 | 26.4 | 8.8 |
| UP-Superdex, determined directly* | 70 | 2.17 | 134 | 61.8 | 45.3 | 151.9 | 9.38 | 7.4 | 6.95 |
| UP-Superdex 8 days 4° C.** | 70 | 2.17 | 6.4 | 2.9 | 62.4 | 151.9 | 0.45 | 7.4 | 0.33 |
| UP-Mono Q | 21 | 0.31 | 9.6 | 31.0 | 67.1 | 6.5 | 0.20 | 0.32 | 0.15 |
| UP-Mono P | 4.2 | 0.91 | 29.8 | 32.7 | 71.3 | 3.8 | 0.13 | 0.19 | 0.09 |

UP: useful peak fractions
*activity determined on the fresh sample
**activity determined following storage The N terminus of the dehydrogenase which had been purified in this way was determined by means of Edman sequencing (SEQ ID NO: 1) following SDS-PAGE and gel blotting.

Example 6

Purifying the Dehydrogenase from *Candida magnoliae*

For the purpose of fermentating *Candida magnoliae* Lu8742, 2 precultures were grown, at 28° C. for 15 hours and at 200 rpm, in 150 ml of medium containing 8 g of yeast extract (65%)/l, 5 g of peptone/l, 3.5 g of glucose/l, 5 g of Ammonium Sulfate Precipitation:

41 ml of Q-Sepharose useful peak fractions were brought to 90% saturation with (NH$_4$)$_2$SO$_4$ (pH 6.2), stirred for 30 min at 4° C. and then centrifuged at 10 000 g for 10 min. The result pellet was suspended in 10 ml 20 mM MES, 1 mM MgCl$_2$, 1 Roche Complete (without EDTA) tablet/l, pH 6.2 and this suspension was dialyzed for 30 min against 20 mM MES, 1 mM MgCl$_2$, 1 Roche Complete (without EDTA) tablet/l, pH 6.2, in a Pierce Slide-A-Lyzer (10 kDa exclusion volume).

Superdex Molecular Sieve Chromatography:

A Superdex 200 molecular sieve column (Pharmacia) having a diameter of 2.6 cm and a volume of 240 ml was equilibrated in 20 mM MES, 1 mM MgCl$_2$, 1 Complete tablet per liter of buffer (EDTA-free), pH 6.2. The dialyzate from the ammonium sulphate precipitation (2×7 ml) was loaded onto the molecular sieve column at a flow rate of 4 ml per minute. 4 ml fractions were collected and tested. Fractions 21 to 24 were again active for both substrates.

Mono-Q ion Exchange Chromatography:

A Mono-Q HR5/5 column (from Pharmacia) having a volume of 1 ml was equilibrated in 20 mM MES, 1 mM MgCl$_2$, pH 6.8. 10 ml of the combined useful fractions from the Superdex column were loaded on at a flow rate of 1 ml per minute. After the column had been washed, it was developed with a linear gradient of up to 100% 20 mM MES, 1 mM MgCl$_2$, 0.75 M NaCl, pH 6.8 in 100 minutes and subsequently washed for 10 min with 20 mM MES, 1 mM MgCl$_2$, pH 6.8. 1 ml fractions were collected (detection, 226 nm). Active fractions (fractions 24 to 27) were combined.

The result of the isolation is summarized in the following table

| Sample | Vol. [ml] | Activity [U/l] | Total activity [mU] | Activity yield [%] | Protein [g/L] | Total protein [mg] | Protein yield [%] | ee(*) | Spec. act. [U/g of protein] |
|---|---|---|---|---|---|---|---|---|---|
| Homogenate | 650 | 30 | 19500 | 100.0% | 5.70 | 3705 | 100 | 72.1 | 5.3 |
| Q-UP | 54 | 42.8 | 2310 | 11.8% | 3.58 | 193 | 5.2 | 84.6 | 11.9 |
| AS pptn. | 18 | 217.2 | 4005 | 20.5% | 5.49 | 101 | 2.7 | 91.3 | 39.6 |
| Superdex-UP | 49 | 35.6 | 1733 | 8.9% | 0.33 | 16.1 | 0.43 | 91.6 | 107.7 |
| MonoQ-UP | 12 | 12.5 | 148 | 0.8% | 0.05 | 0.44 | 0.01 | 97.0 | 253.0 |

*(S)-3-Chloro-1-(thien-2-yl)propan-1-ol
AS pptn.: ammonium sulfate precipitation
UP: useful peak fractions The N terminus of the dehydrogenase which had been purified in this way was determined by means of Edman sequencing (SEQ ID NO: 2) following SDS-PAGE and gel blotting.

Example 7

Preparing (S)-3-methylamino-1-(thien-2-yl)propan-1-ol I-S by Means of Reducing with a *Lactobaccillus brevis* dehydrogenase

*Lactobaccillus brevis* Lu10288 was grown and harvested as described in Example 4. The resting cells (10-100 g/l of biomass) were treated with 0.2-2 mM NAD(P)$^+$, from 1 to 100 g of the propanone from Example 1 (batch or fed-batch)/l and 18 g of glucose/l and incubated at 30° C. for 2-8 h. The reaction was kept at pH 6.0-7.0 by titrating with 0.5 M NaOH and monitored by HPLC analysis. FIGS. 2A and B show typical reaction sequences corresponding to mixtures 1 and 2, respectively.

| Mixture 1: | |
|---|---|
| 9 ml | of Lu10288 cell suspension (containing 200 g of MBM/l) |
| 3 ml | of 1 M glucose solution |
| 3 ml | of 20 mM NADP solution |
| 0.9 ml | of GDH solution (12-15 U/µl) |
| 3 ml | of 1 M NaCl solution |
| 11.1 ml | of water |
| +10 mM | ketone (from Example 1) |

10 mM ketone were added once again after 1 h.

| Mixture 2: | |
|---|---|
| 9 ml | of Lu10288 cell suspension (200 g of MBM/l) |
| 3 ml | of 1 M glucose solution |
| 3 ml | of 2 mM NADP solution |
| 3 ml | of 2 mM NAD solution |
| 0.9 ml | of GDH solution (12-15 U/µl) |
| 3 ml | of 1 M NaCl solution |
| 11.1 ml | of water |
| +10 mM | ketone (0.6 ml of 0.5 M ketone from Example 1 in methanol) |

10 mM ketone were in each case added once again after 45, 110, 180 and 300 min.

Subsequently, the biomass was removed by means of centrifugation and/or filtration. The NMR analysis of the MTBE extracts gave a 3-chloro-1-(thien-2-yl)propan-1-ol content of 60-70%. The contents of unreacted 3-chloro-1-(thien-2-yl) propan-1-one and of the by-product 1-thien-2-ylpropen-1-one were in each case less than 10%. It was only possible to detect 1-thien-2-yl-propen-1-ol in traces.

1.1 g of 40% aqueous methylamine solution was then added to the cell-free aqueous mixture. The latter was then stirred at 60° C. for 6 h under intrinsic pressure. After the mixture had been cooled down to room temperature, the solvent was removed; the residue was then digested with toluene and filtered off from it. As an alternative, it was possible to carry out the cell separation after the amination reaction. After the filtrate had been dried, 202 mg of the title compound were obtained in the form of a pale yellow solid. The S enantiomer was obtained in an enantiomeric excess of 95% ee. The ee value was determined by determining the amount of rotation (c=1, solvent: methanol) and by means of Shift NMR (Shift reagent: 2,2,2-trifluoro-1-(9-anthryl)ethanol (+) (TFAE); solvent: CDCl$_3$; 500 MHz)

Example 8

Cloning the Dehydrogenase from *Lactobaccillus brevis* Lu10288 a) Preparing Chromosomal DNA from LU10288 Following Prior Protoplasting:

(1) Solutions Required

| Solution 1: | 0.41 M sucrose |
|---|---|
| | 0.01 M MgSO$_4$*7H$_2$O |

-continued

```
5 ml/l M12 medium 1:2
10 ml/l 10% KH₂PO₄ pH 6.7
2.5 mg/ml lysozyme (add shortly before use)
```

Solution 1 is prepared as follows:
14.03 g of sucrose, 0.25 g of MgSO$_4$*7H$_2$O, 5 ml of M12 (10× conc) and 1 ml of 10% KH$_2$PO$_4$, pH 6.7, make up to 100 ml and sterilize by filtration.

| Proteinase: | from Qiagen, 20 mg/ml stock solution |
| RNase: | from Qiagen, 100 mg/ml stock solution |
| TE buffer: | 10 mM Tris*Cl pH 8, 1 mM EDTA pH 8 |

(2) Culture and Disruption:
Culture overnight in 100 ml of MRS medium (from Difco) in 250 ml baffled Erlenmeyer flasks at 37° C. and 200 rpm.
Centrifuge the cells: 4000 rpm, 10 min, 4° C.
Discard the supernatant and take up the pellet in 5 ml of solution 1 (+ lysozyme) and resuspend it well. Incubate it in an incubator (37° C.) for 1-4 h.
Carefully centrifuge the protoplasts: 3000 rpm, 10 min.
Discard the supernatant, wash the pellet with 10 ml of solution 1 (without lysozyme): 3000 rpm, 4° C., 8 min.
Discard the supernatant, wash the pellet with 10 ml of 0.01 M Tris-HCl, pH 8.0: 3000 rpm, 4° C., 8 min.
Discard the supernatant, resuspend the pellet in 4 ml of TE buffer.
Add 0.5 ml of 10% SDS and 0.5 ml of 5M NaCl, mix carefully.
Add 1 mg of proteinase K (Qiagen proteinase: 20 mg/ml, that is 50 µl) and incubate at 37° C. overnight in an incubator.
Make this mixture up to 20 ml with TE buffer.

(3) Extraction:
Add phenol 1:1, i.e. 20 ml of phenol+20 ml of mixture. Mix carefully and centrifuge at 4000 rpm for 5 min at 4° C.
Take off the upper phase and transfer it to a new Falcon (20 ml).
Add 20 ml of phenol:chloroform:isoamyl alcohol (25:24:1). Mix carefully and centrifuge at 4000 rpm for 5 min and at 4° C.
Take off upper phase and transfer to a new Falcon (approx. 18 ml).
Add 18 ml of chloroform:isoamyl alcohol (24:1, that is 18 ml of chloroform+333 µl of isoamyl alcohol). Mix carefully and centrifuge at 4000 rpm for 5 min at 4° C. Repeat this step until the upper phase is clear.
Precipitate the upper phase (18 ml) with 2 volumes of ethanol (36 ml). Add 1/50 3M sodium acetate (approx. 360 µl). Leave to precipitate at −20° C. for at least 30 min. After than, centrifuge at 12 000 rpm for 30 min at 4° C.
Discard supernatant, take up pellet in 1-2 ml of TE buffer. Add 20 µg of RNase per ml of TE buffer. Incubation: 1 h, 37° C. in a water bath.

(4) Dialysis:
Following RNase treatment, the mixture is transferred to a dialysis bag. It is dialyzed 3 times for in each case 1 hour at 4° C. in 1.5 L of TE buffer. It is also possible to carry out the last dialysis step overnight.

Transfer the dialyzed DNA to a Falcon and aliquot it into several Eppendorff tubes (500 µl).
Add 2 volumes of ethanol (1000 µl) and ⅓ volume of 2M LiCl (166 µl).
Precipitate at −20° C. for at least 30 min. After than, centrifuge at 12 000 rpm for 30 min at 4° C.
Carefully pour off the supernatant.
Wash the pellet with 20 ml of 70% ethanol and centrifuge at 12 000 rpm for 15 min at 4° C.
Carefully pour off the supernatant, allow the pellet to dry in air and take up the DNA in an appropriate volume of 10 mM Tris*HCl, pH 8.0 (from 100 µl upwards depending on the pellet size).

In order to improve redissolution, the DNA was incubated for 1-2 hours in an Eppendorf shaker at 55-60° C. at a low shaking frequency (400 rpm).

b) Following tryptic digestion and Edmann sequencing of the peptides, further amino acid sequences were obtained from the protein purification described in Example 5. The results of the sequence analysis are compiled in FIG. 3B.

Because of the break point, the sequence FVVDGGYTAQ (cf. V8-RP Fr.7) (SEQ ID NO: 12) presumably represents the C terminus. Nucleic acid sequences (primers Mke338 and 339), which were used as follows for cloning the dehydrogenase gene by means of PCR amplification performed on Lu10288 chromosomal DNA (protocol, see above), were deduced from this sequence and from the N-terminal amino acid sequence (SEQ ID NO. 1) while taking account of the *Lactobaccillus brevis* codon usage.

PCR:

| Template | Primers | Product length |
|---|---|---|
| Lu10288 chromosomal DNA* | Mke338 + Mke339 | approx. 800 bp |

*prepared in accordance with Example 8a)

Primer:

| Primer No. | Sequence (5'-3') | Position |
|---|---|---|
| Mke338 (SEQ ID NO: 7) | GGGAATTC<u>CATATG</u>TCTAACCGTTTGG | N-term. primer (NdeI) |
| Mke339 (SEQ ID NO: 8) | CGTAGGG<u>AAGCTT</u>ATTGAGCAGTGTAGCC | C-term. primer (HindIII) |

The PCR was carried out in accordance with the standard Stratagene protocol using Pfu polymerase (Stratagene) and the following temperature program: 95° C. for 5 minutes; 30 cycles of 95° C. for 45 sec., 52° C. for 45 sec, and 72° C. for 1 min 20 sec; 72° C. for 10 min.; 10° C. until use. The PCR product (0.8 kb) was isolated by means of agarose gel electrophoresis (1.2% E-Gel, Invitrogen) and column chromatography (Mini-Elute, Qiagen) and then digested with NdeI/HindIII and cloned into the correspondingly digested pDHE19.2 vector (a pJOE derivative, DE19848129). The ligation mixtures were transformed into *E.coli* XL1 Blue (Stratagene). The sequencing of corresponding clones gave, as the insert in the resulting plasmid pDHE10288adh1, the nucleic acid sequence depicted in SEQ ID NO:3, which sequence corresponds to the amino acid sequence SEQ ID NO:4. All the peptides identified in Examples 5 and 8 are found once again in this sequence.

```
SEQ ID NO: 4 Amino acid sequence of the Lu10288 dehydrogenase

1 MSNRLDGKVA IVTGGTLGIG LAIATKFVEE GAKVMITGRH SDVGEKAAKS

51 VGTPDQIQFF QHDSSDEDGW TKLFDATEKA FGPVSTLVNN AGIAVNKSVE

101 ETTTAEWRKL LAVNLDGVFF GTRLGIQRMK NKGLGASIIN MSSIEGFVGD

151 PSLGAYNASK GAVRIMSKSA ALDCALKDYD VRVNTVHPGY IKTPLVDDLP

201 GAEEAMSQRT KTPMGHIGEP NDIAYICVYL ASNESKFATG SEFVVDGGYT

251 AQ*

SEQ ID NO: 3 Nucleic acid sequence of the Lu10288
dehydrogenase (and also the counterstrand)

1 ATGTCTAACC GTTTGGATGG AAAAGTAGCA ATCGTTACAG GTGGTACGTT
    TACAGATTGG CAAACCTACC TTTTCATCGT TAGCAATGTC CACCATGCAA

51 GGGTATCGGT TTAGCTATCG CCACGAAGTT CGTTGAAGAA GGGGCTAAGG
    CCCATAGCCA AATCGATAGC GGTGCTTCAA GCAACTTCTT CCCCGATTCC

101 TCATGATTAC CGGCCGGCAC AGCGATGTTG GTGAAAAAGC AGCTAAGAGT
    AGTACTAATG GCCGGCCGTG TCGCTACAAC CACTTTTTCG TCGATTCTCA

151 GTCGGCACTC CTGATCAGAT TCAATTTTTC AACATGATT CTTCCGATGA
    CAGCCGTGAG GACTAGTCTA AGTTAAAAAG GTTGTACTAA GAAGGCTACT

201 AGACGGCTGG ACGAAATTAT TCGATGCAAC GGAAAAAGCC TTTGGCCCAG
    TCTGCCGACC TGCTTTAATA AGCTACGTTG CCTTTTTCGG AAACCGGGTC

251 TTTCTACATT AGTTAATAAC GCTGGGATCG CGGTTAACAA GAGTGTCGAA
    AAAGATGTAA TCAATTATTG CGACCCTAGC GCCAATTGTT CTCACAGCTT

301 GAAACCACGA CTGCTGAATG GCGTAAACTA TTAGCCGTCA ACCTTGATGG
    CTTTGGTGCT GACGACTTAC CGCATTTGAT AATCGGCAGT TGGAACTACC

351 TGTCTTCTTC GGTACCCGAT TAGGGATTCA ACGGATGAAG AACAAAGGCT
    ACAGAAGAAG CCATGGGCTA ATCCCTAAGT TGCCTACTTC TTGTTTCCGA

401 TAGGGGCTTC CATCATCAAC ATGTCTTCGA TCGAAGGCTT TGTGGGTGAT
    ATCCCCGAAG GTAGTAGTTG TACAGAAGCT AGCTTCCGAA ACACCCACTA

451 CCTAGCTTAG GGGCTTACAA CGCATCTAAA GGGGCCGTAC GGATTATGTC
    GGATCGAATC CCCGAATGTT GCGTAGATTT CCCCGGCATG CCTAATACAG

501 CAAGTCAGCT GCCTTAGATT GTGCCCTAAA GGACTACGAT GTTCGGGTAA
    GTTCAGTCGA CGGAATCTAA CACGGGATTT CCTGATGCTA CAAGCCCATT

551 ACACTGTTCA CCCTGGCTAC ATCAAGACAC CATTGGTTGA TGACCTACCA
    TGTGACAAGT GGGACCGATG TAGTTCTGTG GTAACCAACT ACTGGATGGT

601 GGGGCCGAAG AAGCGATGTC ACAACGGACC AAGACGCCAA TGGGCCATAT
    CCCCGGCTTC TTCGCTACAG TGTTGCCTGG TTCTGCGGTT ACCCGGTATA

651 CGGTGAACCT AACGATATTG CCTACATCTG TGTTTACTTG GCTTCTAACG
    GCCACTTGGA TTGCTATAAC GGATGTAGAC ACAAATGAAC CGAAGATTGC

701 AATCTAAATT TGCAACGGGT TCTGAATTTG TAGTTGACGG TGGCTACACT
    TTAGATTTAA ACGTTGCCCA AGACTTAAAC ATCAACTGCC ACCGATGTGA

751 GCTCAA
    CGAGTT
```

Example 9

Determining the Activity of the Recombinant Dehydrogenase from *Lactobaccillus brevis* Lu10288

The plasmid pDHE10288adh1 was retransformed into *E.coli* TG10 pAgro4 pHSG575 (TG10: an RhaAk[31] derivative of *E.coli* TG1(Stratagene); pAgro4: Takeshita, S; Sato, M; Toba, M; Masahashi, W; Hashimoto-Gotoh, T (1987) Gene 61, 63-74; pHSG575: T. Tomoyasu et al. (2001), Mol. Microbiol. 40(2), 397-413).

In each case 6 transformants were grown, at 37° C. for 18 h, in 20 ml of LBAmp/Spec/Cm (100 µg of Amp/l; 50 mg of Spec/l; 10 µg of Cm/l), 0.1 mM IPTG, 0.5 g of rhamnose/l, in a (baffled) 100 ml Erlenmeyer flask, then centrifuged at 5000 g for 10 min, washed once with 10 mM Tris/HCl, pH 7.0, and resuspended in 2 ml of the same buffer. 100 µl of cell suspension were incubated, for 20 min and with shaking, in 900 µl of 50 mM MES, pH 6, containing 50 µl of glucose DH/ml (Example 1), 100 mM glucose, 100 mM NaCl, 1 mM NADH, 1 mM NADPH and 10 mM 3-chloro-1-(thien-2-yl)propan-1-one. The mixtures were analyzed in analogy with Example 4. On average, 0.13 mM 3-chloro-1-(thien-2-yl)propan-1-ol was formed, corresponding to an activity of 6.6 U/l of culture suspension. In analogous assay samples containing crude extract, which was obtained by means of cell disruption using 0.7 ml of glass beads (d=0.5 mm) in a vibratory mill (3×5 min with cooling on ice in the interval), 0.21 mM 3-chloro-1-(thien-2-yl)propan-1-ol, corresponding to an activity of 10.7 U/l, was measured. It was not possible to detect any 3-chloro-1-(thien-2-yl)propan-1-ol in control experiments in which no rhamnose was added during the culture.

Example 10

Cloning the Dehydrogenase from *Candida magnoliae* Lu8472

The following amino acid sequence was obtained from the protein purification described in Example 6 after once again determining the N-terminal sequence by means of Edmann sequencing:

(S,G or T)(T or P)TSNALVTGGSRGIGAA (SEQ ID NO: 13)

The following additional amino acid sequence was obtained following tryptic digestion and Edmann sequencing of the peptides:

IGVNSINPG (SEQ ID NO: 14)

Nucleic acid sequences (primers Mke366, 367 und 374), which were used as follows for cloning the dehydrogenase gene by means of PCR amplification performed on Lu8472 chromosomal DNA (Genomic DNA kit using three-fold concentrated Lyticase solution, Qiagen, Hilden), were deduced from the peptides while taking account of the *Candida magnoliae* codon usage.

PCR:

| Template | Primers | Product length |
| --- | --- | --- |
| Chromosomale Lu8472 DNA | Mke366/367 + Mke374 | approx. 480 bp |

Primers:

| Primer No. | Sequence (5'-3') | Position |
| --- | --- | --- |
| Mke366 (SEQ ID NO: 9) | ACGACGACG<u>AG</u>CAACGCBCTBGTBACGG | N term. primer |
| Mke367 (SEQ ID NO: 10) | ACGACGACG<u>TC</u>GAACGCBCTBGTBACGG | N term. primer |
| Mke374 (SEQ ID NO: 11) | GCCGGGGTTGATSSWGTTSACGCCGAT | C term. primer |

The primers MKe366 and MKe367 were mixed 1:1. The PCR was carried out in accordance with the standard Stratagene protocol using Pfu Turbo-Polymerase (Stratagene) and the following temperature gradient program: 95° C. for 1 minute; 30 cycles of 95° C. for 1 min., X° C.[1] for 45 sec and 72° C. for 2 min; 72° C. for 10 min; 10° C. until used. The PCR product (~0.5 kb) was isolated by means of agarose gel electrophoresis (1.2% E-Gel, Invitrogen) and column chromatography (GFX-Kit, Amersham Pharmacia) and then sequenced (sequencing primers: Mke366 and Mke374). The resulting sequence is depicted in SEQ ID NO:5. The amino acid sequence (SEQ ID NO:6) which is deduced from it exhibits 53% identity with *Candida magnoliae* carbonyl reductase (WO200140450). The peptide sequences which were determined following protein purification are present with only minor divergences. Differences could be due to sequencing errors or result from the existance of several isoenzymes in *Candida magnoliae* Lu8742.

[1] 12 assay samples were run at different annealing temperatures, i.e. of from 25° C. to 45° C. (Delta in each case approx. 2° C.). In all the assay samples, a 0.5 kb band of similar concentration was formed as the main product.

SEQ ID NO: 6 Partial amino acid sequence of the Lu8472 dehydrogenase

```
  1 NALVTGGSRG IGEATAIKLA EEGYSVTIAS RGLKQLEAVK AKLPIVKQGQ

51 VHHVWQLDLS DVDAAAAFKG SPLPASRYDV LVSNAGVAQF SPFIEHAKQD

101 WSQMLAINLA APIALAQTFA KAIGDKPRNT PAHIVFVSSN VSLRGFPNIG

151 VNSITPG
```

SEQ ID NO: 5 Partial nucleic acid sequence of the Lu8472 dehydrogenase (and also the counterstrand)

```
  1 AACGCGCTGG TGACGGGCGG CAGCCGCGGC ATTGGCGAAG CCACTGCCAT
    TTGCGCGACC ACTGCCCGCC GTCGGCGCCG TAACCGCTTC GGTGACGGTA

51 TAAGCTCGCC GAGGAGGGCT ACAGCGTCAC GATTGCGTCT CGCGGCCTTA
    ATTCGAGCGG CTCCTCCCGA TGTCGCAGTG CTAACGCAGA GCGCCGGAAT

101 AGCAGCTCGA GGCTGTGAAG GCCAAACTAC CCATTGTGAA GCAGGGACAG
    TCGTCGAGCT CCGACACTTC CGGTTTGATG GGTAACACTT CGTCCCTGTC
```

```
-continued

151 GTTCACCACG TGTGGCAGCT TGATCTCAGT GATGTCGACG CTGCGGCCGC
    CAAGTGGTGC ACACCGTCGA ACTAGAGTCA CTACAGCTGC GACGCCGGCG

201 CTTCAAAGGG TCGCCGCTAC CTGCCAGCCG CTACGACGTG CTCGTCAGCA
    GAAGTTTCCC AGCGGCGATG GACGGTCGGC GATGCTGCAC GAGCAGTCGT

251 ATGCTGGCGT GGCCCAGTTT AGCCCGTTCA TCGAGCATGC GAAGCAGGAC
    TACGACCGCA CCGGGTCAAA TCGGGCAAGT AGCTCGTACG CTTCGTCCTG

301 TGGTCGCAGA TGCTTGCCAT CAATCTGGCG CACCCATTG CGCTGGCCCA
    ACCAGCGTCT ACGAACGGTA GTTAGACCGC CGTGGGTAAC GCGACCGGGT

351 GACATTTGCT AAGGCCATTG GCGACAAGCC GCGCAACACA CCGGCCCACA
    CTGTAAACGA TTCCGGTAAC CGCTGTTCGG CGCGTTGTGT GGCCGGGTGT

401 TTGTGTTTGT CTCGTCGAAC GTCTCGTTGC GAGGCTTCCC GAACATCGGC
    AACACAAACA GAGCAGCTTG CAGAGCAACG CTCCGAAGGG CTTGTAGCCG

451 GTCAACTCCA TCACCCCCGG CA
    CAGTTGAGGT AGTGGGGGCC GT
```

---

We claim:

1. A process for preparing (S)-3-methylamino-1-(thien-2-yl)propan-1-ol of the formula I-S

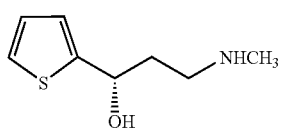

(I-S)

comprising a) reacting thiophene is with a β-halopropionyl halide or an acryloyl halide in the presence of a Lewis acid to give a 3-halo-1-(thien-2-yl)propan-1-one, with a hydrogen halide being passed in simultaneously or after the reaction has taken place, but before the reaction product is isolated, and b) reducing the propanone obtained in step a) and then reacting with methylamine; wherein step b) is carried out in the presence of a dehydrogenase which exhibits selectivity with regard to the formation of (S)-3-methylamino-1-(thien-2-yl)propan-1-ol.

2. The process as claimed in claim 1, wherein the dehydrogenase is an alcohol dehydrogenase.

3. The process as claimed in claim 1, wherein the dehydrogenase is selected from among dehydrogenases from yeasts of the genus *Geotrichum, Pichia, Candida, Hansenula* or *Saccharomyces* and from bacteria of the genus *Pseudomonas, Burkholderia, Agrobacterium, Rhodococcus* or *Lactobaccillus*.

4. A process as claimed in claim 3, wherein the dehydrogenase is selected from among dehydrogenases from *Geotrichum candidum, Candida magnoliae* and *Lactobaccillus brevis*.

5. The process as claimed in claim 1, wherein the dehydrogenase employed is an alcohol dehydrogenase having an amino acid sequence which, in the region of the N terminus a) comprises a constituent amino acid sequence of at least 10 consecutive amino acid residues as depicted in SEQ ID NO: 1, with the position corresponding to amino acid position 12 as depicted in SEQ ID NO: 1 additionally standing for valine; or a b) constituent amino acid sequence of at least 10 consecutive amino acid residues as depicted in SEQ ID NO: 2 or a dehydrogenase produced by a natural or recombinant microorganism.

6. A process for preparing (S)-3-methylamino-1-(thien-2-yl)propan-1-ol of formula I-S comprising reducing a 3-halo-1-(thien-2-yl)propan-1-one enantioselectively, wherein the reduction is effected in the presence of a dehydrogenase, producing a (S)-3-methylamino-1-(thien-2-yl)propan-1-ol of the formula I-S.

7. The process as claimed in claim 5, wherein the (S)-3-halo-1-(thien-2-yl)propan-1-ol which is obtained in the reduction is reacted with methylamine without being isolated.

8. The process as claimed in claim 5, wherein the dehydrogenase is selected from among dehydrogenases from yeasts of the genus *Geotrichum, Pichia, Candida, Hansenula* or *Saccharomyces* and from bacteria of the genus *Pseudomonas, Burkholderia, Agrobacterium, Rhodococcus* or *Lactobaccillus*.

9. The process as claimed in claim 7, wherein the dehydrogenase is selected from among dehydrogenases from *Geotrichum candidum, Candida magnoliae* or *Lactobaccillus brevis*.

10. The process as claimed in claim 5, wherein the dehydrogenase is selected from among alcohol dehydrogenases selected from the group consisting of a) a dehydrogenase capable of reducing 3-chloro-1-(thien-2-yl)propan-1-one to (S)-3-chloro-1-(thien-2-yl)propan-1-ol;

b) a dehydrogenase which catalyzes the reduction in an enantiomeric purity of at least 85% ee (in the presence of NADH and/or NADPH; at 30° C. and pH 6.0);

c) a dehydrogenase which is encoded by a nucleic acid sequence comprising SEQ ID NO: 3 or which comprises an amino acid sequence as depicted in SEQ ID NO: 4 or at least a constituent sequence as depicted in FIG. 3, and can preferably be obtained from *Lactobaccillus brevis*; or functionally an equivalent alcohol dehydrogenase which is derived therefrom; and d) a dehydrogenase which is encoded by a nucleic acid sequence comprising SEQ ID NO: 5 or which possesses an amino acid sequence comprising SEQ ID NO: 6 and can preferably be obtained from *Candida magnoliae* (ATCC 12573); or a functionally equivalent alcohol dehydrogenase which is derived therefrom.

* * * * *

UNITED STATES PATENT AND TRADEMARK OFFICE
CERTIFICATE OF CORRECTION

PATENT NO. : 7,498,448 B2  Page 1 of 1
APPLICATION NO. : 10/573130
DATED : March 3, 2009
INVENTOR(S) : Rainer Stürmer et al.

It is certified that error appears in the above-identified patent and that said Letters Patent is hereby corrected as shown below:

In claim 1b), in column 89, on lines 66-67, "methy-lamino" should read -- methylamino --.

In claim 6, in column 91, on line 5, "the formula I-S." should read -- formula I-S --.

In claim 9, in column 91, on line 17, "The process as claimed in claim 7," should read -- The process as claimed in claim 8 --.

In claim 10 b), in column 92, on line 7, "30°C.," should read -- 30°C --.

Signed and Sealed this

Twenty-third Day of June, 2009

JOHN DOLL
*Acting Director of the United States Patent and Trademark Office*